US012612617B2

(12) United States Patent (10) Patent No.: US 12,612,617 B2
Campbell et al. (45) Date of Patent: Apr. 28, 2026

(54) MITOCHONDRIAL GENOME EDITING METHODS

(71) Applicant: Mayo Foundation for Medical Education and Research, Rochester, MN (US)

(72) Inventors: Jarryd M. Campbell, Rochester, MN (US); Stephen C. Ekker, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 1026 days.

(21) Appl. No.: 17/425,876

(22) PCT Filed: Jan. 28, 2019

(86) PCT No.: PCT/US2019/015439
§ 371 (c)(1),
(2) Date: Jul. 26, 2021

(87) PCT Pub. No.: WO2020/159470
PCT Pub. Date: Aug. 6, 2020

(65) Prior Publication Data
US 2022/0162583 A1 May 26, 2022

(51) Int. Cl.
*C12N 9/22* (2006.01)
*C12N 15/10* (2006.01)
(52) U.S. Cl.
CPC ............. *C12N 15/102* (2013.01); *C12N 9/22* (2013.01); *C12Y 301/21004* (2013.01)
(58) Field of Classification Search
None
See application file for complete search history.

(56) References Cited

U.S. PATENT DOCUMENTS

| | | | |
|---|---|---|---|
| 6,395,523 | B1 | 5/2002 | Kong et al. |
| 8,586,363 | B2 | 11/2013 | Voytas et al. |
| 2007/0099216 | A1 | 5/2007 | Nakashima et al. |
| 2008/0131962 | A1 | 6/2008 | Miller |
| 2011/0145940 | A1 | 6/2011 | Voytas et al. |
| 2014/0212928 | A1 | 7/2014 | Wang |
| 2014/0294773 | A1 | 10/2014 | Johan et al. |
| 2014/0338070 | A1 | 11/2014 | Cigan et al. |
| 2015/0291951 | A1 | 10/2015 | Ekker et al. |
| 2019/0024073 | A1 | 1/2019 | Ekker et al. |
| 2019/0119701 | A1* | 4/2019 | Liang ....................... C12N 9/22 |
| 2019/0330603 | A1* | 10/2019 | Ahlfors .................. C12N 15/11 |

FOREIGN PATENT DOCUMENTS

| | | |
|---|---|---|
| WO | WO 2004/067736 | 8/2004 |
| WO | WO 2013/191769 | 12/2013 |
| WO | WO 2014/144987 | 9/2014 |
| WO | WO 2016/118560 | 7/2016 |
| WO | WO 2017/015567 | 1/2017 |
| WO | WO 2017/136520 | 8/2017 |
| WO | WO 2017/222834 | 12/2017 |

OTHER PUBLICATIONS

Mikhail Alexeyev, Mitochondrial DNA: the common confusions, Mitochondiral DNA: A DNA Mapp Seq Anal. (2020) 31(2): 45-47 (Year: 2020).*
Campbell et al., Engineering targeted deletions in the mitochondrial genome. bioRxiv preprint, doi: https://doi.org/10.1101/287342 (Year: 2018).*
Phillips et al., Single-Molecule Analysis of mtDNA Replication Uncovers the Basis of the Common Deletion. Molecular Cell (2017), 65: 527-538 (Year: 2017).*
Kevin Kotredes, Dissertation: Characterization of the Effects of IDH2 mutations and (R)-2-HG in Cancer Progression, Dec. 2015 (Year: 2015).*
Rong et al., The Mitochondrial Response to DNA Damage. Frontiers in Cell and Developmental Biology (2021), 9:669379, 1-10 (Year: 2021).*
Alexeyev et al., "Selective elimination of mutant mitochondrial genomes as therapeutic strategy for the treatment of NARP and MILS syndromes," Gene There, 15:516-523, Apr. 2008.
Alexeyev et al., "The Maintenance of Mitochondrial DNA Integrity-Critical Analysis and Update," Cold Spring Harb. Perspect, Biology, 5(5):a012641, May 2013, 19 pages.
Artuso et al., "Mitochondrial DNA metabolism in early development of zebrafish (*Danio rerio*)," Biochim Biophys Acta, 1817: 1002-1011, Jul. 2012.
Bacman et al., "Intra- and inter-molecular recombination of mitochondrial DNA after in vivo induction of multiple double-strand breaks," Nucleic Acids Research, 37(13):4218-4226, Jul. 2009.
Bacman et al., "Manipulation of mtDNA heteroplasmy in all striated muscles of newborn mice by AAV9-mediated delivery of a mito-chondria-targeted restriction endonuclease," Gene Therapy, 19(11):1101-1106, Dec. 2011.
Bacman et al., "Specific elimination of mutant mitochondrial genomes in patient-derived cells by mito TALENs," Nat Med, 19:1111-1113, Sep. 2013.
Bayona-Bafaluy et al., "Rapid directional shift of mitochondrial DNA heteroplasmy in animal tissues by a mitochondrially targeted restriction endonuclease," PNAS, 102: 14392-14397, Oct. 2005.

(Continued)

*Primary Examiner* — Catherine Konopka
(74) *Attorney, Agent, or Firm* — Fish & Richardson P.C.

(57) ABSTRACT

Disclosed is a method for editing mitochondrial DNA (mtDNA) within a cell, which include introducing into the cell (a) a DNA cleaving enzyme targeted to the mtDNA sequence to be deleted; (b) a first DNA binding component targeted to a sequence adjacent to the 5' end of a mtDNA sequence to be deleted; and (c) a second DNA binding component targeted to a sequence adjacent to the 3' end of the mtDNA sequence to be deleted, where the DNA cleaving enzyme generates a double stranded break (DSB) within the mtDNA sequence to be deleted or generates a single strand nick on the light strand of the mtDNA sequence to be deleted, and wherein the mtDNA sequence between the target sequence for the first DNA binding component and the target sequence for the second DNA binding component is deleted.

17 Claims, 29 Drawing Sheets
Specification includes a Sequence Listing.

(56) References Cited

OTHER PUBLICATIONS

Bedell et al., "In vivo genome editing using a high-efficiency TALEN system," Nature, 491:114-118, Nov. 2012.

Bitinaite et al., "FokI dimerization is required for DNA Cleavage," PNAS, 95: 10570-10575, Sep. 1998.

Broughton et al., "The complete sequence of the zebrafish (*Danio rerio*) mitochondrial genome and evolutionary patterns in vertebrate mitochondrial DNA," Genome Res, 11:1958-1967, Nov. 2001.

Campbell et al., "Engineering targeted deletions in the mitochondrial genome," bioRxiv, Mar. 22, 2018, 16 pages.

Campbell et al., "Mitochondrial DNA editing in vivo using a novel "block and nick" system," Poster, Presented at Proceedings of the Keystone Symposia on Molecular and Cellular Biology, Keystone, CO, USA, Jan. 28-Feb. 1, 2018, 8 pages.

Clark et al., "In vivo protein trapping produces a functional expression codex of the vertebrate proteome," Nat Methods, 8: 506-515, Jun. 2011.

Claros et al., "Computational method to predict mitochondrially imported proteins and their targeting sequences," Eur. J. Biochem., 241:779-786, 1996.

Fan et al., "A mouse model of mitochondrial disease reveals germline selection against severe mtDNA mutations," Science, 319: 958-962, Feb. 2008.

Gammage et al., "Mitochondrial Genome Engineering: The Revolution May Not be CRISPR-Ized," Trends Genetics, 34(2):101-110, Nov. 24, 2017.

Gammage et al., "Mitochondrially targeted ZENs for selective degradation of pathogenic mitochondrial genomes bearing large-scale deletions or point mutation," Embo. Molecular Medicine, 6(4):458-466, Feb. 2014.

Goldstein et al., "Mitochondrial DNA Deletion Syndromes," in GeneReviews, University of Washington, Seattle, Dec. 17, 2003, 26 pages.

Gu et al., "R gene expression induced by a type-III effector triggers disease resistance in rice," Nature, 435:1122, Jun. 2005.

Gupta et al., "Dissection of Organs from the Adult Zebrafish," J. Vix. Experiments, 37:e1717, Mar. 2010, 5 pages.

Hashimoto et al., "MitoTALEN: A General Approach to Reduce Mutant mtDNA Loads and Restore Oxidative Phosphorylation Function in Mitochondrial Diseases," Mol Ther, 23:1592-1599, Oct. 2015.

Hyatt et al., "Vectors and techniques for ectopic gene expression in zebrafish," Methods Cell Biology, 59:117-126, 1999.

Jinek et al., "A Programmable Dual-RNA-Guided DNA Endonuclease in Adaptive Bacterial Immunity," Science, 337: 816-821, Aug. 2012.

Jo et al., "Efficient Mitochondrial Genome Editing by CRISPR/Cas9," Biomed Research International, 2015(305716):1-10, Jan. 2015.

Kay et al., "A bacterial effector acts as a plant transcription factor and induces a cell size regulator," Science, 318:648, 2007.

Kil et al., "Small interfering RNA-mediated silencing of mitochondrial NADP+-dependent isocitrate dehydrogenase enhances the sensitivity of HeLa cells toward tumor necrosis factor-α and anticancer drugs," Free Radical Biology and Medicine, 43(8):1197-1207, Oct. 2007.

Kim et al., "Hybrid restriction enzymes: zinc finger fusions to Fok I cleavage domain," PNAS, 93: 1156-1160, 1996.

Kim et al., "Precision genome engineering with programmable DNA-nicking enzymes," Genome Research, 22(7):1327-1333, Jul. 2012.

Li et al., "Multiplex and homologous recombination-mediated genome editing in *Arabidopsis* and. *Nicotiana benthamiana* using guide RNA and Cas9," Nature Biotechnol, 31(8):688-691, Aug. 2013.

Lin et al., "Mouse mtDNA mutant model of Leber hereditary optic neuropathy," Proc. Natl. Acad. Sci. USA, 109(49):20065-20070, Dec. 4, 2012.

Ma et al., "FusX: A Rapid One-Step Transcription Activator-Like Effector Assembly System for Genome Science," Hum Gene Ther, 27(6): 451-463, Jun. 2016.

Makarova et al., "Evolution and classification of the CRISPR-Cas systems," Nat. Rev. Microbiol., 9(6): 467-477, Jun. 2011.

Mali et al., "RNA-Guided Human Genome Engineering via Cas9," Science, 339:823-826, Feb. 2013.

Minczuk et al., "Development of a single-chain, quasi-dimeric zinc-finger nuclease for the selective degradation of mutated human mitochondrial DNA," Nucleic Acids Res, 36:3926-3938, May 2008.

Moraes et al., "Mitochondrial DNA deletions in progressive external ophthalmoplegia and Kearns-Sayre syndrome," N. Engl. J. Med., 320: 1293-1299, May 1989.

Ojala et al., "tRNA punctuation model of RNA processing in human mitochondria." Nature, 290(5806):470-474, Apr. 9, 1981.

Patananan et al., "Modifying the Mitochondrial Genome," Cell Metabolism, 23(5):785-796, May 10, 2016.

PCT International Preliminary Report on Patentability in International Appln. No. PCT/US2019/015439, dated Jul. 27, 2021, 7 pages.

PCT International Search Report and Written Opinion in International Appln. No. PCT/US2019/015439, dated Apr. 15, 2019, 11 pages.

Phillips et al., "Single-Molecule Analysis of mtDNA Replication Uncovers the Basis of the Common Deletion," Mol. Cell, 65(3):527-538.e6, Feb. 2, 2017.

Porteus et al., "Chimeric nucleases stimulate gene targeting in human cells," Science, 300:763, May 2003.

Rachek et al., "Endonuclease III and endonuclease VIII conditionally targeted into mitochondria enhance mitochondrial DNA repair and cell survival following oxidative stress," Nucleic Acids Res., 32(10): 3240-3247, Jan. 2004.

Reddy et al., "Selective elimination of mitochondrial mutations in the germline by genome editing," Cell, 161:459-469, Apr. 2015.

Reitman et al., "Isocitrate Dehydrogenase 1 and 2 Mutations in Cancer: Alteration at a Crossroads of Cellular Metabolism," J. Natl. Cancer Inst., 102:932-941, Jul. 2010.

Romer et al., "Plant pathogen recognition mediated by promoter activation of the pepper Bs3 resistance gene," Science, 318:645, Oct. 2007.

Schnorack et al., "Gene-for-gene-mediated recognition of nuclear-targeted AvrBs3-like bacterial effector proteins," J Plant Physiol, 163:256, Feb. 2006.

Schon et al., "A direct repeat is a hotspot for large-scale deletion of human mitochondrial DNA," Science, 244:346-349, Apr. 1989.

Sciacco et al., "Distribution of wild-type and common deletion forms of mtDNA in normal and respiration-deficient muscle fibers from patients with mitochondrial myopathy," Hum. Mol. Genet., 3:13-19, Jan. 1994.

Shen et al., "Repair of mitochondrial DNA damage induced by bleomycin in human cells," Mutat. Research, 337(1):19-23, Jul. 1995.

Sieber et al., "A protein shuttle system to target RNA into mitochondria," Nucl Acids Res, 39(14):e96, Aug. 2011.

Srivastava et al., "Double-strand breaks of mouse muscle mtDNA promote large deletions similar to multiple mtDNA deletions in humans," Hum. Mol. Genetics, 14(7):893-902, Apr. 2005.

Stewart et al., "The dynamics of mitochondrial DNA heteroplasmy: implications for human health and disease," Nat. Rev. Genetics, 16(9):530-542, Sep. 2015.

Sugio et al., "Two type III effector genes of *Xanthomonas oryzae* pv: *oryzae* control the induction of the host genes OsTFIIAgamma1 and OsTFX1 during bacterial blight of rice," PNAS, 104:10720, Jun. 2007.

Tadi et al., "Microhomology Mediated End Joining is the Principal Mediator of Double-strand Break Repair During Mitochondrial DNA Lesions," Mol. Biol. Cell, 27(2):223-235, Jan. 15, 2016.

Taylor et al., "Mitochondrial DNA mutations in human disease," Nat. Rev. Genetics, 6(5):389-402, May 2005.

Trifunovic et al., "Premature ageing in mice expressing defective mitochondrial DNA polymerase," Nature, 429(6990):417-423, May 27, 2004.

(56)                    References Cited

OTHER PUBLICATIONS

Tyynismaa et al., "Mouse models of mitochondrial DNA defects and their relevance for human disease," EMBO Reports, 10(2):137-143, Feb. 2009.

Vafai et al., "Mitochondrial disorders as windows into an ancient organelle," Nature, 491(7424):374-383, Nov. 15, 2012.

Wallace et al., "Mitochondrial DNA genetics and the heteroplasmy conundrum in evolution and disease," Cold Spring Harb. Perspect. Biology, 5(11):a021220, Nov. 1, 2013, 49 pages.

Waugh et al., "Single amino acid substitutions uncouple the DNA binding and strand scission activities of Fok I endonuclease," PNAS, 90:9596-9600, Oct. 1993.

Yang et al., "Os8N3 is a host disease-susceptibility gene for bacterial blight of rice," PNAS, 103:10503, Jul. 2006.

U.S. Appl. No. 15/746,912, filed Jan. 23, 2018, Stephen C. Ekker, Published as US 2019/0024073.

Shrivastav et al., "Regulation of DNA double-strand break repair pathway choice," Cell Res., Jan. 2008, 18(1):134-147.

Stumpf et al., "Mitochondrial DNA replication and disease: insights from DNA polymerase y mutations," Cell Mol. Life Sci., Jan. 2011, 68(2):219-233.

\* cited by examiner

FIG. 1A mito-nickases

WT mtDNA
'homoplasmy'

WT and ΔmtDNA
'heteroplasmy'

FIG. 1B nd4 mito-nickase (1)     dFokI

Figure 1B:
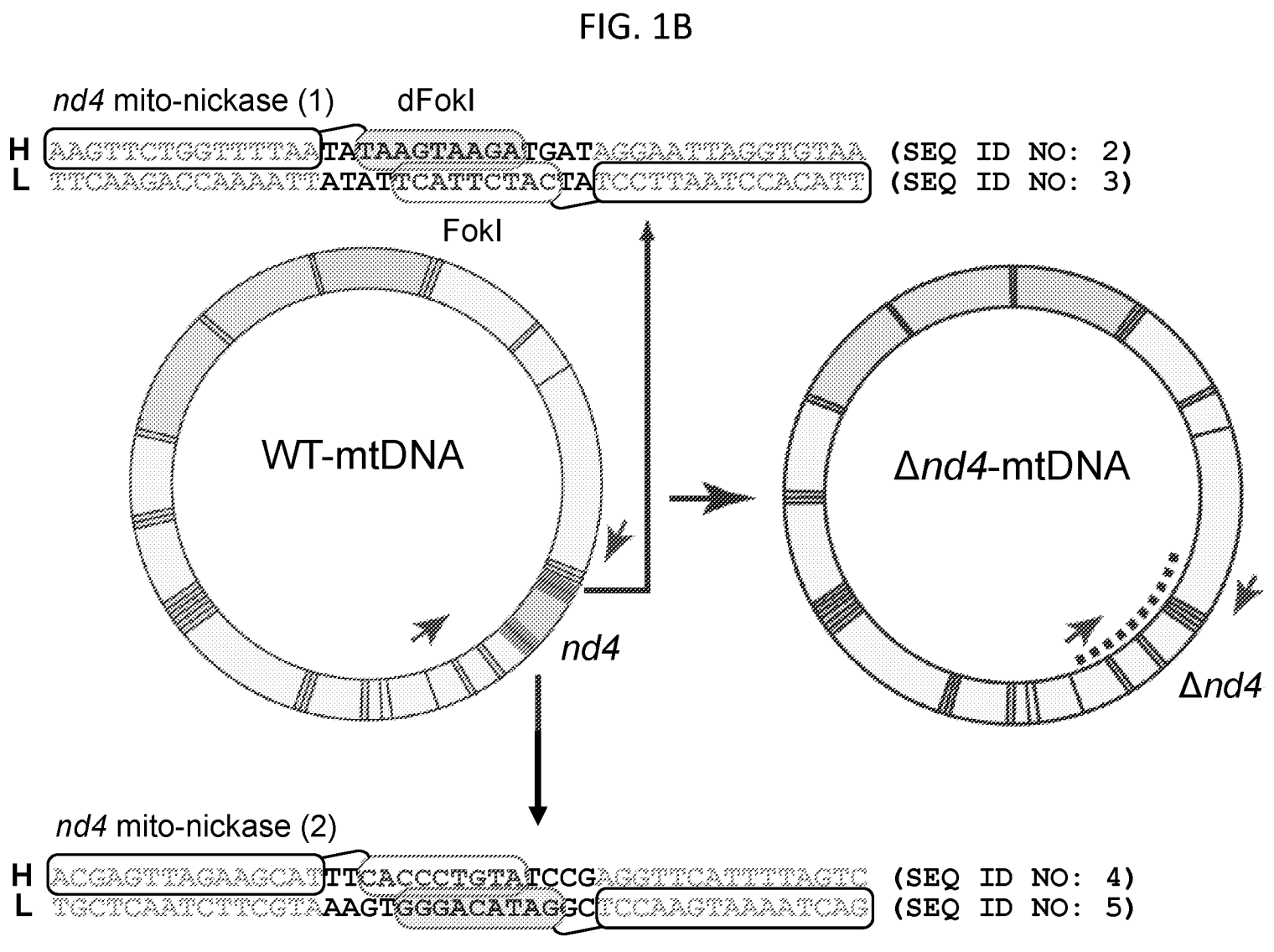

H  AAGTTCTTCGTTTTTATATAAGTAAGATGATAGGAATTAGGTGTAA  (SEQ ID NO: 2)
L  TTCAAGAACAAAATATATTCATTCTACTATCCTTAATTCACATT     (SEQ ID NO: 3)

FokI

WT-mtDNA

Δnd4-mtDNA nd4

Δnd4 nd4 mito-nickase (2)

H  ACGAGTTAGAGCATTTCACCCTGTATCCGAAGTTCATTTAGTTC  (SEQ ID NO: 4)
L  TGCTCAATCTCGTAAGTGGGACATAGGCTTCCAAGTAAAATCAG  (SEQ ID NO: 5)

FIG. 1E

*deletion junction sequences*
(deletion size, bps)

1) CACAT*AAGTTCTTGGTTTTAA* — (1244) — AGGCAATTAAAAAACTGTTT (SEQ ID NO:6)

2) CACAT*AAGTTCTTGGTTTTAA* — (1241) — GGCAATTACAAAGCTGTTTA (SEQ ID NO:7)

3) CCTCGGTGAGTGAGGGGGCT — (1553) — GTGGATAAACTTATTGACTC (SEQ ID NO:8)

4) TCATTAAGAGATGTTCTCGG — (1670) — GGCCGCCTTGGGCTCATTCG (SEQ ID NO:9)

5) TCATTAAGAGATGTTCTCGG — (1672) — CCGCCTTGGGCTCATTCGTA (SEQ ID NO:10)

6) *TGTAA*AGTCATTAAGAGATG — (1677) — GGCCGCCTTGGGCTCATTCG (SEQ ID NO:11)

7) *TGTAA*AGTCATTAAGAGATG — (1678) — GCCGCCTTGGGCTCATTCGT (SEQ ID NO:12)

8) ACTCTTCCTCGGTGAGTGAG — (1553) — GGGGCTGTGGATAAACTTAT (SEQ ID NO:13)

9) *CCTTCTAA*AGTCATTAAGAGA — (1679) — GGCCGCCTTGGGCTCATTCG (SEQ ID NO:14)

10) ACAGCATCATTGTAAGTGGG — (2201) — GTTATTAAGTTGATCTCCTC (SEQ ID NO:15)

FIG. 2D

*deletion junction sequences*
(deletion size, bps)

1) GCCCGTAGTTGGCTTGATGTT – (4806) – AGTTGGGTCATTAGCTTCAA (SEQ ID NO:20)

2) GCCCGTAGTTGGCTTGATGTT – (4837) – ATTTTGGTTGGAATAATAGT (SEQ ID NO:21)

3) ATTAGCCCGTAGTTGGCTTGA – (4931) – GGTGGTCGGTAAGCACCAAG (SEQ ID NO:22)

4) TGGTTTAGGCCCAATTGCTAC – (4865) – ATTTTGGTTGGAATAATAGT (SEQ ID NO:23)

5) TGGTTTAGGCCCAATTGCTAC – (4954) – GGGTGGTCGGTAAGCACCAA (SEQ ID NO:24)

6) TTGGTTTAGGCCCAATTGCTA – (5109) – CCCGCAGATTTCAGAGCATT (SEQ ID NO:25)

7) ATGTGGTTGGTTTAGGCCAA – (4961) – GGGTGGTCGGTAAGCACCAA (SEQ ID NO:26)

8) ATGTGGTTGGTTTAGGCCAA – (4962) – GGTGGTCGGTAAGCACCAAG (SEQ ID NO:27)

9) TAAGGGCTATTTTCCCGATG – (5015) – TTGGGTCATTAGCTTCAATG (SEQ ID NO:28)

FIG. 3F

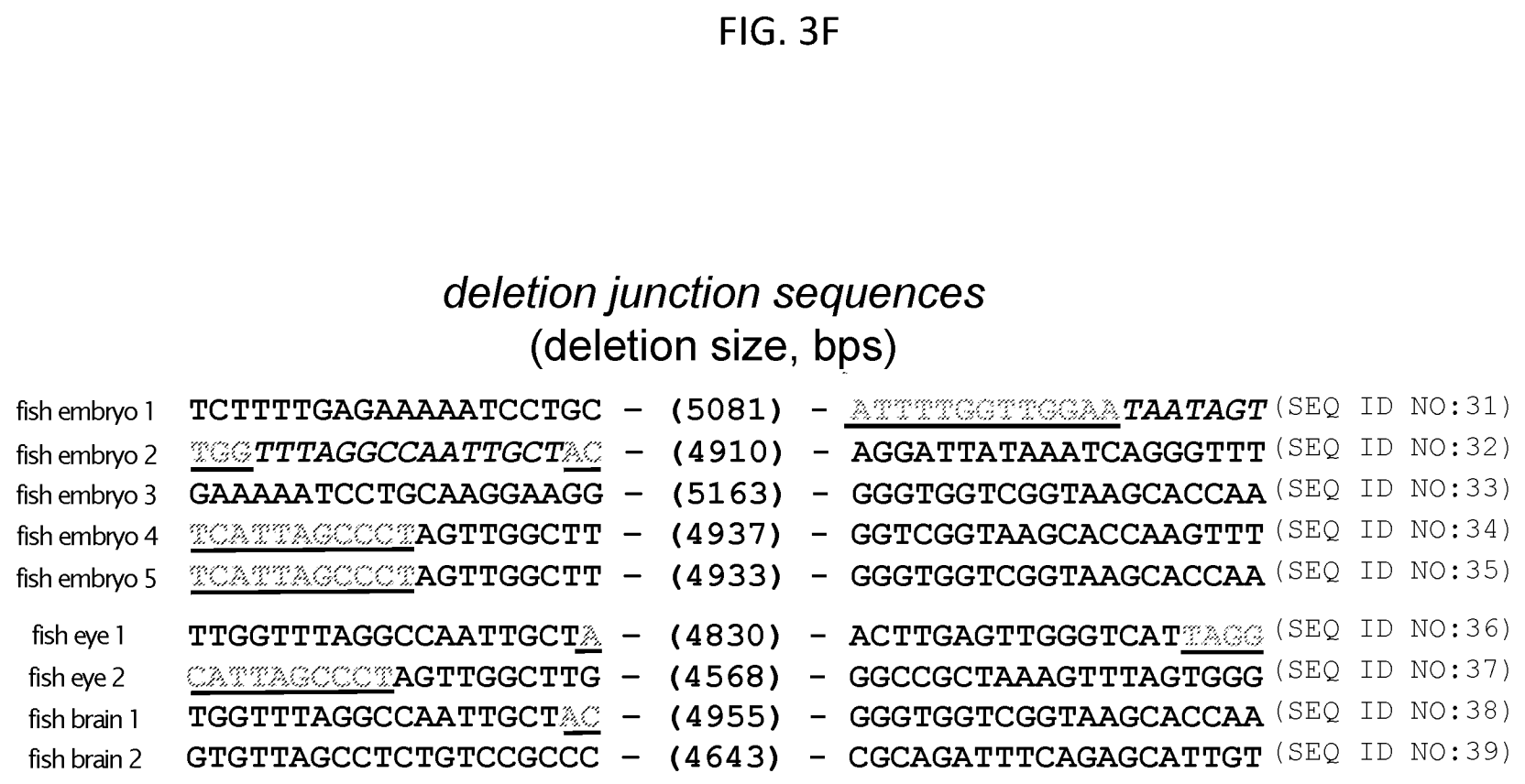

*deletion junction sequences*
*(deletion size, bps)*

| | | | |
|---|---|---|---|
| fish embryo 1 | TCTTTTGAGAAAATCCTGC | — (5081) — | ATTTTGGTTGGAATAATAGT (SEQ ID NO:31) |
| fish embryo 2 | TCGTTTAGGCCAATTGCTAC | — (4910) — | AGGATTATAAATCAGGGTTT (SEQ ID NO:32) |
| fish embryo 3 | GAAAAATCCTGCAAGGAAGG | — (5163) — | GGGTGGTCGGTAAGCACCAA (SEQ ID NO:33) |
| fish embryo 4 | TCATTAGCCCTAGTTGGCTT | — (4937) — | GGTCGGTAAGCACCAAGTTT (SEQ ID NO:34) |
| fish embryo 5 | TCATTAGCCCTAGTTGGCTT | — (4933) — | GGGTGGTCGGTAAGCACCAA (SEQ ID NO:35) |
| fish eye 1 | TTGGTTTAGGCCAATTGCTA | — (4830) — | ACTTGAGTTGGGTCATTAGG (SEQ ID NO:36) |
| fish eye 2 | CATTAGCCCTAGTTGGCTTG | — (4568) — | GGCCGCTAAAGTTTAGTGGG (SEQ ID NO:37) |
| fish brain 1 | TGGTTTAGGCCAATTGCTAC | — (4955) — | GGGTGGTCGGTAAGCACCAA (SEQ ID NO:38) |
| fish brain 2 | GTGTTAGCCTCTGTCCGCCC | — (4643) — | CGCAGATTTCAGAGCATTGT (SEQ ID NO:39) |

1) TTGGTTTAGGCCAATTGCTA — (4830) — ACTTGAGTTGGGGTCAT*TAGG* (SEQ ID NO:36)

2) *AGCCCT*AGTTGGCTTGATGT — (4836) — *TGATTTTGGTTGCAATAATA* (SEQ ID NO:40)

FIG. 3I

*deletion junction sequences*
(deletion size, bps)

1) *CCT*GGGGAAGCCGAGGTTG*AC* – (4806) – CGGGCCCTATTTCAAAGATT (SEQ ID NO:47)
2) TAGTAGTAGTTACTGGTTGA – (4826) – ATAATTTTTTATTTTTATGG (SEQ ID NO:48)

4 mo zebrafish uninjected (female)

Δ*nd5/atp8* mtDNA backbone 4 mo zebrafish injected (male)

Δ*nd5/atp8* mtDNA backbone 4 mo zebrafish uninjected (male)

Δ*nd5/atp8* mtDNA backbone

*Δnd5/atp8* heteroplasmy in eye of adult zebrafish

FIG. 4A

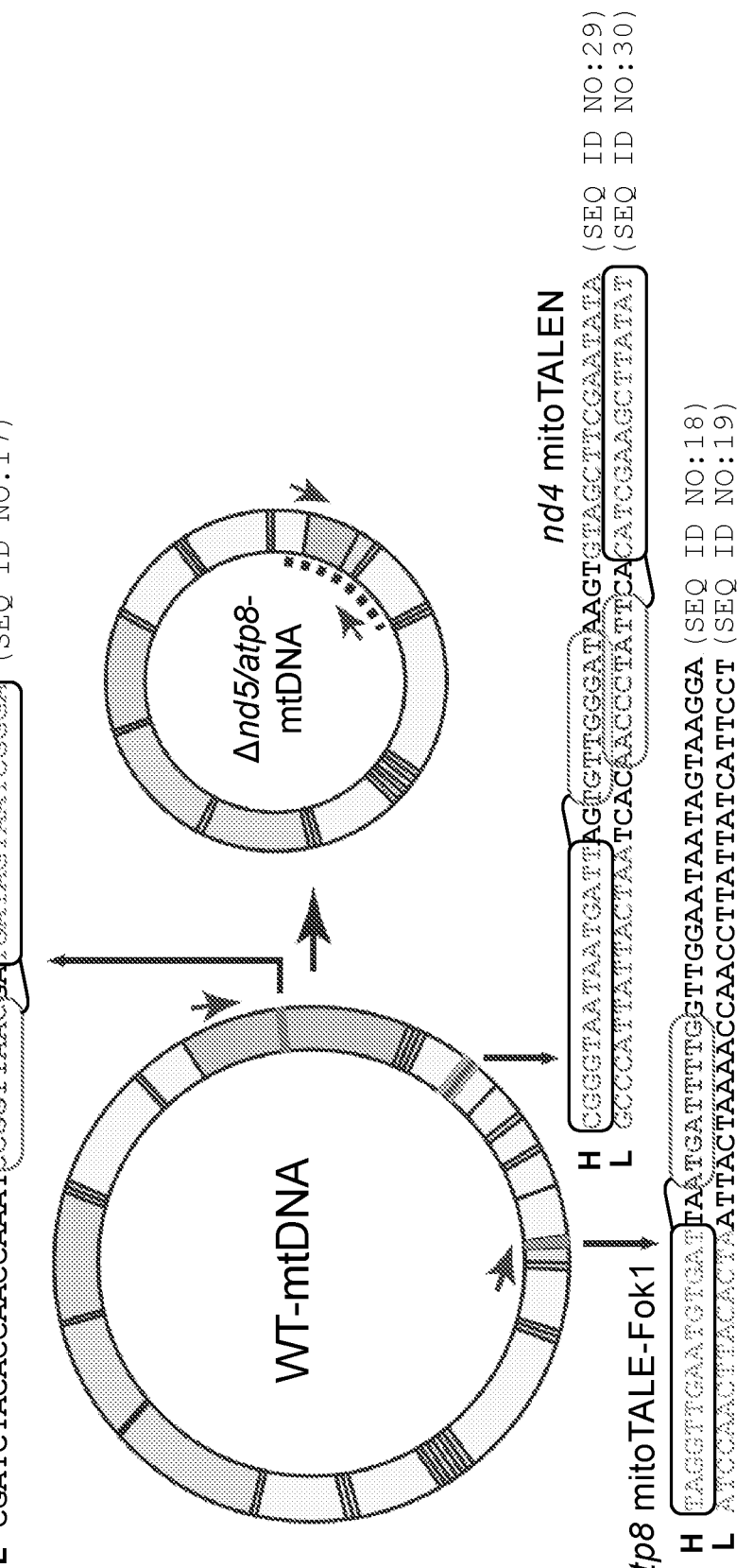

*nd5* mitoTALE-FokI

H  GCTAGATGTGGTTGGTTTAGGCCAATTGCTΛΑϹΛΑΤΤΑΑΤΟΑΤϹϹΤ  (SEQ ID NO:16)
L  CGATCTACACCAACCAAATCGGTTAACGATCΑΤΑGΤΑΑΤϹGGGΑ  (SEQ ID NO:17)

*nd4* mitoTALEN

H  CGGGTAATAATGATTAGTGTTGGGATAAGTGTTAGCTTCCAATATA  (SEQ ID NO:29)
L  ΛϹϹΛΤΤΑΤΤΑϹΤΑΑΤΟΑΟ·ΑΛϹϹΤΑΤΤϹΑΟΑΑΤCGAAGCTTATAT  (SEQ ID NO:30)

*atp8* mitoTALE-Fok1

H  ΤΛGGΤΤGΑΑGΤGΑ·ΤΑΑ·ΤΟΑΤΤΤTGGTTGGAATAATAGTAAGGA  (SEQ ID NO:18)
L  ΛΤϹGΑΛϹΤΤΑϹΑϹ·ΤΑΤΤΑϹΤΑΑΑΑϹCAACCTTATTATTATCATTCCT  (SEQ ID NO:19)

FIG. 4E

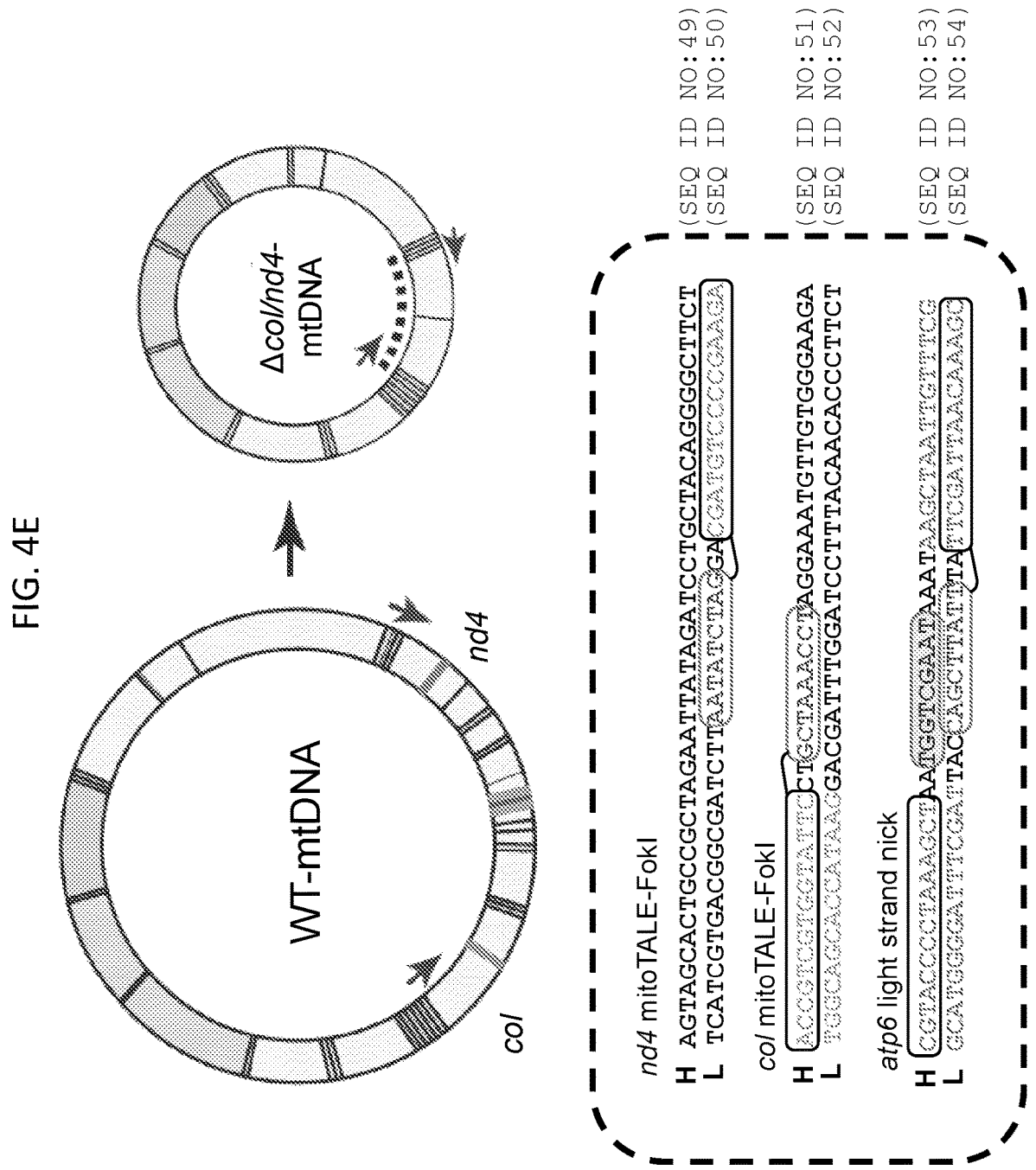

nd4 mitoTALE-FokI
H  AGTAGCACTGCCGCTAGAATTATAGATCCTGCTACAGGGGCTTCT        (SEQ ID NO: 49)
L  TCATCGTGACGGCGATCTTAATATCTAGGACGATGTCCCGGAAGA        (SEQ ID NO: 50)

col mitoTALE-FokI
H  ACGGTCGTATTGCTGCTAAACCTAGGAAAATGTTGTGGGAAGA         (SEQ ID NO: 51)
L  TGGCAGCATAAGGACGATTTGGATCCTTTACAACACCCTTCT         (SEQ ID NO: 52)

atp6 light strand nick
H  CGTACCCCTAAAGCTAATGGTTCGGAATAAATAAGCTAATTGTTTCG     (SEQ ID NO: 53)
L  GCATGGGGATTTCGAATTACCAGCTTTATTTATTCGATTAACTAAAGC    (SEQ ID NO: 54)

MITOCHONDRIAL GENOME EDITING METHODS

STATEMENT AS TO FEDERALLY SPONSORED RESEARCH

This invention was made with government support under GM063904, HG006431, and DK084567 awarded by the National Institutes of Health. The government has certain rights in the invention.

CROSS-REFERENCE TO RELATED APPLICATIONS

This application is a National Stage application under 35 U.S.C. § 371 of International Application No. PCT/US2019/015439, having an International Filing Date of Jan. 28, 2019. The disclosure of the prior application is considered part of the disclosure of this application, and is incorporated in its entirety into this application.

TECHNICAL FIELD

This document relates to materials and methods for making targeted changes to mitochondrial DNA.

BACKGROUND

Mitochondria are a network of critical intracellular organelles with diverse functions ranging from energy production to cell signaling. Mitochondria play a pivotal role in many cellular processes, including ATP production, ion homeostasis, iron-sulfur cluster biogenesis, and cell signaling, and when mitochondria are deficient, divergent and progressive conditions can result (Taylor and Turnbull, *Nat. Rev. Genet.* 6:389-402, 2005; and Vafai and Mootha, *Nature* 491:374-383, 2012). Severe defects in mtDNA can lead to debilitating, incurable disorders.

The mitochondrial genome (mtDNA) consists of 37 genes that support oxidative phosphorylation and are prone to dysfunction that can lead to currently untreatable diseases. Further characterization of mtDNA gene function and creation of more accurate models of human disease will require the ability to engineer precise genomic sequence modifications. To date, however, mtDNA has been inaccessible to direct modification using traditional genome engineering tools due to unique DNA repair contexts in mitochondria (Patananan et al., *Cell Metab.* 23:785-796, 2016).

Manipulation of mtDNA for disease modeling has been largely limited to either random mutagenesis (Tyynismaa and Suomalainen, *EMBO* Reports 10:137-143, 2009; Trifunovic et al., *Nature* 429:417-423, 2004; and Lin et al., *Proc. Natd. Acad. Sci. USA* 109:20065-20070, 2012) or naturally occurring alterations. Moreover, severe mtDNA variants do not readily pass through the germline (Fan et al., *Science* 319:958-962, 2008), making it difficult to develop stable animal models of more severe, physiologically-relevant diseases. Indeed, understanding of this critical organelle in health and disease has been stymied by the inability to precisely manipulate mtDNA de novo.

Editing tools such as transcription activator-like effector (TALE) nucleases and clustered regularly-interspaced short palindromic repeats (CRISPR)-Cas9 rely primarily on double-strand break (DSB) repair in the nuclear genome, where both non-homologous end joining (NHEJ) and homology directed repair (HDR) are active. DSBs can trigger rapid mtDNA degradation, and have been used strategically to combat the deleterious effects of heteroplasmy in patient cells and mouse models of mtDNA disease (Bayona-Bafaluy et al., *Proc. Natl. Acad. Sci. USA* 102:14392-14397, 2005; Alexeyev et al., *Gene Ther* 15:516-523, 2008; Minczuk et al., *Nucleic Acids Res.* 36:3926-3938, 2008; Reddy et al., *Cell* 161:459-469, 2015; and Bacman et al., *Nat. Med.* 19:1111-1113, 2013). Although DSBs can be repaired at low frequencies in mitochondria (Bacman et al., *Nucleic Acids Res.* 37:4218-4226, 2009; Shen et al., *Mutat. Res.* 337:19-23. 1995; and Srivastava and Moraes, *Hum. Mol. Genet.* 14:893-902, 2005), both NHEJ and HDR are very inefficient and have not been useful for mtDNA sequence engineering (Alexeyev et al., *Cold Spring Harb. Perspect. Biol.* 5(5):a012641, 2013, doi: 10.1l01/cshperspect.a012641).

SUMMARY

This document is based, at least in part, on the development of materials and methods for using a "block and nick" DNA modification system to make precise deletions in mtDNA. In studies described elsewhere TALE-nickases have demonstrated the ability to induce targeted mtDNA deletions in vivo (see, e.g., PCT Publication No. WO 2017/015567). A limitation of this approach, however, is the variability of deletion sizes that are generated. The materials and methods provided herein can improve the precision of induced targeted deletions in mtDNA. In fact, it was surprisingly observed, as described herein, that two mitoTALE proteins serving as blocks flanking a single-stranded DNA nick on the light strand of mtDNA were sufficient for deletion induction. This method resulted in deletions that were highly predictable at two different multigenic regions. This "block and nick" protocol was used to create targeted deletions with enhanced deletion precision.

Thus, this document provides a new DNA modification process using sequence-specific TALE proteins to manipulate mtDNA in vitro and in vivo for reverse genetics applications. As described in the Examples below, mtDNA deletions can be induced in *Danio rerio* (zebrafish) using site-directed mitoTALE-nickases. Using this approach, the protein-encoding mtDNA gene nd4 was deleted in injected zebrafish embryos. Further, the DNA engineering system was used to recreate a large deletion spanning from nd5 to atp8, which commonly is found in human diseases such as Kearns-Sayre Syndrome (KSS) and Person Syndrome. Enrichment of mtDNA-deleted genomes was achieved using targeted mitoTALE nucleases by co-delivering mitoTALE-nickases (mito-nickases) and mitoTALE nucleases into zebrafish embryos. This combined approach yielded deletions in over 90% of injected animals, which were maintained through adulthood in various tissues. Subsequently, it was confirmed that large, targeted deletions could be induced with this approach in human cells. In addition, when provided with a single nick on the mtDNA light-strand, the binding of a terminal TALE protein alone at the intended recombination site was sufficient for deletion induction. This "block and nick" approach yielded engineered mitochondrial molecules with single nucleotide precision at two different targeted deletion sites. In conjunction with heteroplasmy stimulation from matched nucleases, this precise seeding method to engineer mtDNA variants is a critical step for the exploration of mtDNA function, and for creating new animal models of mitochondrial disease.

In a first aspect, this document features a method for editing mtDNA within a cell. The method can include introducing into the cell (a) a DNA cleaving enzyme targeted to the mtDNA sequence to be deleted; (b) a first DNA binding component targeted to a sequence adjacent to the 5' end of a mtDNA sequence to be deleted; and (c) a second DNA binding component targeted to a sequence adjacent to the 3' end of the mtDNA sequence to be deleted, where the DNA cleaving enzyme generates a double stranded break (DSB) within the mtDNA sequence to be deleted or generates a single strand nick on the light strand of the mtDNA sequence to be deleted, and wherein the mtDNA sequence between the target sequence for the first DNA binding component and the target sequence for the second DNA binding component is deleted. The DNA cleaving enzyme can be a dimeric nuclease containing a pair of monomers, where each monomer includes (a) a first portion containing a mitochondrial targeting sequence (MTS); (b) a second portion containing an amino acid sequence targeting the monomer to the mtDNA sequence to be deleted; and (c) a third portion containing a nuclease domain, wherein, when the monomers are bound to their target sequences within the mtDNA sequence to be deleted, the nuclease domains of the monomers form a dimer that cleaves the mtDNA sequence to be deleted. The nuclease domain can be a FokI endonuclease domain. The DNA cleaving enzyme can be a dimeric nickase containing a pair of monomers, where each monomer includes (a) a first portion containing a MTS; (b) a second portion containing an amino acid sequence targeting the DNA cleaving enzyme to the sequence to be deleted from the mtDNA; and (c) a third portion containing a nuclease domain, where one monomer of the pair includes an unmodified nuclease domain and the other monomer of the pair includes a modified nuclease domain, wherein, when the monomers are bound to their target sequences within the mtDNA sequence to be deleted, the nuclease domains of the monomers form a dimer that nicks the light strand of the mtDNA sequence to be deleted. The unmodified nuclease domain can include a FokI endonuclease domain, and the modified nuclease domain can include a modified FokI endonuclease domain. The modified FokI endonuclease domain can include an aspartic acid to alanine substitution at the amino acid position corresponding to position 450 of an unmodified FokI endonuclease domain. The FokI endonuclease domain can have the sequence set forth in SEQ ID NO:108. The MTS in each monomer can be from an isocitrate dehydrogenase 2 gene. The MTS in each monomer can include the sequence set forth in SEQ ID NO:1. The second portion of each monomer can include a transcriptional activator-like effector (TALE) backbone and a plurality of tandem repeat sequences containing repeat variable dinucleotides (RVDs) that, in combination, bind to a target sequence within the mtDNA sequence to be deleted.

In some cases, the first DNA binding component can be a dimer containing a pair of monomers, where each monomer is a polypeptide that includes (i) a first portion containing a MTS, (ii) a second portion containing an amino acid sequence targeting the monomer to a sequence adjacent to the 5' end of the mtDNA sequence to be deleted, and (iii) a third portion containing a nuclease domain, where one monomer of the pair includes an unmodified nuclease domain and the other monomer of the pair includes a modified nuclease domain; and the second DNA binding component can be a dimer containing a pair of monomers, where each monomer is a polypeptide that includes (i) a first portion containing a MTS, (ii) a second portion containing an amino acid sequence targeting the monomer to the sequence adjacent to the 3' end of the mtDNA sequence to be deleted, and (iii) a third portion containing a nuclease domain, wherein one monomer of the pair includes an unmodified nuclease domain and the other monomer of the pair includes a modified nuclease domain. The MTS in each monomer of the first and second DNA binding components can be from an isocitrate dehydrogenase 2 gene. The MTS in each monomer of the first and second DNA binding components can include the sequence set forth in SEQ ID NO:1. The second portion of each monomer of the first DNA binding component can include a TALE backbone and a plurality of tandem repeat sequences containing RVDs that, in combination, bind to target sequences adjacent to the 5' end of the mtDNA sequence to be deleted, and the second portion of each monomer of the second DNA binding component can include a TALE backbone and a plurality of tandem repeat sequences containing RVDs that, in combination, bind to target sequences adjacent to the 3' end of the mtDNA sequence to be deleted. The unmodified nuclease domain within the third portion of the first and second DNA binding components can be a FokI endonuclease domain, and the modified nuclease domain within the third portion of the first and second DNA binding components can be a modified FokI endonuclease domain. The modified FokI endonuclease domain can include an aspartic acid to alanine substitution at the amino acid position corresponding to position 450 of an unmodified FokI endonuclease domain. When the monomers of the first and second DNA binding components are bound to their target sequences adjacent to the 5' and 3' ends of the mtDNA sequence to be deleted, the monomers can form dimers that generate single strand nicks in the mtDNA. The modified FokI endonuclease domain can include an aspartic acid to alanine substitution at the amino acid position corresponding to position 483 of an unmodified FokI endonuclease, and an arginine substitution to alanine substitution at the amino acid position corresponding to position 487 of an unmodified FokI endonuclease.

In some cases, the first DNA binding component can be a polypeptide that includes (i) a first portion containing a MTS, and (ii) a second portion containing an amino acid sequence targeting the first DNA binding component to the sequence adjacent to the 5' end of the mtDNA sequence to be deleted, where the first DNA binding component lacks a nuclease domain; and the second DNA binding component can be a polypeptide that includes (i) a first portion containing a MTS, and (ii) a second portion containing an amino acid sequence targeting the second DNA binding component to the sequence adjacent to the 3' end of the mtDNA sequence to be deleted, where the second DNA binding component lacks a nuclease domain. The MTS in the first and second DNA binding components can be from an isocitrate dehydrogenase 2 gene. The MTS in the first and second DNA binding components can include the sequence set forth in SEQ ID NO:1. The second portion of the first DNA binding component can include a TALE backbone and a plurality of tandem repeat sequences containing RVDs that, in combination, bind to a target sequence adjacent to the 5' end of the mtDNA sequence to be deleted, and the second portion of the second DNA binding component can include a TALE backbone and a plurality of tandem repeat sequences containing RVDs that, in combination, bind to a target sequence adjacent to the 3' end of the mtDNA sequence to be deleted.

In some cases, the first DNA binding component can be a dimer containing a pair of monomers, wherein each monomer is a polypeptide that includes (i) a first portion containing a MTS, (ii) a second portion containing an amino acid sequence targeting the monomer to a sequence adjacent to the 5' end of the mtDNA sequence to be deleted, and (iii) a third portion containing a nuclease domain, where one monomer of the pair includes an unmodified nuclease domain and the other monomer of the pair includes a modified nuclease domain; and the second DNA binding component can be a polypeptide that includes (i) a first portion containing a MTS, and (ii) a second portion containing an amino acid sequence targeting the second DNA binding component to the sequence adjacent to the 3' end of the mtDNA sequence to be deleted, where the second DNA binding component lacks a nuclease domain. The MTS in each monomer of the first and second DNA binding components can be from an isocitrate dehydrogenase 2 gene. The MTS in each monomer of the first and second DNA binding components can include the sequence set forth in SEQ ID NO:1. The second portion of each monomer of the first DNA binding component can include a TALE backbone and a plurality of tandem repeat sequences containing RVDs that, in combination, bind to target sequences adjacent to the 5' end of the mtDNA sequence to be deleted, and the second portion of each monomer of the second DNA binding component can include a TALE backbone and a plurality of tandem repeat sequences containing RVDs that, in combination, bind to target sequences adjacent to the 3' end of the mtDNA sequence to be deleted. The unmodified nuclease domain within the third portion of the first DNA binding component can be a FokI endonuclease domain, and the modified nuclease domain within the third portion of the first DNA binding component can be a modified FokI endonuclease domain. The modified FokI endonuclease domain can include an aspartic acid to alanine substitution at the amino acid position corresponding to position 450 of an unmodified FokI endonuclease domain. When the monomers of the first DNA binding component are bound to their target sequences adjacent to the 5' end of the mtDNA sequence to be deleted, the monomers can form a dimer that generates a single strand nick in the mtDNA. The modified FokI endonuclease domain can include an aspartic acid to alanine substitution at the amino acid position corresponding to position 483 of an unmodified FokI endonuclease, and an arginine substitution to alanine substitution at the amino acid position corresponding to position 487 of an unmodified FokI endonuclease.

In some cases, the first DNA binding component can be a polypeptide that includes (i) a first portion containing a MTS, and (ii) a second portion containing an amino acid sequence targeting the first DNA binding component to the sequence adjacent to the 5' end of the mtDNA sequence to be deleted, where the first DNA binding component lacks a nuclease domain; and the second DNA binding component can be a dimer containing a pair of monomers, wherein each monomer is a polypeptide that includes (i) a first portion containing a MTS, (ii) a second portion containing an amino acid sequence targeting the monomer to a sequence adjacent to the 3' end of the mtDNA sequence to be deleted, and (iii) a third portion containing a nuclease domain, where one monomer of the pair includes an unmodified nuclease domain and the other monomer of the pair includes a modified nuclease domain. The MTS in each monomer of the first and second DNA binding components can be from an isocitrate dehydrogenase 2 gene. The MTS in each monomer of the first and second DNA binding components can include the sequence set forth in SEQ ID NO:1. The second portion of each monomer of the first DNA binding component can include a TALE backbone and a plurality of tandem repeat sequences containing RVDs that, in combination, bind to target sequences adjacent to the 5' end of the mtDNA sequence to be deleted, and the second portion of each monomer of the second DNA binding component can include a TALE backbone and a plurality of tandem repeat sequences containing RVDs that, in combination, bind to target sequences adjacent to the 3' end of the mtDNA sequence to be deleted. The unmodified nuclease domain within the third portion of the second DNA binding component can be a FokI endonuclease domain, and the modified nuclease domain within the third portion of the second DNA binding component can be a modified FokI endonuclease domain. The modified FokI endonuclease domain can include an aspartic acid to alanine substitution at the amino acid position corresponding to position 450 of an unmodified FokI endonuclease domain. When the monomers of the second DNA binding component are bound to their target sequences adjacent to the 3' end of the mtDNA sequence to be deleted, the monomers can form a dimer that generates a single strand nick in the mtDNA. The modified FokI endonuclease domain can include an aspartic acid to alanine substitution at the amino acid position corresponding to position 483 of an unmodified FokI endonuclease, and an arginine substitution to alanine substitution at the amino acid position corresponding to position 487 of an unmodified FokI endonuclease.

In any of the above cases, the cell can be a eukaryotic cell. The eukaryotic cell can be within a eukaryotic organism. The introducing can include injecting the DNA cleaving enzyme and the first and second DNA binding components into the eukaryotic organism. The introducing can include injecting nucleic acid molecules encoding the DNA cleaving enzyme and the first and second DNA binding components into the eukaryotic organism.

In any of the above cases, the cell can be in vitro. The introducing can include transforming nucleic acid molecules encoding the DNA cleaving enzyme and the first and second DNA binding components into the cell.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

Figure 1A:
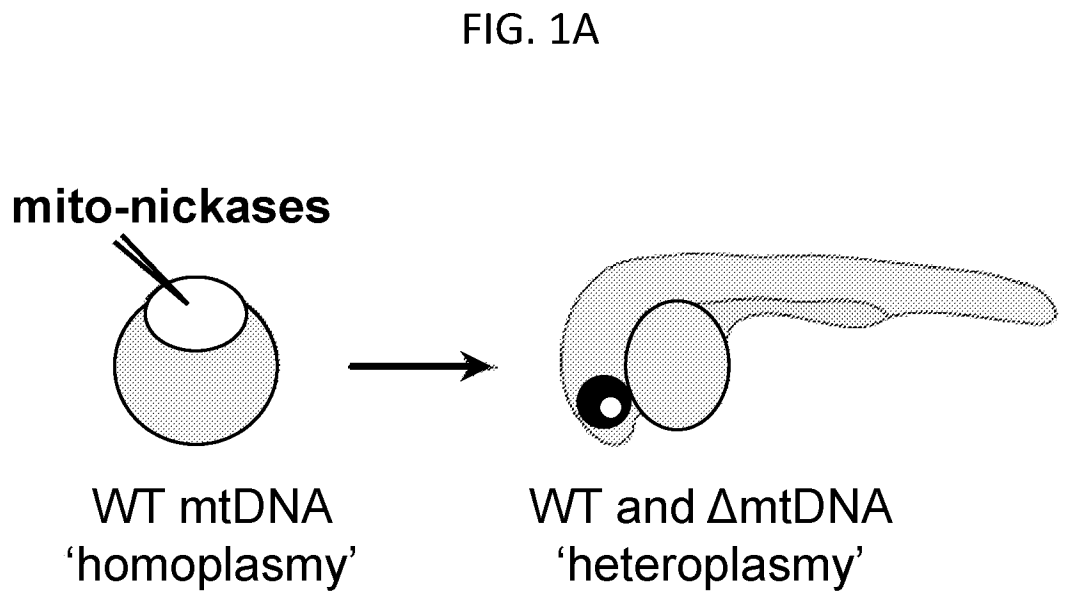

FIGS. 1A-1E depict single-gene deletion of nd4 using mito-nickases. FIG. 1A is a schematic of mtDNA sequence manipulation using mito-nickases in zebrafish.

FIG. 1B is a diagram depicting the method. Mito-nickases were targeted inside the border of nd4, with TALE binding and FokI activity on either the heavy (H) or light (L) strand. The active FokI is shown on the light strand while the catalytically inactive variant, dead FokI (indicated in the figure as dFokI), is on the heavy strand. Deletions were detected using PCR, with primers positioned outside of both nick sites (arrows). The expected PCR product is indicated by the dashed line. FIG. 1C is an image showing that deletion of nd4 was detected using PCR in animals injected with nd4 mito-nickases. Every row in FIG. 1C contains samples from 8 individual animals per condition. FIG. 1D is a schematic of the mtDNA region surrounding nd4, with locations of deletions shown as black bars. Positions of the nd4 mito-nickase (1) and the nd4 mito-nickase (2) are indicated by brackets. FIG. 1E shows the deletion junction sequences, with the size of deletion in parentheses. Underlined sequences indicate the nd4 mito-nickase (1) binding sites.

FIGS. 2A-2D depict multigenic deletion molecularly modeling the "common deletion" using mito-nickases. FIG. 2A is a diagram showing that in this method, mitonickases were targeted to nd5 and atp8, with TALE binding and FokI activity on either the heavy (H) or light (L) strand. The active FokI is on the light strand while the catalytically inactive variant, dFokI, is on the heavy strand. Deletions were detected using PCR with primers positioned outside of both nick sites (arrows). The expected PCR product is indicated by a dashed line. FIG. 2B is an image showing detection of deletions in animals injected with nd5 and atp8 mito-nickases. Each row contains samples from 8 individual animals per condition. FIG. 2C is a schematic of the regions around the nd5 and atp8 mito-nickase binding sites. Black bars indicate deletion regions. All mtDNA between atp6 and nd5 is deleted. Relative locations of the nd5 mito-nickase and the atp8 mito-nickase are indicated by brackets. FIG. 2D shows deletion junction sequences with the size of each deletion indicated in parentheses. In the left sequence panel, underlined sequences indicate the nd5 mito-nickase binding sites and the italicized sequences indicate the intervening spacer region. In the right sequence panel, underlined sequences indicate the atp8 mito-nickase binding sites and the italicized sequence indicates the intervening spacer region.

FIGS. 3A-3K depict expanding nickase-induced mtDNA deletions using a targeted mitoTALE nuclease (mito-TALEN). FIG. 3A is a schematic showing mitoTALE nuclease targeting. A mitoTALE nuclease targeting nd4 was designed to selectively bind and cut the WT-mtDNA genome. The sequences targeted by the nd5 and atp8 mito-nickases are in the dotted box. FIG. 3B is an image showing detection of mtDNA deletions in injected zebrafish embryos. Each row contains samples from 8 individual animals per condition. FIG. 3C is an image showing detection of mtDNA deletions in the organs of a four-month-old female zebrafish. H=heart, I/L=intestine/liver, O=ovaries, E=eyes, B=brain, M=Skeletal muscle. FIG. 3D is an image showing detection of mtDNA deletions in transfected human cells (293T cell line). FIG. 3E is a schematic of the deleted regions around the nd5 and atp8 nickase binding sites. Black bars indicate deletion locations of mtDNA after editing by mito-nickases and mitoTALE nucleases in zebrafish embryos, adult tissue, and human cells. All mtDNA between atp6 and nd5 is deleted. The relative locations of the nd5 mito-nickase and the atp8 mito-nickase are indicated by brackets. NTC=no template control. FIG. 3F shows sequences of deletion junctions corresponding to FIG. 3E. In the left sequence panel, underlined sequences are the nd5 nickase binding sites and the italicized sequence is the intervening spacer. In the right sequence panel, underlined sequences are the atp8 nickase binding sites and the italicized sequence is the intervening spacer. FIG. 3G shows mtDNA deletions from fin biopsies of two four-month-old zebrafish (one male, one female), together with a schematic of the deleted regions around the nd5 and atp8 nickase binding sites. Black bars indicate deletion locations of mtDNA after editing by mitoTALE-nickases and mitoTALE nucleases in zebrafish embryos, adult tissue, and human cells. All mtDNA between atp6 and nd5 is deleted. Relative locations of the nd5 nickase and the atp8 nickase are indicated by brackets. FIGS. 3H and 3I show targeted mtDNA deletions in human cells to molecularly model the common deletion. FIG. 3H is a schematic showing mito-nickase and mitoTALE nuclease targeting. A mitoTALE nuclease targeting ND4 was designed to selectively bind and cut the WT-mtDNA genome. The sequences targeted for the ND5 and ATP8 nickases are in the dotted box. FIG. 3I shows the deletion junction sequences from the schematic in FIG. 3E. In the left sequence panel, underlined sequences are the nd5 nickase binding sites and the italicized sequence is the intervening spacer. FIGS. 3J and 3K show targeted mtDNA deletions in four-month-old zebrafish. FIG. 3J is a series of images showing detection of nd5 to atp8 mtDNA deletions in various organs of zebrafish injected with the nd5 and atp8 mito-nickases and the nd4 mito-TALE-nuclease shown in FIG. 3A. NTC=no template control. FIG. 3K is a graph plotting heteroplasmy levels in the eyes of zebrafish injected with and without the mito-nickases and mitoTALE nuclease (one male and one female from each group). The mean is shown by a horizontal bar.

FIGS. 4A-4I demonstrate that the "block and nick" strategy described herein generates highly predictable mtDNA deletions. FIG. 4A is a schematic showing mitoTALE arms (mitoTALE-FokI) positioned at nd5 and atp8 and a mito-TALE nuclease positioned on nd4. FIG. 4B is an image showing detection of mtDNA deletions in zebrafish embryos injected with nd5 and atp8 mitoTALE-FokI with variable nd4 heavy (H) and light (L) strand breaks. FIG. 4C is an image showing detection of mtDNA deletions across two different multigenic regions, atp8 to nd5 and nd4 to coI, using terminal mitoTALE-FokI binding and light strand nicking in-between. FIG. 4D is a pair of graphs plotting quantification of AmtDNA heteroplasmy of zebrafish embryos across the indicated multigenic regions. The median is shown by a horizontal bar. *=p<0.05. FIGS. 4E and 4F show zebrafish nd4 to coI deletions made using the "block and nick" strategy. FIG. 4E is a schematic showing single TALE arms (mitoTALE-FokI) positioned at nd4 and coI and a mitoTALE-nickase cutting the light strand positioned on nd6. TALE binding sequences are shown in the dotted box. FIG. 4F is a schematic of the deleted regions around the nd4 and coI mitoTALE-FokI binding sites. Black bars indicate deletion locations of mtDNA deletions after mitoTALE-FokI and light strand injections in zebrafish embryos. All mtDNA between coII and coIII is deleted. Relative locations of the nd4 mitoTALE-FokI and the coI mitoTALE-FokI are indicated by arrows. Deletion sizes are in parentheses, and additional single nucleotide deletions are shown with a colon (:). FIG. 4G is a schematic showing the deleted regions around the nd5 and atp8 mitoTALE-FokI binding sites. Black bars indicate deletion locations of mtDNA deletions after mitoTALE-FokI and light strand nicking in zebrafish embryos. All mtDNA between nd5 and atp6 is deleted. Relative locations of the nd5 mitoTALE-FokI and atp8 mitoTALE-FokI are indicated by brackets. Deletion sizes are in parentheses, and additional single nucleotide deletions are shown with a colon (:). FIG. 4H is an image showing detection of mtDNA deletions in zebrafish after inhibiting either cutting (D450A amino acid substitution) or dimerization (p.D483A, p.R487A) of the terminal mitoTALE-FokI constructs. FIG. 4I is a schematic of molecular components involved in "block and nick" mtDNA editing. Each row in FIGS. 4B, 4C, and 4H contains samples from 8 individual animals per condition.

DETAILED DESCRIPTION

Figure 1C:
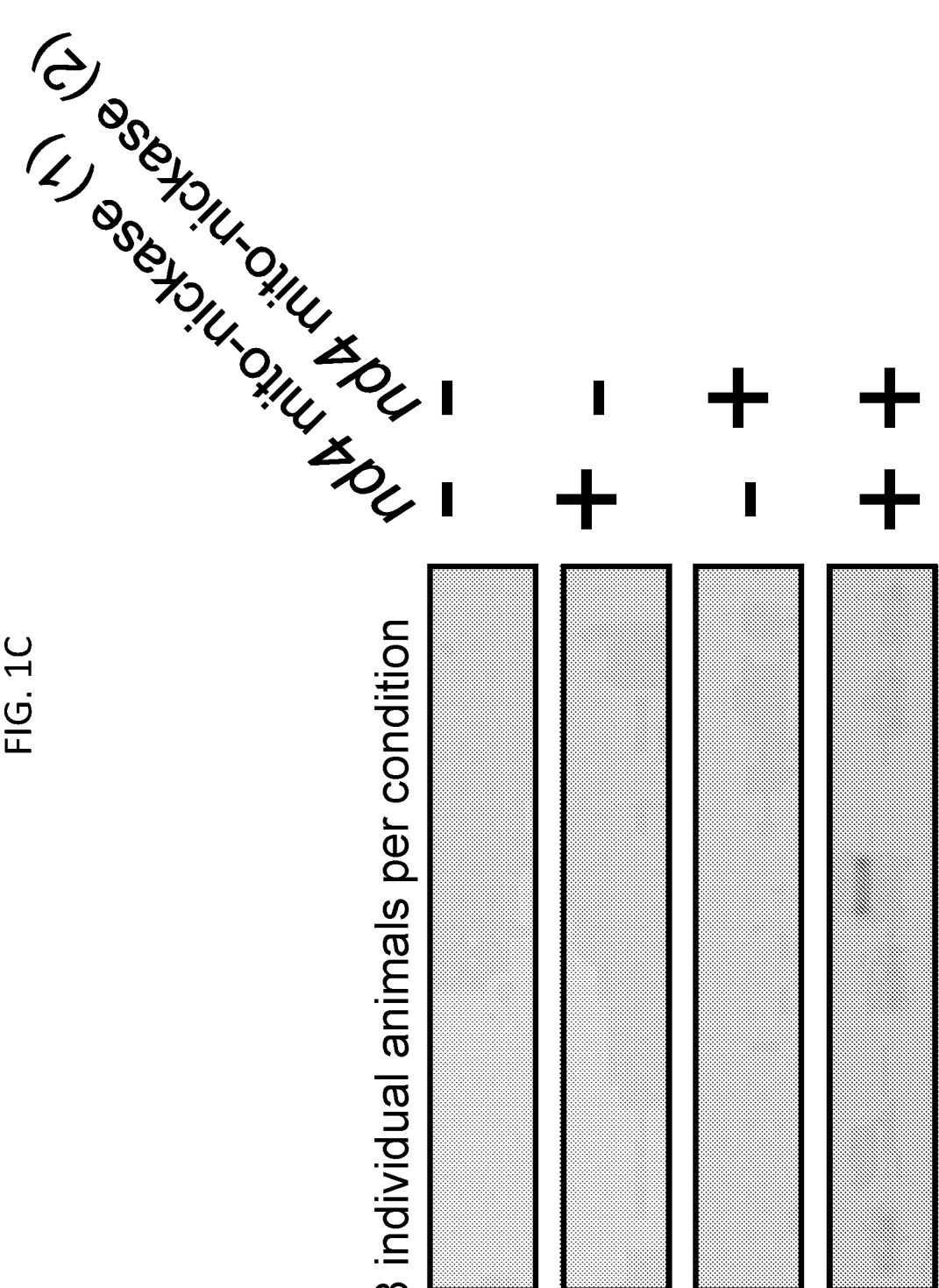

The mitochondrial genome contains double-stranded DNA, but differs from the nuclear genome in that it is circular and much smaller, containing only about 16,500 base pairs that include 37 genes encoding 13 proteins, 22 tRNAs, and 2 rRNAs. Mitochondrial RNAs are transcribed as long polycistronic precursor transcripts from both strands (typically termed "heavy" and "light") that are processed by excision of 22 interspersed tRNAs to concomitantly release individual rRNAs and mRNAs (Ojala et al., *Nature* 290: 470-474, 1981). Only about three percent of the mitochondrial genome is noncoding DNA. All mitochondrially encoded proteins instruct cells to produce subunits of the enzyme complexes of the oxidative phosphorylation system. Each cell contains numerous mitochondria, and each mitochondrion contains dozens of copies of the mitochondrial genome. The mitochondrial genome has a mutation rate that is about 100-fold higher than the nuclear genome, which leads to a heterogeneous population of mitochondrial DNA within the same cell (referred to as "heteroplasmy").

Mutations in mtDNA are thought to be associated with numerous clinical disorders. In adults, these include neurological diseases (e.g., migraine, strokes, epilepsy, dementia, myopathy, peripheral neuropathy, diplopia, ataxia, speech disturbances, and sensorineural deafness), gastrointestinal diseases (e.g., constipation, irritable bowel, and dysphagia), cardiac diseases (e.g., heart failure, heart block, and cardiomyopathy), respiratory diseases (e.g., respiratory failure, nocturnal hypoventilation, recurrent aspiration, and pneumonia), endocrine diseases (e.g., diabetes, thyroid disease, parathyroid disease, and ovarian failure), ophthalmological diseases (e.g., optic atrophy, cataract, ophthalmoplegia, and ptosis). In children, disorders thought to be associated with mtDNA mutations include neurological diseases (e.g., epilepsy, myopathy, psychomotor retardation, ataxia, spasticity, dystonia, and sensorineural deafness), gastrointestinal diseases (e.g., vomiting, failure to thrive, and dysphagia), cardiac diseases (e.g., biventricular hypertrophic cardiomyopathy and rhythm abnormalities), respiratory diseases (e.g., central hypoventilation and apnea), hematological diseases (e.g., anemia and pancytopenia), renal diseases (e.g., renal tubular defects), liver diseases (e.g., hepatic failure), endocrine diseases (e.g., diabetes and adrenal failure), and ophthalmological diseases (e.g., optic atrophy). By targeting mtDNA mutations to particular sequences, such clinical conditions can be modeled in experimental systems. For example, zebrafish are a premier teleostean model system, with strong biological and genomic similarities to other vertebrates, and can be useful for studying human biology and disease using in vivo genetic and molecular tools, including those described herein.

This document provides materials and methods for manipulating (e.g., modifying, such as through targeted deletions) mtDNA. Studying how changes in mtDNA affect eukaryotic systems can be difficult, because there are limited options for manipulating the mtDNA genome. This document discloses that deletions in the mtDNA genome can be induced, in some embodiments, using a modified TALE-nuclease system targeting the mitochondrial genome. The TALE-nuclease system can include a heterodimer of a normal and an attenuated form of GoldyTALE-nuclease linked to a mitochondrial targeting sequence, referred to herein as an a-mitoTALE nuclease or a mitoTALE nickase, depending on the particular attenuated GoldyTALE-nuclease member of the heterodimer. In some embodiments, this site-directed, heterodimeric nuclease system can be targeted to the mitochondrial matrix, where the mtDNA resides submitochondrially. As described in the Examples herein, deletions at selected locations and having reproducible size were successfully generated in vitro in human cell culture, and also in vivo in *Danio rerio* (zebrafish). The deletions were stable and detectable by PCR, and sequencing revealed that the amplicons match human and zebrafish mitochondrial DNA (respectively), with specific deletions.

The methods provided herein can be used, for example, as research tools for individualized medicine—to make cellular and/or animal avatars of patients with mitochondrial DNA deletions. In addition, this approach can have other applications, especially in mitochondrial research.

The materials and methods provided herein can be used to introduce genetic changes precisely at endonuclease cut sites in vitro or in vivo. For example, in some embodiments, the methods can be used to introduce deletions into particular mitochondrial genes, in order to mimic clinical disorders characterized by mutations in those genes. In some cases, one or more genes may be deleted. The genetic changes can be induced using chimeric DNA nickase polypeptides that include (a) a mitochondrial target sequence directing the chimeric molecules to mitochondria, (b) a region designed to target the molecules to specific DNA sequences within the mitochondria, and (c) a nuclease that generates a double or single strand cut in the mitochondrial DNA at or near the selected target sequence.

Suitable mitochondrial target sequences include, for example, the mitochondrial targeting sequence (MTS) associated with the isocitrate dehydrogenase 2 protein, as well as the human COX8A MTS, human SOD2 MTS. Other useful targeting sequences include those described elsewhere (see, for example, Claros and Vincens, *Eur. J. Biochem.* 241:779-786, 1996).

In some embodiments, the region of the chimeric nuclease polypeptide that targets the molecule to a particular DNA sequence can include a sequence from a TALE polypeptide. Alternatively, the region targeting the chimeric DNA nuclease to a selected sequence can be from a zinc finger protein (e.g., a zinc finger DNA binding domain derived from the mouse transcription factor Zif268; Porteus and Baltimore, *Science* 300:763, 2003) or a meganuclease (e.g., a wild type or variant homing endonuclease, such as a meganuclease belonging to the dodecapeptide family (LAGLIDADG; SEQ ID NO:112; see, WO 2004/067736). Another option for mtDNA targeting includes the use of Clustered Regularly Interspersed Short Palindromic Repeats (CRISPR)/CRISPR-associated system (Cas) technology (Patananan et al., supra; and Gammage et al., *Trends Genet.* 2017, doi: 10.1016/j.tig. 2017.11.001). TALE proteins are traditionally more difficult to assemble than CRISPR/Cas9, but single-reaction synthesis technology makes TALEs accessible for genome engineering applications (Ma et al., *Hum. Gene Ther.* 27:451-463, 2016). Importantly, TALE use in mtDNA engineering only requires a single mitochondrial targeting sequence, such as SEQ ID NO:1, which was developed from an in vivo protein trapping method (Clark et al., *Nat. Methods* 8:506-515, 2011) on the reasoning that a nickase-induced single-strand break approach could generate targeted deletions of various sizes in mtDNA by avoiding DSBs (Kim et al., *Genome Res.* 22:1327-1333, 2012).

In some embodiments, DNA targeting sequences derived from TALEs can be used. TALEs are polypeptides of plant pathogenic bacteria that are injected by the pathogen into the plant cell, where they travel to the nucleus and function as transcription factors to turn on specific plant genes (see, e.g., Gu et al., *Nature* 435:1122, 2005; Yang et al., *Proc. Natl. Acad. Sci. USA* 103:10503, 2006; Kay et al., *Science* 318: 648, 2007; Sugio et al., *Proc. Natl. Acad. Sci. USA* 104: 10720, 2007; and Römer et al., *Science* 318:645, 2007). Specificity depends on an effector-variable number of imperfect, typically 34 amino acid repeats (Schornack et al., *J Plant Physiol.* 163:256, 2006). Polymorphisms are present primarily at repeat positions 12 and 13, which are referred to as the repeat variable-diresidue (RVD). Interestingly, the RVDs of TALEs correspond to the nucleotides in their target sites in a direct, linear fashion, one RVD to one nucleotide, with some degeneracy and no apparent context dependence. For example, a His-Asp RVD can bind to cytosine, an Asn-Asn RVD can bind to guanine, an Asn-Ile RVD can bind to adenosine, and an Asn-Gly RVD can bind to thymine. Since the primary amino acid sequence of a TALE dictates the nucleotide sequence to which it binds, target sites can be predicted for TALEs, and TALEs also can be engineered and generated for the purpose of binding to particular nucleotide sequences.

Further, by linking a TALE to an endonuclease, a sequence-specific TALE-nuclease can be designed and generated to recognize a preselected target nucleotide sequence present in a cell. In some cases, a target nucleotide sequence can be scanned for nuclease recognition sites, and a particular nuclease can be selected based on the target sequence. Conversely, TALE-nucleases can be engineered to target a particular cellular (e.g., mtDNA) sequence. A nucleotide sequence encoding a desired TALE-nuclease can be inserted into any suitable expression vector, and can be operably linked to one or more promoters or other expression control sequences, as described further below.

Examples and further descriptions of TALE-nucleases can be found, for example, in U.S. Pat. No. 8,586,363, which is incorporated herein by reference in its entirety. In some cases, a TALE-nuclease can have truncations at the N- and/or C-terminal regions of the TAL portion of the polypeptide, such that it has a shortened scaffold as compared to a wild type TAL polypeptide. An exemplary TALE-nuclease with a modified scaffold is the +63 TALE-nuclease described, for example, in PCT Publication No. WO 2013/191769, which is incorporated herein by reference in its entirety. It is to be noted that the TAL portion also can include one or more additional variations (e.g., substitutions, deletions, or additions) in combination with such N- and C-terminal scaffold truncations. For example, a TALE-nuclease can have N- and C-terminal truncations of the TAL portion in combination with one or more amino acid substitutions (e.g., within the scaffold and/or within the repeat region).

In general, for mitoTALE nuclease polypeptides, a TALE sequence can be fused to a mitochondrial targeting sequence (e.g., SEQ ID NO: 1), and also to a nuclease or a portion of a nuclease, such as a nonspecific cleavage domain from a type II restriction endonuclease (e.g., FokI; Kim et al., *Proc. Natl. Acad. Sci. USA,* 93:1156-1160, 1996). Other useful endonucleases may include, for example, HhaI, HindIII, Notd, BbvCI, EcoRI, BglI, and AlwI. In some cases, the fact that some endonucleases (e.g., FokI) function as dimers (Bitinaite et al., *Proc. Natl Acad. Sci. USA* 95:10570-10575, 1998) can be capitalized upon to enhance the target specificity of the TALE. For example, in some cases, separate FokI monomers can be fused to TALE sequences that recognize different DNA target sequences, and only when the two recognition sites are in close proximity do the inactive monomers come together to create a functional enzyme. By requiring DNA binding to activate the nuclease, a highly site-specific restriction enzyme can be created. In some embodiments, however, monomeric TALE-nucleases can be constructed, such that single TALEs are fused to a nuclease that does not require dimerization to function. One such nuclease, is a single-chain variant of FokI in which the two monomers are expressed as a single polypeptide (see, Minczuk et al., *Nucleic Acids Res.* 36:3926-3938, 2008).

A representative amino acid sequence for a FokI cleavage domain is set forth in SEQ ID NO:108. The residues at the positions corresponding to positions 450, 483, and 487 of a full length FokI endonuclease are underlined and in bold font. A representative nucleotide sequence encoding the FokI amino acid sequence of SEQ ID NO:108 is set forth in SEQ ID NO:109.

```
                                       (SEQ ID NO: 108)
LVKSELEEKKSELRHKLKYVPHEYIELIEIARNSTQDRILEMKVMEFFMKV

YGYRGKHLGGSRKPDGAIYTVGSPIDYGVIVDTKAYSGGYNLPIGQADEMQ

RYVEENQTRNKHINPNEWWKVYPSSVTEFKFLFVSGHFKGNYKAQLTRLNH

ITNCNGAVLSVEELLIGGEMIKAGTLTLEEVRRKFNNGEINF (SEQ ID NO: 109)
CTAGTGAAATCTGAATTGGAAGAGAAGAAATCTGAACTTAGACATAAATTG

AAATATGTGCCACATGAATATATTGAATTGATTGAAATCGCAAGAAATTCA

ACTCAGGATAGAATCCTTGAAATGAAGGTGATGGAGTTCTTTATGAAGGTT

TATGGTTATCGTGGTAAACATTTGGGTGGATCAAGGAAACCAGACGGAGCA

ATTTATACTGTCGGATCTCCTATTGATTACGGTGTGATCGTTGATACTAAG

GCATATTCAGGAGGTTATAATCTTCCAATTGGTCAAGCAGATGAAATGCAA

AGATATGTCGAAGAGAATCAAACAAGAAACAAGCATATCAACCCTAATGAA

TGGTGGAAAGTCTATCCATCTTCAGTAACAGAATTTAAGTTCTTGTTTGTG

AGTGGTCATTTCAAAGGAAACTACAAAGCTCAGCTTACAAGATTGAATCAT

ATCACTAATTGTAATGGAGCTGTTCTTAGTGTAGAAGAGCTTTTGATTGGT

GGAGAAATGATTAAAGCTGGTACATTGACACTTGAGGAAGTGAGAAGGAAA

TTTAATAACGGTGAGATAAACTTTTAA
```

It is to be noted that to generate a nuclease that cleaves double strand DNA at a lower efficiency, or that cleaves single strand DNA to generate a nick rather than a double strand break, a FokI sequence can be mutated to alter its activity or its ability to dimerize. For example, the aspartic acid residue at the position corresponding to position 450 of a full-length FokI endonuclease can be replaced with an alanine residue, resulting in a nuclease that nicks rather than fully cleaves double stranded DNA, or that cleaves double stranded DNA but with a lower efficiency than non-mutagenized FokI. In some cases, the aspartic acid residue at the position corresponding to position 483 of a full-length FokI endonuclease and the arginine residue at the position corresponding to position 487 of a full-length FokI endonuclease can be replaced with alanine residues, resulting in a FokI that has reduced ability to dimerize. In some embodiments, an a-mitoTALE nuclease or mitoTALE nickase can include a FokI heterodimer in which one monomer contains the wild type FokI amino acid sequence, while the other monomer contains a FokI amino acid sequence with a D450A mutation or D483A and R487A mutations. An "aFokI" nuclease, as used herein, is a FokI polypeptide with attenuated cleaving or dimerization ability; an a-mitoTALE nuclease (or mitoTALE nickase) typically contains an aFokI domain. a-mitoTALE nucleases that have nickase activity can be useful for cleaving the light chain of a targeted mtDNA sequence or for serving as blocking molecules as described further below.

In some embodiments, a chimeric DNA nickase can include a mitochondrial targeting sequence fused to a CRISPR/Cas polypeptide. In its native context, the CRISPR/Cas system provides bacteria and archaea with immunity to invading foreign nucleic acids (Jinek et al., *Science* 337: 816-821, 2012). The CRISPR/Cas system is functionally analogous to eukaryotic RNA interference, using RNA base pairing to direct DNA or RNA cleavage. This process relies on (a) small RNAs that base-pair with sequences carried by invading nucleic acid, and (b) a specialized class of Cas endonucleases that cleave nucleic acids complementary to the small RNA. In some embodiments, a Cas9 endonuclease (e.g., a *Streptococcus pyogenes* Cas9 endonuclease) can be used. The CRISPR/Cas system can be reprogrammed to create targeted double-strand DNA breaks in higher-eukaryotic genomes, including animal and plant cells (Mali et al., *Science* 339:823-826, 2013; and Li et al., *Nature Biotechnol.* 31(8):688-691, 2013). Further, by modifying specific amino acids in the Cas protein that are responsible for DNA cleavage, the CRISPR/Cas system can function as a DNA nickase (Jinek et al., supra). For example, Cas9 nuclease proteins having a D10A or H840A mutation can have nickase activity.

Directing the Cas9 protein to a particular sequence requires crRNA and tracrRNA sequences that aid in directing the Cas/RNA complex to target DNA sequence (Makarova et al., *Nat. Rev. Microbiol.,* 9(6):467-477, 2011). The modification of a single targeting RNA can be sufficient to alter the nucleotide target of a Cas protein. In some cases, crRNA and tracrRNA can be engineered as a single cr/tracrRNA hybrid to direct Cas activity (also referred to as a "guide RNA" or gRNA). Thus, introduction of a chimeric Cas nickase into a cell with one or more crRNA and tracrRNA sequences (or one or more gRNA sequences) that are targeted to one or more mtDNA sequences, where the chimeric Cas nickase includes a mitochondrial targeting sequence and the gRNA or crRNA and tracrRNA are linked to a mitochondrial RNA targeting sequence (see, e.g., Sieber et al., *Nucl. Acids Res.* doi:10.1093/nar/gkr380, 2011) can direct the gRNA/crRNA and tracrRNA and the Cas nickase to the selected mtDNA sequence.

Methods for altering the mtDNA of a eukaryotic cell (e.g., a cell in culture or a cell within a eukaryotic organism, including a non-human vertebrate such as a zebrafish, a mouse, a rat, a rabbit, a sheep, a pig, or a dog) can include introducing one or more (e.g., one, two, three, four, five, six, or more than six) recombinant DNA nucleases and/or nickases (e.g., a-mitoTALE nucleases and/or mitoTALE nickases) into the cell, either by introducing one or more nuclease and/or nickase polypeptides or by introducing nucleic acid encoding one or more nuclease and/or nickase polypeptides. For example, an a-mitoTALE nuclease can be introduced into a cell as a nucleic acid vector encoding the chimeric polypeptide, or as a polypeptide per se. Any suitable a-mitoTALE nuclease or mitoTALE nickase can be used in the methods described herein. In some embodiments, for example, an a-mitoTALE nuclease or mitoTALE nickase having a TALE scaffold based on the following reference sequence:

```
(SEQ ID NO: 110 - inserted RVDs - SEQ ID NO: 111)
MAGYLKVLSSLSRSAATLSKSPAVLAPACQSLQQRNYADKRIQSRDVTRVD

LRTLGYSQQQQEKIKPKVRSTVAQHHEALVGHGFTHAHIVALSQHPAALGT

VAVTYQHIITALPEATHEDIVGVGKQWSGARALEALLTDAGELRGPPLQLD

TGQLVKIAKRGGVTAMEAVHASRNALTGA_HLVALACLGGRPAMDAVKKG

LPHAPELIRRVNRRIGERTSHRVASRSQLVKSELEEKKSELRHKLKYPHEY

IELIEIARNSTQDRILEMKVMEFFMKVYGYRGKHLGGSRKPDGAIYTVGSP

IDYGVIVDTKAYSGGYNLPIGQADEMQRYVEENQTRNKHINPNEWWKVYPS

SVTEFKFLFVSGHFKGNYKAQLTRLNHITNCNGAVLSVEELLIGGEMIKAG

TLTLEEVRRKFNNGEINF,
``` where the underlined sequence is the zebrafish idh2 MTS, the italicized sequence is the GoldyTALE backbone, with underscored spaces indicating the position of the sequences containing RVDs, and the bold sequence is the FokI/aFokI sequence. The underlined aspartic acids in the FokI sequence are at positions 450 and 483, and the underlined arginine in the FokI sequence is at position 487.

As described herein, more than one (e.g., two, three, four, five, six, or more than six) a-mitoTALE nucleases or mitoTALE nickases can be introduced into a cell or an organism, with each a-mitoTALE nuclease and nickase targeting a different sequence. Such methods can lead to multiple nicks in the mitochondrial DNA within the cell or the organism, and in some cases (e.g., as in the Examples below) can lead to a deletion of several kb of genomic mtDNA sequence.

In some embodiments, one or more a-mitoTALE nucleases or mitoTALE nickases can be introduced into a cell in combination with a mitoTALE nuclease that does not have attenuated activity. Methods that include such a combination of molecules can result in an increased level of mitochondrial DNA deletion, and increased heteroplasmy as compared to the level of heteroplasmy achieved using a-mitoTALE nucleases or mitoTALE nickases alone. Thus, a method can include introducing into a cell one or more nucleic acid vectors that encode an a-mitoTALE nuclease or a mitoTALE nickase, in combination with a nucleic acid vector encoding a mitoTALE nuclease, or the a-mitoTALE nuclease, mitoTALE nickase, and mitoTALE nuclease polypeptides may be introduced into the cell. In some embodiments, the mitoTALE nuclease may be targeted to a sequence within the region of mtDNA that is targeted by the a-mitoTALE nucleases or mitoTALE nickases for deletion.

In some cases, two or more mitoTALE nickases, mitoTALE molecules that lack the ability to cleave either single or double stranded DNA, or mitoTALE molecules that lack the ability to dimerize (either because they contain an aFokI domain that is unable to dimerize or because they lack a FokI domain altogether) can be introduced into a cell as "blocking" molecules, in combination with a mitoTALE nuclease or mitoTALE nickase. The blocking molecules can be targeted to sequences at either end of a desired sequence to be deleted from the mitochondrial DNA, while the mitoTALE nuclease or mitoTALE nickase can be targeted to a sequence within the sequence to be deleted. The action of the mitoTALE nuclease or mitoTALE nickase can generate a single stranded nick or a DSB, and the sequence between the blocking molecules can then be deleted.

Isolated chimeric DNA nuclease and nickase nucleic acids and polypeptides that are targeted to mtDNA also are provided herein. The term "polypeptide" as used herein refers to a compound of two or more subunit amino acids regardless of post-translational modification (e.g., phosphorylation or glycosylation). The subunits may be linked by peptide bonds or other bonds such as, for example, ester or ether bonds. The term "amino acid" refers to either natural and/or unnatural or synthetic amino acids, including D/L optical isomers.

By "isolated" or "purified" with respect to a polypeptide it is meant that the polypeptide is separated to some extent from the cellular components with which it is normally found in nature (e.g., other polypeptides, lipids, carbohydrates, and nucleic acids). A purified polypeptide can yield a single major band on a non-reducing polyacrylamide gel. A purified polypeptide can be at least about 75% pure (e.g., at least 80%, 85%, 90%, 95%, 97%, 98%, 99%, or 100% pure). Purified polypeptides can be obtained by, for example, extraction from a natural source, by chemical synthesis, or by recombinant production in a host cell or transgenic plant, and can be purified using, for example, affinity chromatography, immunoprecipitation, size exclusion chromatography, and ion exchange chromatography. The extent of purification can be measured using any appropriate method, including, without limitation, column chromatography, polyacrylamide gel electrophoresis, or high-performance liquid chromatography.

The terms "nucleic acid" and "polynucleotide" are used interchangeably, and refer to both RNA and DNA, including cDNA, genomic DNA, synthetic (e.g., chemically synthesized) DNA, and DNA (or RNA) containing nucleic acid analogs. Polynucleotides can have any three-dimensional structure. A nucleic acid can be double-stranded or single-stranded (i.e., a sense strand or an antisense single strand). Non-limiting examples of polynucleotides include genes, gene fragments, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers, as well as nucleic acid analogs.

As used herein, "isolated," when in reference to a nucleic acid, refers to a nucleic acid that is separated from other nucleic acids that are present in a genome, e.g., a plant genome, including nucleic acids that normally flank one or both sides of the nucleic acid in the genome. The term "isolated" as used herein with respect to nucleic acids also includes any non-naturally-occurring sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences, as well as DNA that is incorporated into a vector, an autonomously replicating plasmid, a virus (e.g., a pararetrovirus, a retrovirus, lentivirus, adenovirus, or herpes virus), or the genomic DNA of a prokaryote or eukaryote. In addition, an isolated nucleic acid can include a recombinant nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

A nucleic acid can be made by, for example, chemical synthesis or polymerase chain reaction (PCR). PCR refers to a procedure or technique in which target nucleic acids are amplified. PCR can be used to amplify specific sequences from DNA as well as RNA, including sequences from total genomic DNA or total cellular RNA. Various PCR methods are described, for example, in *PCR Primer: A Laboratory Manual*, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid.

Isolated nucleic acids also can be obtained by mutagenesis. For example, a donor nucleic acid sequence can be mutated using standard techniques, including oligonucleotide-directed mutagenesis and site-directed mutagenesis through PCR. See, *Short Protocols in Molecular Biology*, Chapter 8, Green Publishing Associates and John Wiley & Sons, Ausubel et al. (Ed.), 1992.

This document also provides nucleic acid vectors containing nucleotide sequences that encode one or more chimeric DNA nuclease or nickase (e.g., a-mitoTALE nuclease) molecules. A "vector" is a replicon, such as a plasmid, phage, or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs, YACs, or PACs. The term "vector" includes cloning and expression vectors, as well as viral vectors and integrating vectors. An "expression vector" is a vector that includes one or more expression control sequences, and an "expression control sequence" is a DNA sequence that controls and regulates the transcription and/or translation of another DNA sequence. Suitable expression vectors include, without limitation, plasmids and viral vectors derived from, for example, bacteriophage, baculoviruses, tobacco mosaic virus, herpes viruses, cytomegalovirus, retroviruses, vaccinia viruses, adenoviruses, and adeno-associated viruses. Numerous vectors and expression systems are commercially available from such corporations as Novagen (Madison, WI), Clontech (Palo Alto, CA), Stratagene (La Jolla, CA), and Invitrogen/Life Technologies (Carlsbad, CA).

The nucleic acids provided herein can include a "regulatory region" (also referred to as a "control element" or "expression control sequence"), which is a nucleotide sequence that influences transcription or translation initiation and rate, and/or stability and/or mobility of the transcript or polypeptide product. Regulatory regions include, without limitation, promoter sequences, enhancer sequences, response elements, protein recognition sites, inducible elements, promoter control elements, protein binding sequences, 5' and 3' untranslated regions (UTRs), transcriptional start sites, termination sequences, polyadenylation sequences, introns, and other regulatory regions that can reside within coding sequences, such as secretory signals, mitochondrial targeting sequences, and protease cleavage sites.

As used herein, "operably linked" means incorporated into a genetic construct so that expression control sequences effectively control expression of a coding sequence of interest. A coding sequence is "operably linked" and "under the control" of expression control sequences in a cell when RNA polymerase is able to transcribe the coding sequence into RNA, which if an mRNA, then can be translated into the protein encoded by the coding sequence. Thus, a regulatory region can modulate, e.g., regulate, facilitate or drive, transcription in the plant cell, plant, or plant tissue in which it is desired to express a modified target nucleic acid.

A promoter is an expression control sequence composed of a region of a DNA molecule, typically within 100 nucleotides upstream of the point at which transcription starts (generally near the initiation site for RNA polymerase II). Promoters are involved in recognition and binding of RNA polymerase and other proteins to initiate and modulate transcription. To bring a coding sequence under the control of a promoter, it typically is necessary to position the translation initiation site of the translational reading frame of the polypeptide between one and about fifty nucleotides downstream of the promoter. A promoter can, however, be positioned as much as about 5,000 nucleotides upstream of the translation start site, or about 2,000 nucleotides upstream of the transcription start site. A promoter typically includes at least a core (basal) promoter. A promoter also may include at least one control element such as an upstream element. Such elements include upstream activation regions and, optionally, other DNA sequences that affect transcription of a polynucleotide such as a synthetic upstream element.

The choice of promoters to be included depends upon several factors, including, but not limited to, efficiency, selectability, inducibility, desired expression level, and cell or tissue specificity. For example, tissue-, organ- and cell-specific promoters that confer transcription only or predominantly in a particular tissue, organ, and cell type, respectively, can be used. Alternatively, constitutive promoters can promote transcription of an operably linked nucleic acid in most or all tissues, throughout development. Other classes of promoters include, without limitation, inducible promoters, such as promoters that confer transcription in response to external stimuli (e.g., chemical agents, developmental stimuli, or environmental stimuli).

The vectors provided herein also can include, for example, origins of replication, and/or scaffold attachment regions (SARs). In addition, an expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin, or Flag™ tag (Kodak, New Haven, CT) sequences typically are expressed as a fusion with the encoded polypeptide. Such tags can be inserted anywhere within the polypeptide, including at either the carboxyl or amino terminus.

The terms "vector" or "vectors" refer to a nucleic acid molecule capable of transporting another nucleic acid to which it has been linked. A "vector" in the present document includes, but is not limited to, a viral vector, a plasmid, a RNA vector or a linear or circular DNA or RNA molecule which may consists of a chromosomal, non-chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available.

Recombinant nucleic acid constructs can include a polynucleotide sequence inserted into a vector suitable for transformation of cells (e.g., plant cells or animal cells). Recombinant vectors can be made using, for example, standard recombinant DNA techniques (see, e.g., Sambrook et al. (1989) *Molecular Cloning: A Laboratory Manual,* 2nd ed., Cold Spring Harbor Laboratory, Cold Spring Harbor, NY).

Vectors can be introduced into eukaryotic cells or non-human organisms (e.g., plants, including monocots and dicots, or animals, including fish, rodents, sheep, pigs, cows, dogs, cats, and primates) by any of a variety of methods (e.g., injection, direct uptake, projectile bombardment, liposomes, or electroporation). As described in the Examples herein, for example, DNA or RNA encoding one or more (e.g., one, two, three, four, five, six, or more than six) mitoTALE nucleases, a-mitoTALE nucleases, or mitoTALE nickases, or a combination of one or more nucleases and one or more nickases (e.g., two mitoTALE nickases and an a-mitoTALE nuclease or a mitoTALE nuclease), can be transformed into a cell or microinjected into an organism such as a zebrafish (e.g., a zebrafish embryo). The cell (or progeny thereof) or organism can be assessed using, for example, PCR and sequencing techniques to determine whether a deletion has been generated at or near the targeted sequence(s), and to assess the sizes of any such deletions. In some embodiments, a transformed organism (e.g., an embryo) can be allowed to develop, and the resulting organism can be assessed to determine whether the deletions have been maintained.

This document also provides methods for editing mtDNA within a cell (e.g., a mammalian or non-mammalian eukaryotic cell, such as cell from a human or other non-human mammal, or a non-mammalian eukaryote such as a zebrafish). The editing can be in vitro or in vivo. The methods provided herein can include introducing several components into a cell, including (a) a DNA cleaving enzyme targeted to the mtDNA sequence to be deleted, (b) a first DNA binding component targeted to a sequence adjacent to the 5' end of a mtDNA sequence to be deleted, and (c) a second DNA binding component targeted to a sequence adjacent to the 3' end of the mtDNA sequence to be deleted. The first and second DNA binding components of (b) and (c) also are referred to herein as "blocking" molecules.

The DNA cleaving enzyme can be a nuclease that generates a double stranded break DSB within the mtDNA sequence to be deleted, or can be a nickase that generates a single strand nick on the light strand of the mtDNA sequence to be deleted. In some cases, as described herein, the DNA cleaving enzyme can be a dimeric nuclease containing a pair of monomers, where each monomer includes a first portion containing a MTS, a second portion containing an amino acid sequence targeting the monomer to the mtDNA sequence to be deleted, and a third portion containing a nuclease domain, such that when the monomers are bound to their target sequences within the mtDNA sequence to be deleted, the nuclease domains form a dimer that cleaves within the mtDNA sequence to be deleted. The nuclease domain can be a FokI endonuclease domain. In some cases, the DNA cleaving enzyme can be a dimeric nickase containing a pair of monomers that each include a first portion containing a MTS, a second portion containing an amino acid sequence targeting the DNA cleaving enzyme to the sequence to be deleted from the mtDNA, and a third portion containing a nuclease domain, where one monomer of the pair includes an unmodified nuclease domain and the other monomer of the pair includes a modified nuclease domain, such that when the monomers are bound to their target sequences within the mtDNA sequence to be deleted, the nuclease domains form a dimer that nicks the light strand of the mtDNA sequence to be deleted. The modified FokI endonuclease domain can, for example, include a substitution at position 450 (e.g., a D450A substitution) relative to the sequence of a full-length FokI endonuclease domain.

The first and second DNA binding components can be monomeric or dimeric, and may or may not have the ability to generate a single stranded nick in the mtDNA. For example, the first and second DNA binding components can both be monomeric or can both be dimeric such that they each nick the mtDNA at their respective target site. In some cases, the DNA binding component targeted to the 5' end of the mtDNA sequence to be deleted can be dimeric, while the DNA binding component targeted to the 3' end of the mtDNA sequence to be deleted can be monomeric, or vice versa. The DNA cleaving enzyme and first and second blocking molecules can be introduced into a cell as RNA, DNA, polypeptide, or a combination thereof, and any appropriate method can be used to introduce the DNA cleaving enzyme and the first and second blocking molecules into a cell such that mtDNA is cleaved as described herein. In some cases, mRNA molecules encoding the DNA cleaving enzyme and the blocking components can be introduced into a cell. The mRNA can be translated in the cytoplasm and then imported as protein into the mitochondria (e.g., using a mitochondrial targeting sequence). In some cases, nuclease or nickase proteins and blocking molecules can be directly introduction into a cell as proteins. In some cases, microinjection can be used to introduce a DNA cleaving enzyme and first and second blocking molecules into a cell. Alternatively, electroporation or transfection can be used.

Any appropriate amount of a nuclease, nickase, or blocking molecule can be introduced into a cell. When mRNA is introduced, for example, about 10 pg to about 5 μg of each mRNA can be transfected into a cell. In some cases (e.g., when zebrafish cells are transfected), about 10 pg to about 500 pg of each mRNA (e.g., about 10 to 50 pg, about 50 to 100 pg, about 100 to 250 pg, or about 250 to 500 μg of each mRNA) can be introduced. In some cases (e.g., when human cells are transfected), about 500 ng to about 5 μg of each mRNA (e.g., about 500 to 750 ng, about 750 to 1000 ng, about 1 to 2 μg, about 2 to 3 μg, about 3 to 4 μg, or about 4 to 5 μg of each mRNA) can be introduced.

Further, any appropriate mtDNA sequence can be targeted. Many mtDNA sequences are known, including but not limited to those described herein, and methods/systems for selecting particular sequences to target with TALE nucleases or CRISPR/Cas systems are available.

The invention will be further described in the following examples, which do not limit the scope of the invention described in the claims.

EXAMPLES

Example 1—Materials and Methods

MitoTALE-nickase and -nuclease assembly: The nuclear localization sequence of GoldyTALE nuclease was replaced in the expression plasmids pT3TS-GoldyTALEN (pT3TS-mitoTALE nuclease, T3 promoter mRNA expression plasmid; Hyatt and Ekker, *Meth. Cell Biol.* 59:117-126, 1999) and pC-GoldyTALEN (pC-mitoTALE nuclease miniCaggs promoter expression plasmid) with the mitochondrial targeting sequence of zebrafish idh2 (MAGYLKVLSSLSR-SAATLSKSPAVLAPACQSLQQRNYADKRIQ; SEQ ID NO: 1). To generate a mitoTALE-nickase, the p.D450A amino acid substitution was made in the FokI domain of one half of a TALE-nuclease pair (Waugh and Sauer, *Proc. Natl. Acad. Sci. USA* 90:9596-9600, 1993). For a non-cutting TALE-nuclease, two TALE-nucleases harboring the p.D450A substitution were used. To make a non-dimerizing FokI, two amino acid substitutions were made (p.D483A and p.R487A) and each TALE arm harbored these variants in cis. The final mitoTALE backbone plasmids used are available from Addgene. To target specific sequences in the genome, RVDs were cloned into the GoldyTALE backbone using the FusX assembly system (Ma et al., *Hum. Gene Ther* 27:451-463, 2016). The RVDs used were HD=C, NN=G, NI=A, NG=T. The sequences targeted by the TALEs described herein are listed in TABLE 1.

Zebrafish TALE mRNA embryo injections and deletion screening: Once the RVDs were cloned, mRNA was made for zebrafish microinjections. Each TALE-nuclease expression plasmid was digested with SacI for 2-3 hours at 37° C., and synthetic mRNA was made (T3 mMessage mMachine kit, Ambion) and extracted using a phenol/chloroform extraction (according to the T3 mMessage mMachine kit instructions). 12.5 pg of each mitoTALE-nickase (FIGS. 1B, 2A, and 3A) or mitoTALE-FokI arm (FIG. 4A) was co-injected into one-celled embryos with 50 pg of mitoTALE nuclease (FIGS. 1B, 2A, and 3A) or mitoTALE-nickase (FIG. 4A) when indicated. After 3 days, individual larval zebrafish were collected in 1.7 mL microcentrifuge tubes, and DNA was extracted in 40 μL of an extraction buffer (50 mM Tris-HCl pH 8.5, 1 mM EDTA, 0.5% Tween-20, 200 μg/ml proteinase K) at 55° C. overnight and centrifuged at 17,000×g for 1 minute after extraction was complete. In each condition (control and experimental), 8 individual zebrafish embryos were collected and screened for mtDNA deletions. Replicates were done in triplicate for all mtDNA editing experiments in both zebrafish embryos and human cells, with the exception the experiments shown in FIG. 1C, FIG. 4B, and FIG. 4H, which were done in duplicate. One microliter of DNA extract was then used for PCR (Platinum Taq, Invitrogen). All PCR reactions were kept on ice until the thermocycler reached 95° C. Primer concentrations were 0.4 μM for all reactions, and the final reaction volume was 25 μL. To include $MgCl_2$, and dNTPs, and loading dye, 5× MyTaq Red buffer was used (Bioline Cat # BIO-37112). For screening nd4 deletions, the following thermocycler parameters were used: 95° C. for 5 minutes, (95° C. for 30 seconds, 60° C. for 30 seconds, and 72° C. for 1 minute)×35 cycles, and then 72° C. for 5 minutes. For screening zebrafish nd5/atp8 deletions, the following thermocycler parameters were used: 95° C. for 5 minutes, (95° C. for 30 seconds, 64° C. for 30 seconds, and 72° C. for 1 minute)×35 cycles, and then 72° C. for 5 minutes. For control PCR to detect successful DNA extraction, the following thermocycler parameters were used: 95° C. for 5 minutes, (95° C. for 30 seconds, 55° C. for 30 seconds, and 72° C. for 1 minute)×35 cycles, and then 72° C. for 5 minutes. In all cases, 5 μL of PCR product was run on a 1-1.5% gel and extracted for sequencing using the Qiaex 11 gel extraction kit (Qiagen), and then TOPO TA cloned into a sequencing vector using the TOPO PCR cloning kit (Invitrogen Cat # K4575J10), and Sanger sequenced.

Human mitoTALE transfections and deletion screening: 293T cells (ATCC CRL-3216) were transfected with 500 ng of each pC-mitoTALE-nickase and 1 μg of pC-mitoTALE nuclease as indicated. 500 ng of a plasmid encoding enhanced green fluorescent protein (EGFP) was included to ensure proper transfections and to act as a negative control.

Transfections were done using 100 μL tips of the Neon transfection system (Invitrogen) and electroporation conditions were as recommended by Invitrogen for HEK293 cells (pulse voltage=1,100 v, pulse width=20 ms, pulse number=2, cell density~5×10). Cells were immediately put into 6-well plates post transfection in DMEM media containing 10% FBS, pen-strep, 50 μg/mL uridine, and 1 mM sodium pyruvate. After 2 days, cells were moved to a T75 flask to allow for expansion. Six days later, cells were collected and mtDNA extraction was performed using a mitochondrial DNA isolation kit (Biovision Cat # K280-50). One modification was made to the protocol; on step 6 of the Mitochondrial DNA Isolation Protocol from the user manual, centrifugation was performed at 2,000×g for 6 minutes at 4° C. instead of 700×g for 10 minutes at 4° C. The resulting DNA was diluted to 50 ng/uL, and 1 μL of this was used for PCR to detect mtDNA deletions (with the same reagents as those used for zebrafish PCR). Primer sequences are listed in TABLE 2; concentrations were 0.4 μM per reaction, with a final reaction volume of 25 μL. Importantly, Taq polymerase was not added to the reaction until the reaction reached 95° C. Thermocycler parameters to detect deletions were as follows: 95° C. for 5 minutes, (95° C. for 30 seconds, 64° C. for 30 seconds, and 72° C. for 1 minute)×35 cycles, and 72° C. for 5 minutes. For control PCR to detect successful DNA extraction, the following thermocycler parameters were used: 95° C. for 5 minutes, (95° C. for 30 seconds, 55° C. for 30 seconds, and 72° C. for 1 minute)×35 cycles, and 72° C. for 5 minutes. After amplification, 5 μL of PCR product was run on a 1.5% gel and extracted for sequencing using the Qiaex II gel extraction kit (Qiagen Cat #20051), then TOPO TA cloned into a sequencing vector using the TOPO PCR cloning kit (Invitrogen Cat #K4575J10) and Sanger sequenced.

Zebrafish organ dissection and DNA extraction: Organ dissection was conducted on six euthanized 4-month-old zebrafish to collect the heart, liver, intestine, eye, brain, skeletal muscle and ovaries (Gupta and Mullins, *J. Vis. Exp.* (37), e1717, doi:10.3791/1717, 2010). Controls (animals not injected with mitoTALEs) were age- and sex-matched, and their organs collected at the same time. In total, two control fish were dissected (one male and one female), and four fish injected with mitoTALEs were dissected (two males, and two females). Organs were added to 100 μL of a DNA extraction buffer (50 mM Tris-HCl pH 8.5, 1 mM EDTA, 0.5% Tween-20, 200 μg/ml proteinase K) and incubated at 55° C. overnight, followed by centrifugation at 17,000×g for 1 minute. Bridge PCR, as well as control PCR to ensure proper DNA extraction, was performed using 2 μL of extract in a 25 μL reaction, with conditions otherwise identical to the embryo screening of nd5/atp8 deletions. Sanger sequencing was conducted following PCR to identify deletion junctions.

Droplet Digital PCR (ddPCR) to measure heteroplasmy: Droplet digital PCR was performed on DNA extracted from zebrafish embryos and adult tissue. To detect heteroplasmy, one amplicon and TaqMan probe containing a 5'HEX fluorophore and 3'quencher (IDT) was designed against a common region in the mtDNA genome (nd1) and another amplicon and probe containing a 5'FAM fluorophore and 3' quencher were designed to bridge deletion (AmtDNA) breakpoint. To ensure proper droplet saturation for a quantitative measurement of wild type genomes using the HEX fluorophore, a dilution of 1:100 was performed and accounted for upon data analysis. To detect the deleted mtDNA genomes using the FAM fluorophore, no dilution was performed. One (1) μL of sample was added to 10 μL of the 2× ddPCR supermix for probes (BioRad Cat #186-3023) along with 900 nM PCR primers and 250 nM probe, 1 μL of HindIII, and water to a final volume of 20 μL. Samples were loaded into a 96-well plate and heat-sealed with tinfoil, vortexed, and briefly centrifuged. Droplets were generated on a BioRad AutoDG automatic droplet generator. After droplet formation, samples were moved to a thermocycler and PCR was performed with 95° C. for 10 minutes, (94° C. for 30 seconds, 60° C. for 1 minute)×40 cycles, 98° C. for 10 minutes, and 4° C. hold until the samples were read on a QX200 droplet reader. Droplet analysis was performed with QuantaSoft software. The copy number of mtDNA molecules in 1 μL of sample for both wild type and deleted genomes were determined to calculate heteroplasmy. For this, the following equation was used: $([\Delta mtDNA]/[nd1]) \times 100$, where brackets are the concentration. Droplet digital PCR was performed with technical duplicates and averaged to reach each individual data points. Either 7 or 8 animals were screened for heteroplasmy quantification in zebrafish embryos (FIG. 4D), or 2 for adult tissue (FIG. 3K). Animals were chosen based on a positive signal for bridge PCR along with the same number of uninjected control animals. Once heteroplasmy was determined, GraphPad PRISM software was used to create dot plots and identify either the median (FIG. 4B) or the mean (FIG. 3K) and to calculate statistical significance (P value) using a two-sided Mann-Whitney U test for FIG. 4B.

Example 2—Editing Mitochondrial Genomes Using a "Block and Nick" System

To address the technical challenge of gene editing in mtDNA, a novel system was developed for targeted manipulation of mtDNA sequences using alternative editing strategies. Zebrafish was used as a rapid in vivo initial test system because of its conserved mtDNA genome (Broughton et al., *Genome Res.* 11:1958-1967, 2001) and ease of microinjection for efficient and quantitative delivery of genome editing tools (FIG. 1A). The zebrafish mitochondrial targeting sequence (SEQ ID NO:1) was fused to the GoldyTALE nuclease backbone (Bedell et al., *Nature* 491: 114-118, 2012) in both nuclease and nickase forms, the latter made by mutagenizing half of the FokI dimer rendering it catalytically inactive (p.D450A, FIG. 1B). The resulting mito-nickase was then evaluated for its ability to directly manipulate mtDNA genomes for new single-gene deletions as well as for site-specific, multigene variants that can molecularly model human disease.

Figure 1D:
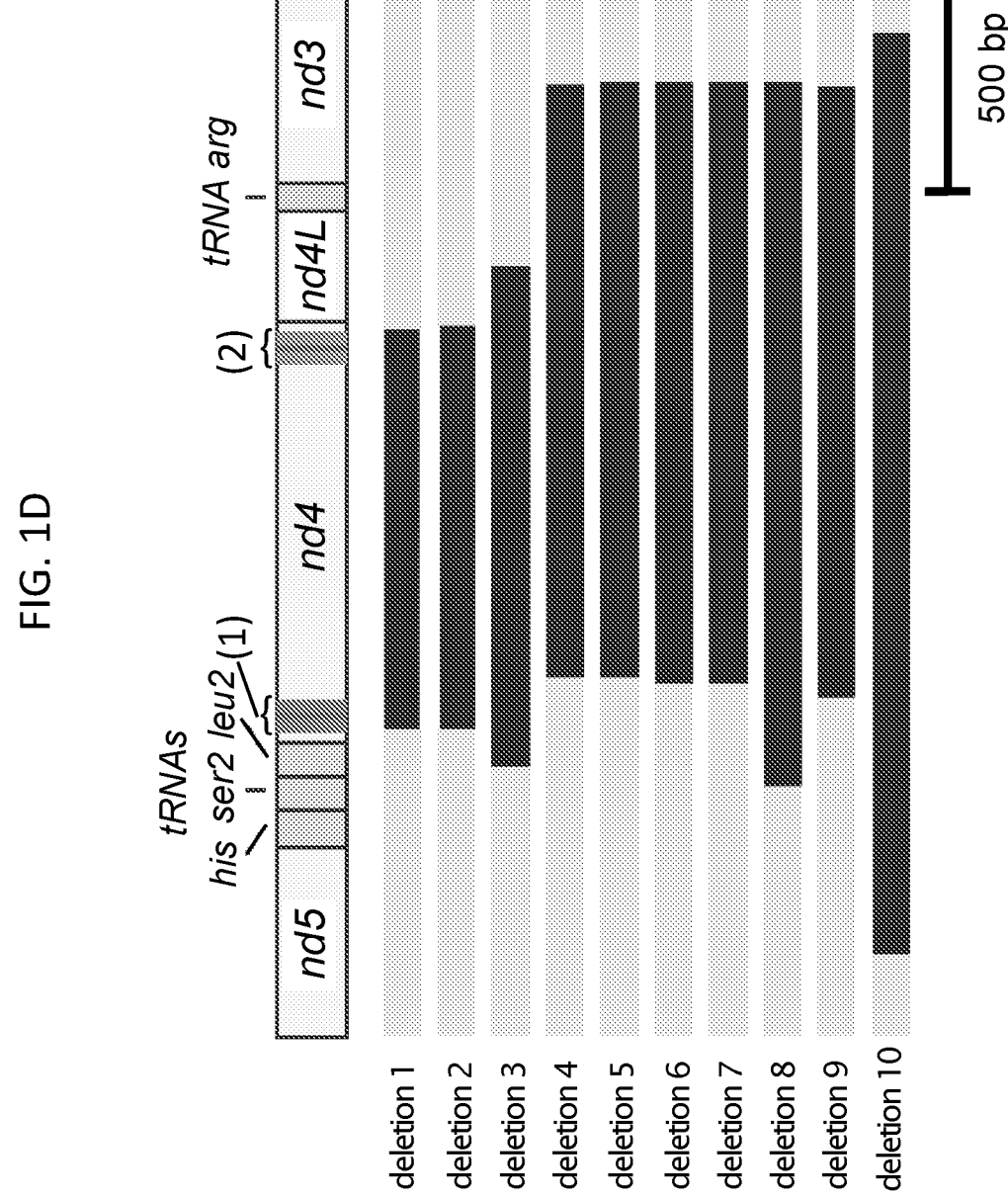

The 1.2 kilobase, protein-encoding mtDNA gene, nd4, was used to test whether this approach could yield deletions for mitochondrial DNA functional testing (FIG. 1B). By positioning two mito-nickases just inside the nd4 coding region, deletions were readily detected in about 50% of injected embryos (FIG. 1C). Sequencing confirmed that mtDNA deletions were successfully targeted to, or near, the mito-nickase sites (FIGS. 1D and 1E). In every deletion screened, nd4 was deleted along with up to 500 bp of adjacent nickase site-sequence (FIG. 1D).

Figure 2A:
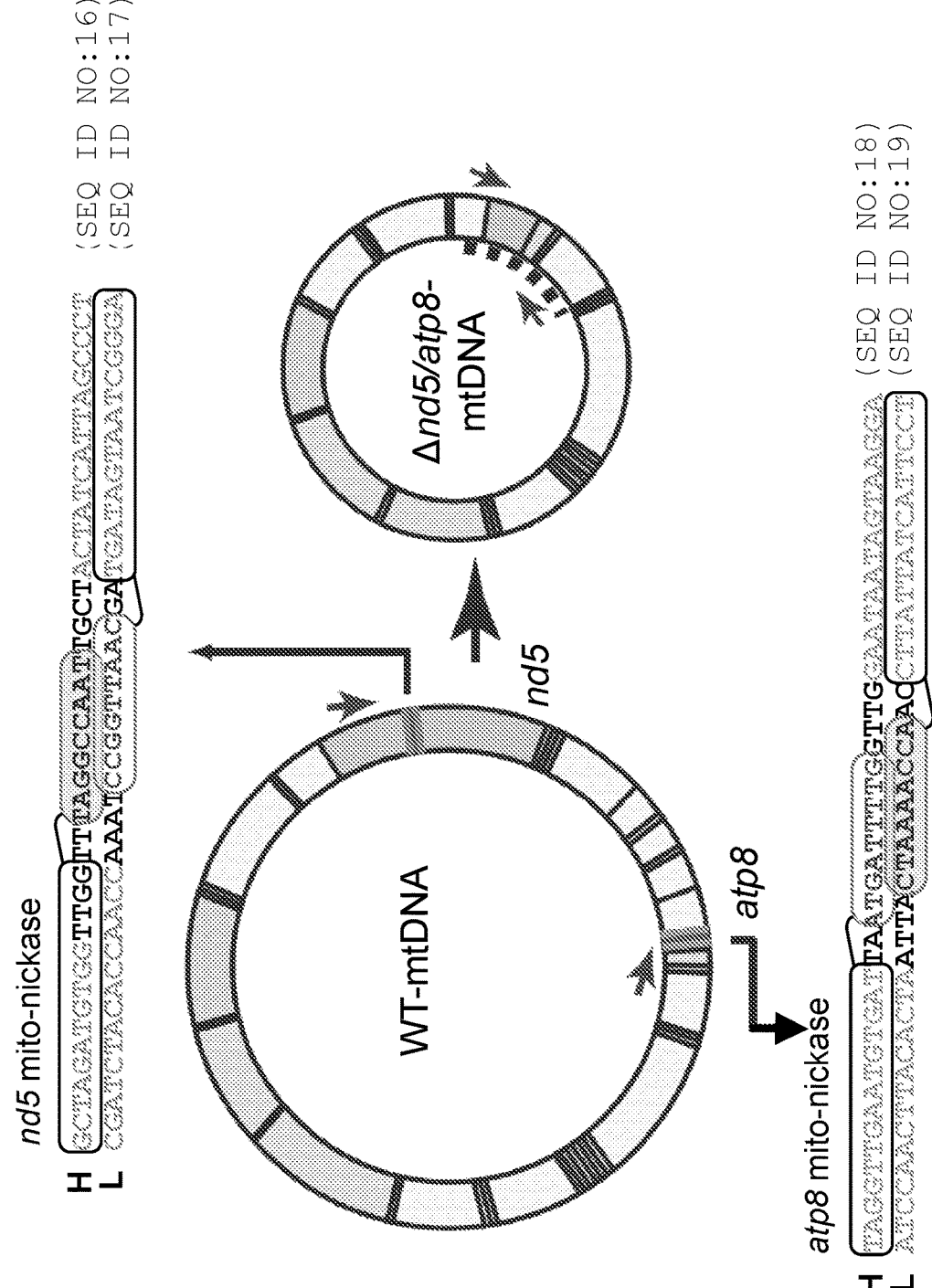
Figure 2B:
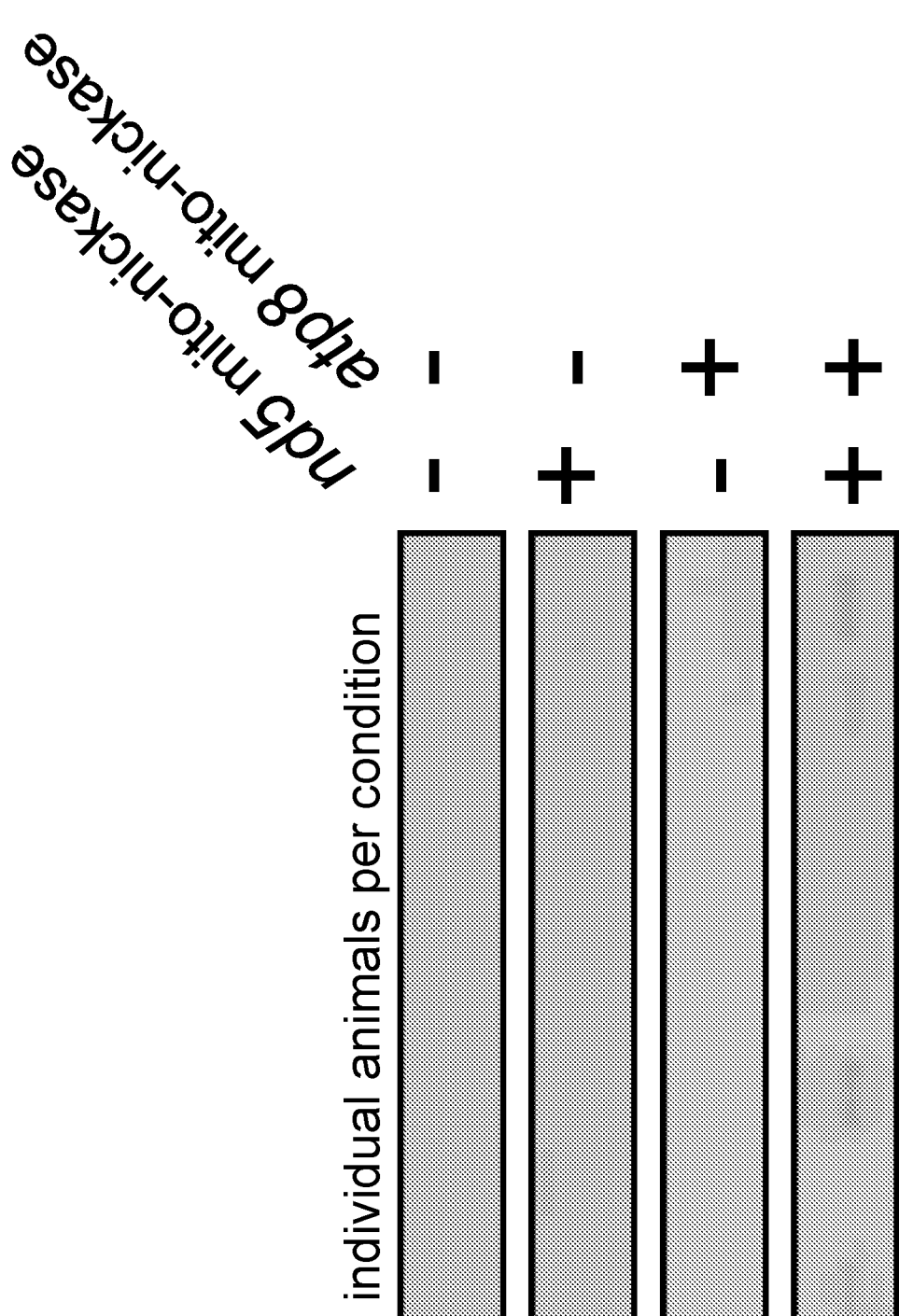
Figure 2C:
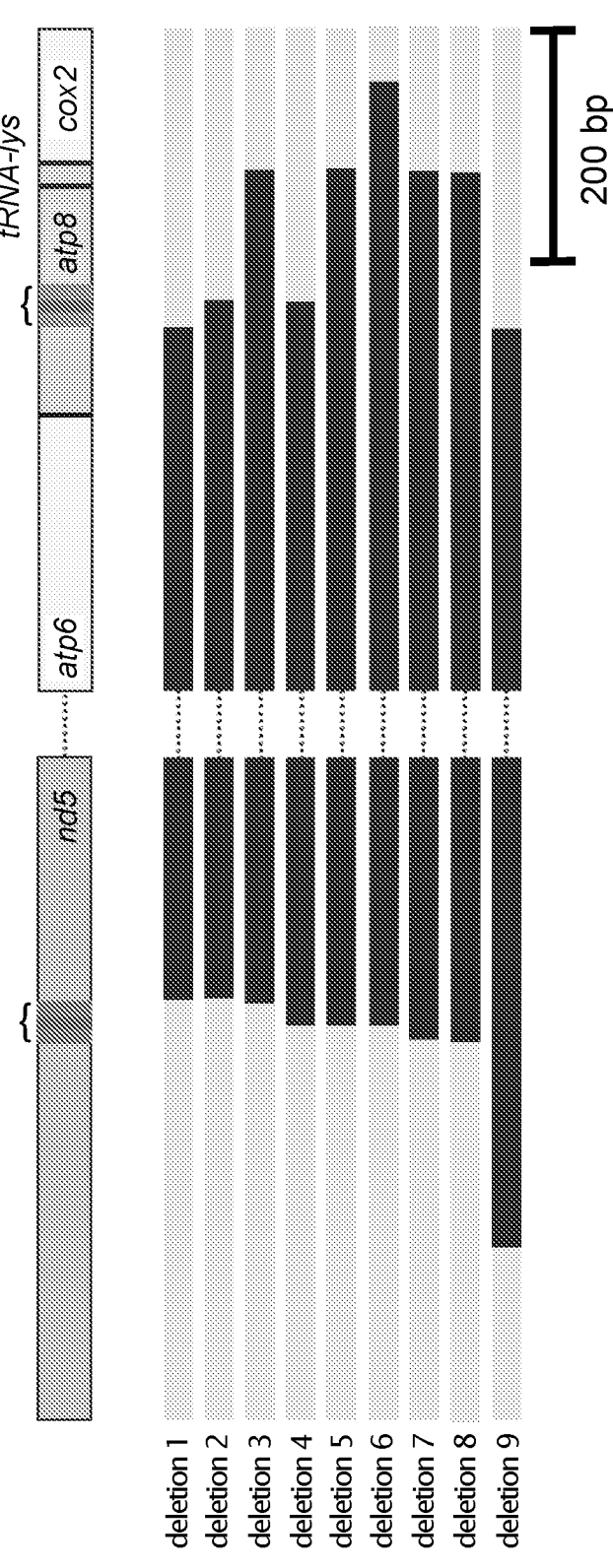

Numerous human disorders are caused by mtDNA deletions. For instance, a 'common deletion' of 4977 bp between nd5 and atp8 is identified in most cases of Kearns-Sayre Syndrome (KSS) (Moraes et al., *N. EngL. J. Med.* 320:1293-1299, 1989; and Schon et al., *Science* 244:346-349, 1989). To molecularly model this deletion, two mito-nickases were targeted within these genes, and the resulting products were detected by bridge-PCR and sequencing (FIG. 2A). The bridge-PCR was designed to selectively amplify mtDNA deletions by positioning two primers outside the mito-nickase sites and maintaining a short extension time to avoid amplification of the full-length wild type product (FIG. 2A). Using this method, deletions were detected in nearly 30% of injected animals, and sequence verification confirmed deletion junctions near the mito-nickase targeted sites (designated the Δnd5/atp8-mtDNA genome, FIGS. 2B and 2C). The resulting deletions were relatively more precise than the nd4-targeted deletions, with ⅗ of the sequenced deletion junctions within both mito-nickase binding sites or intervening spacer sequence (FIGS. 2C and 2D).

Figure 3A:
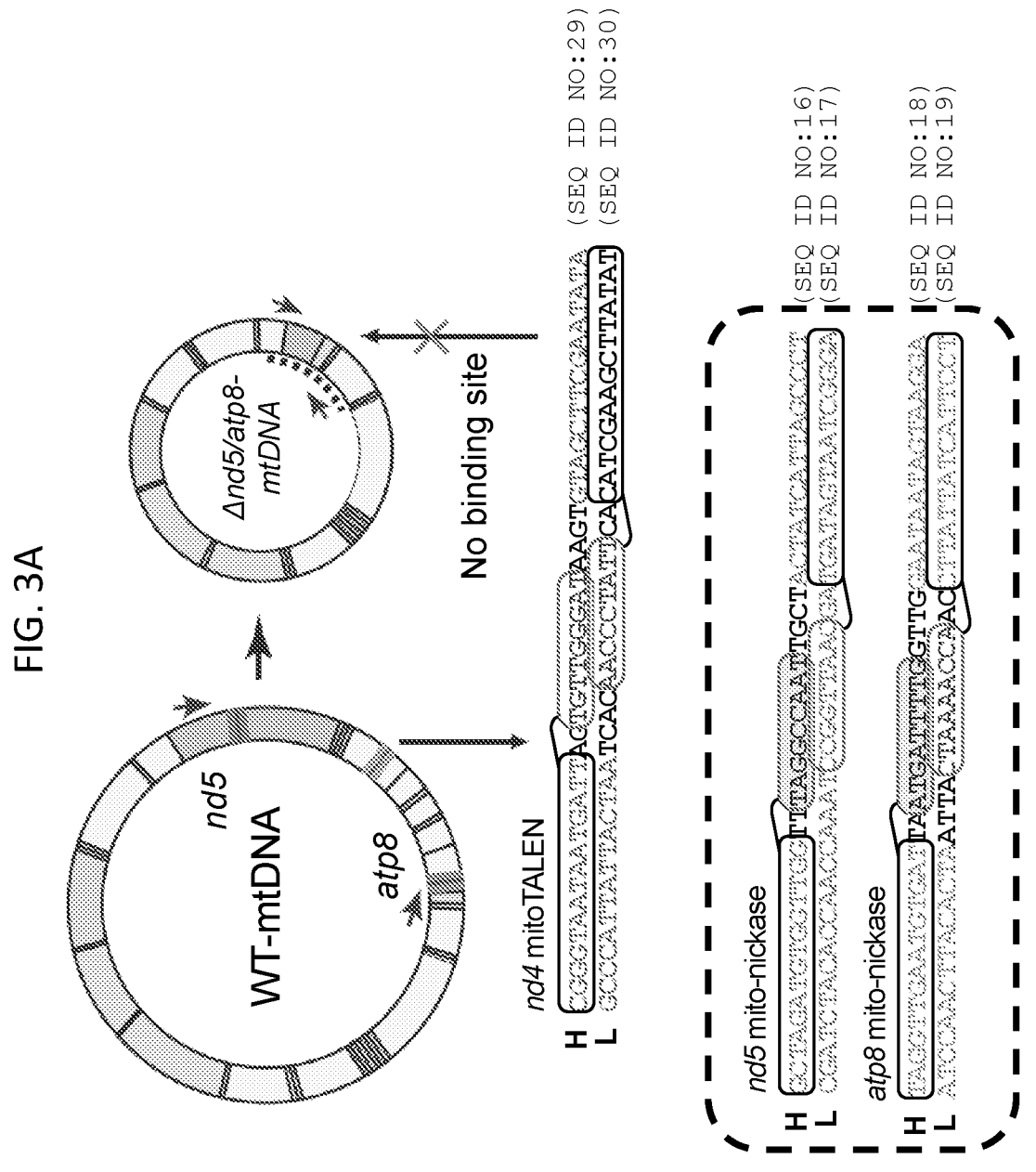
Figure 3B:
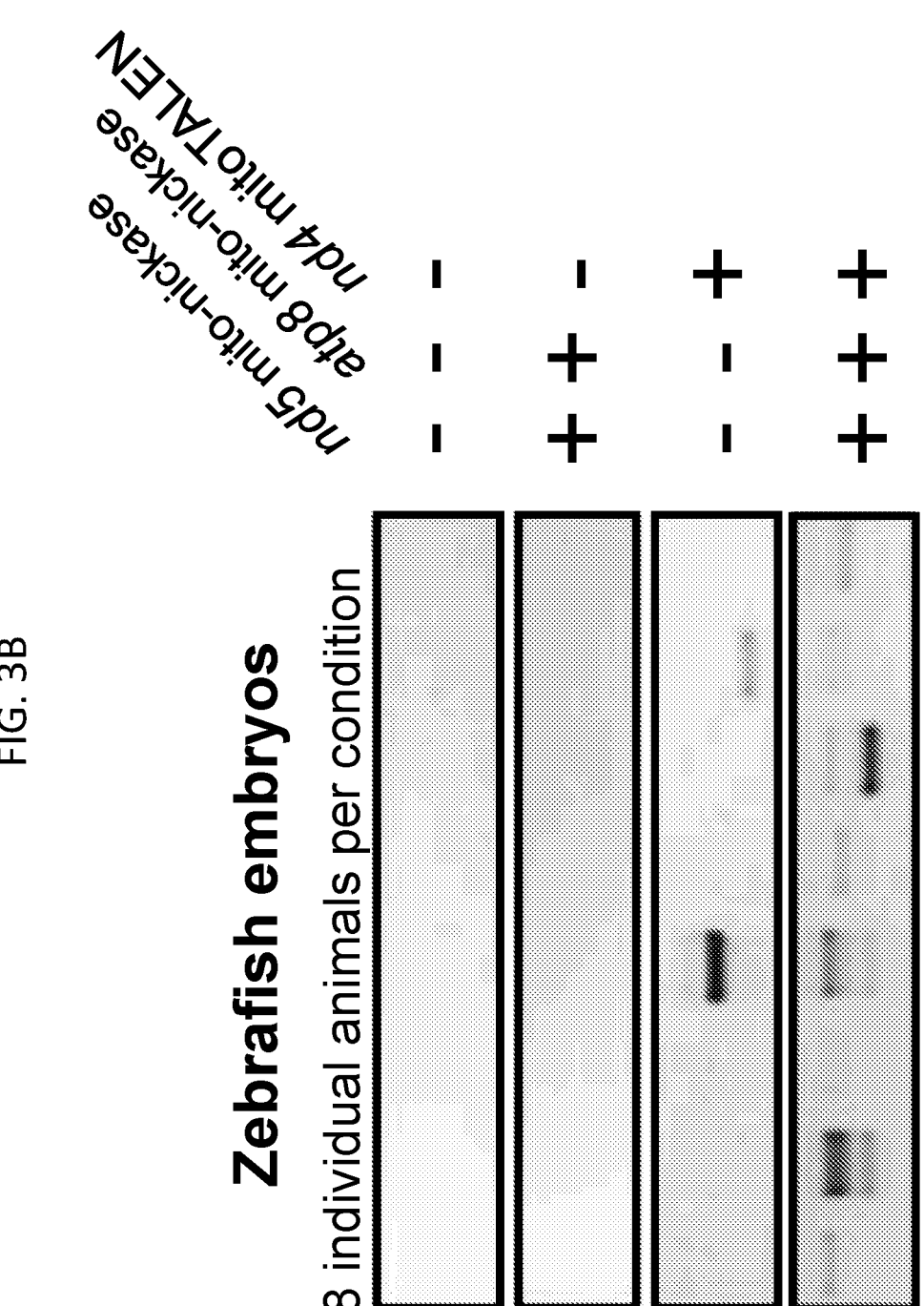
Figure 3C:
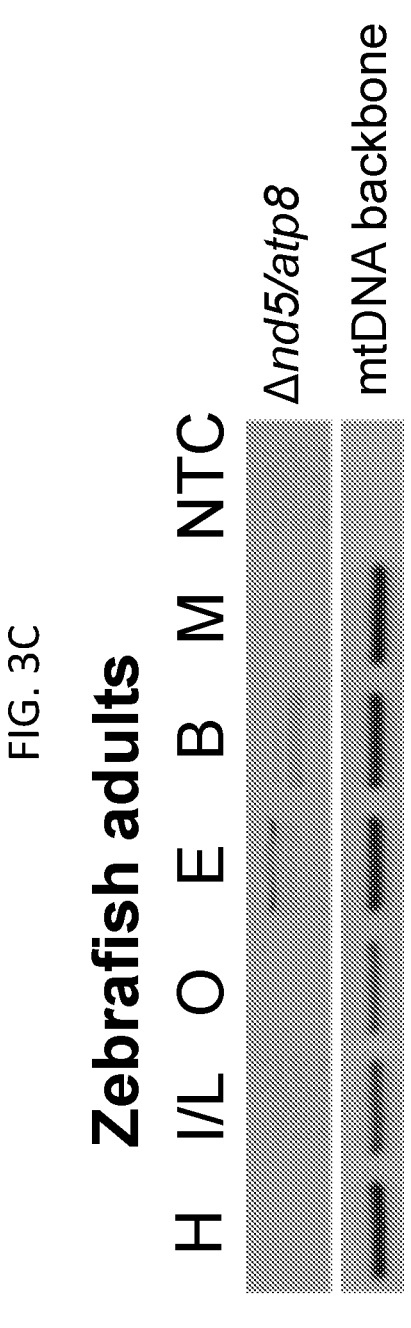
Figure 3D:
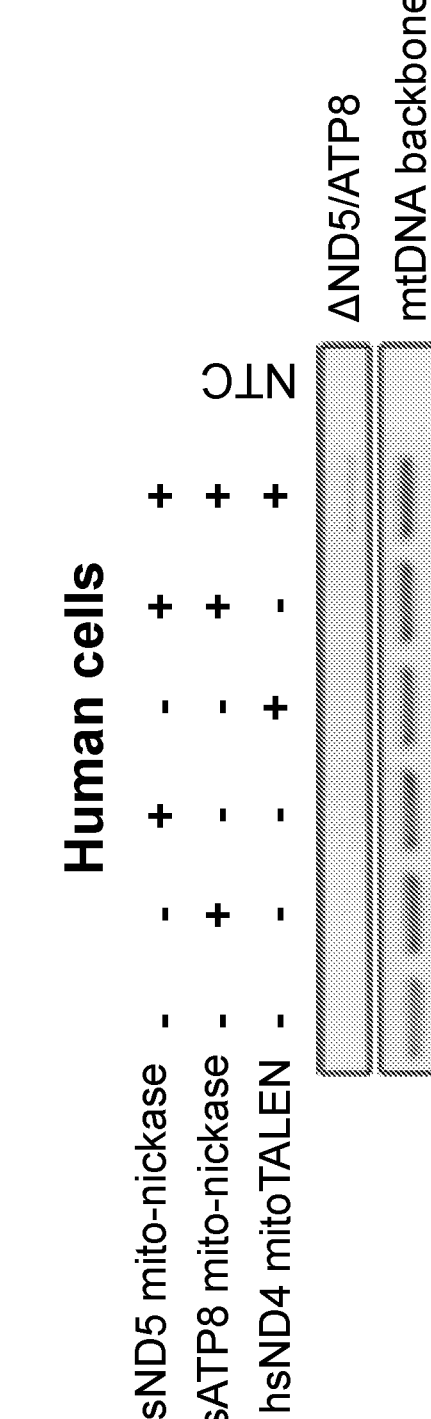
Figure 3E:
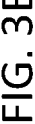
Figure 3G:
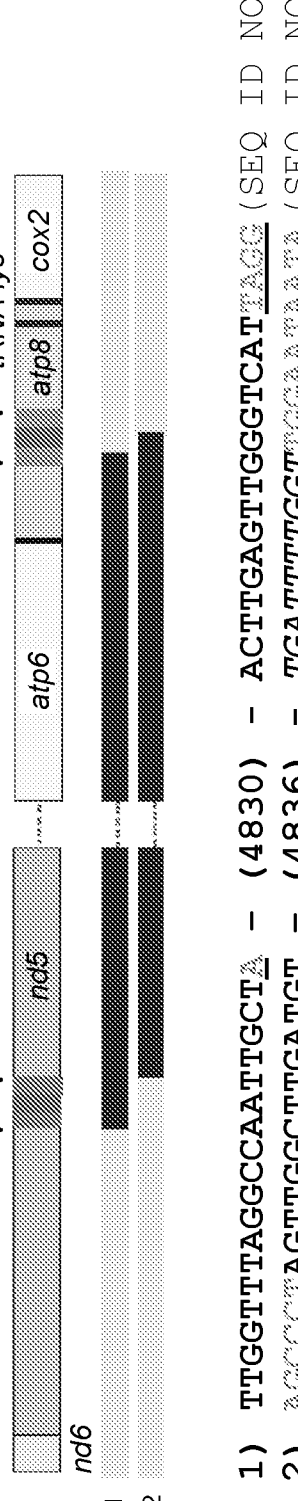
Figure 3H:
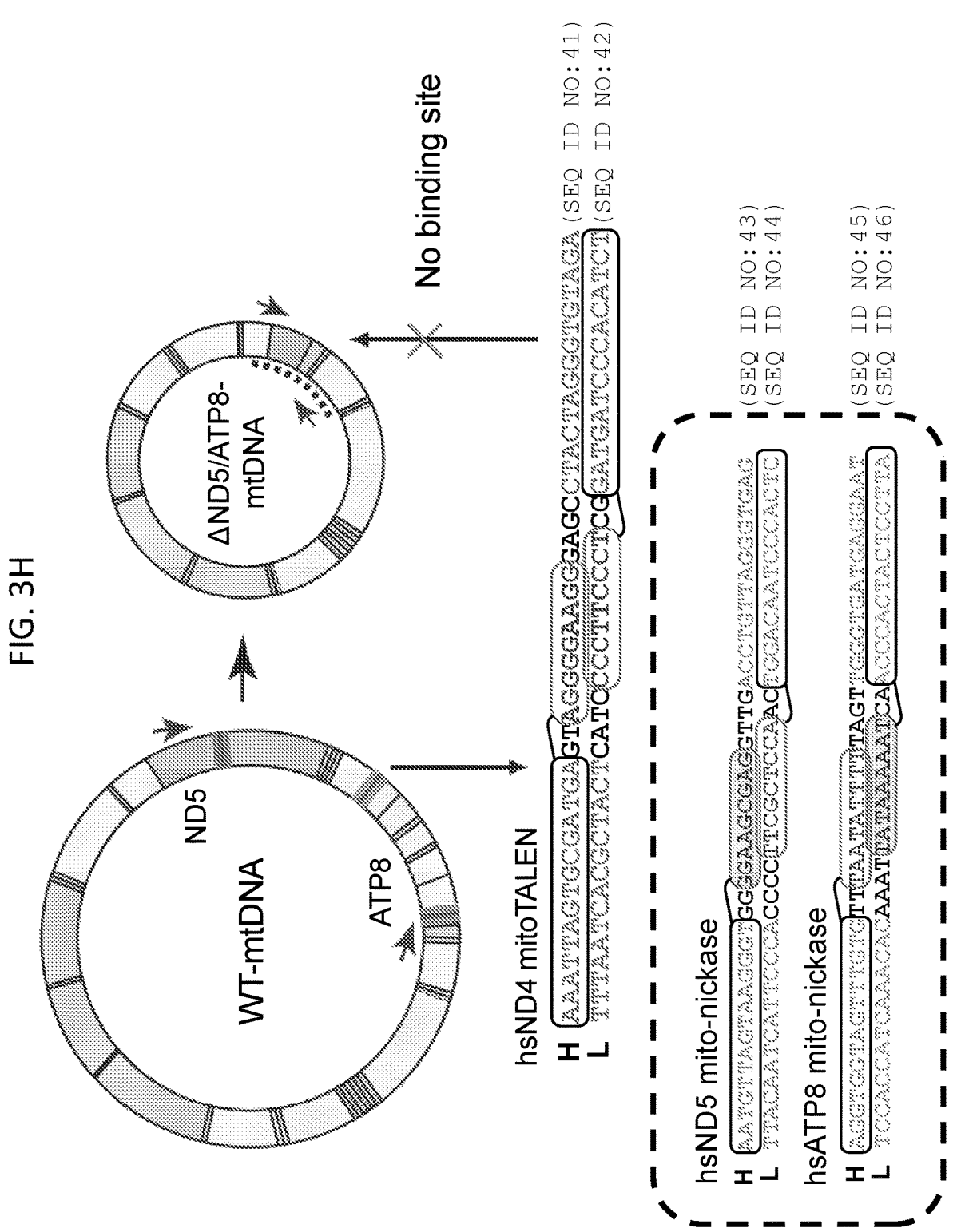
Figure 3J:
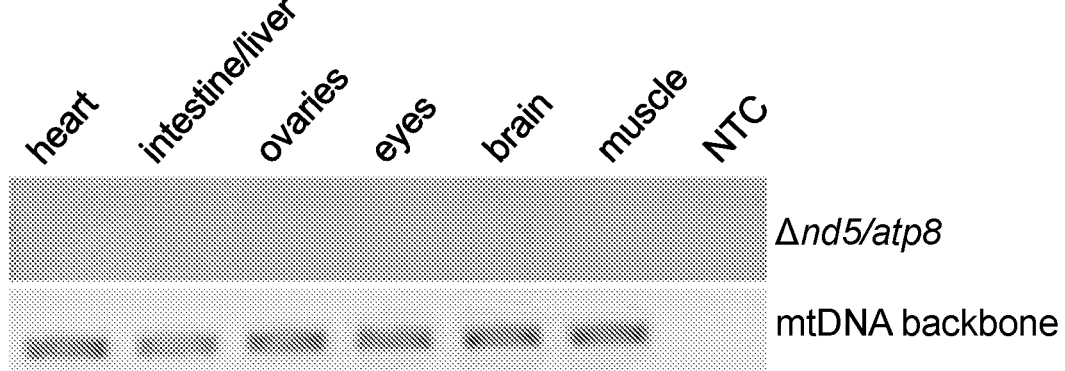
Figure 3J:
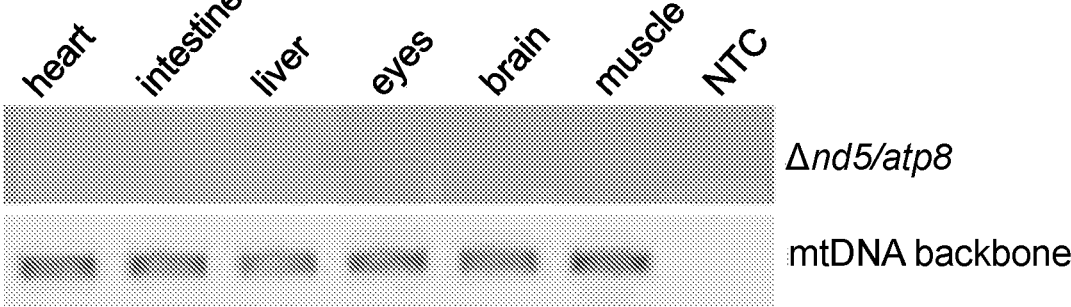
Figure 3J:
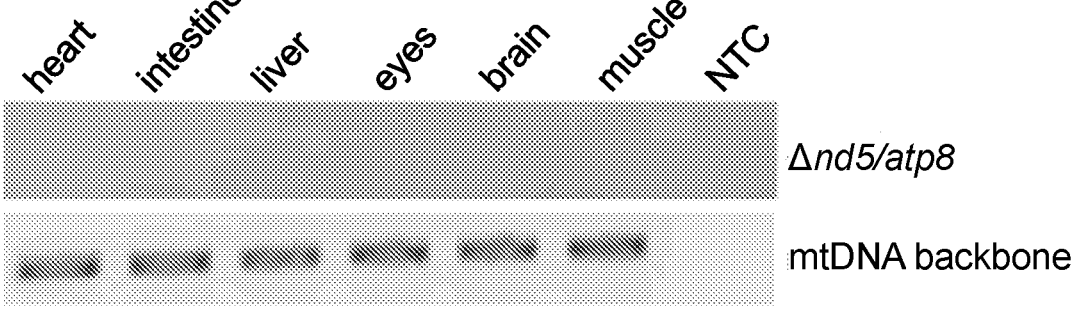
Figure 3K:
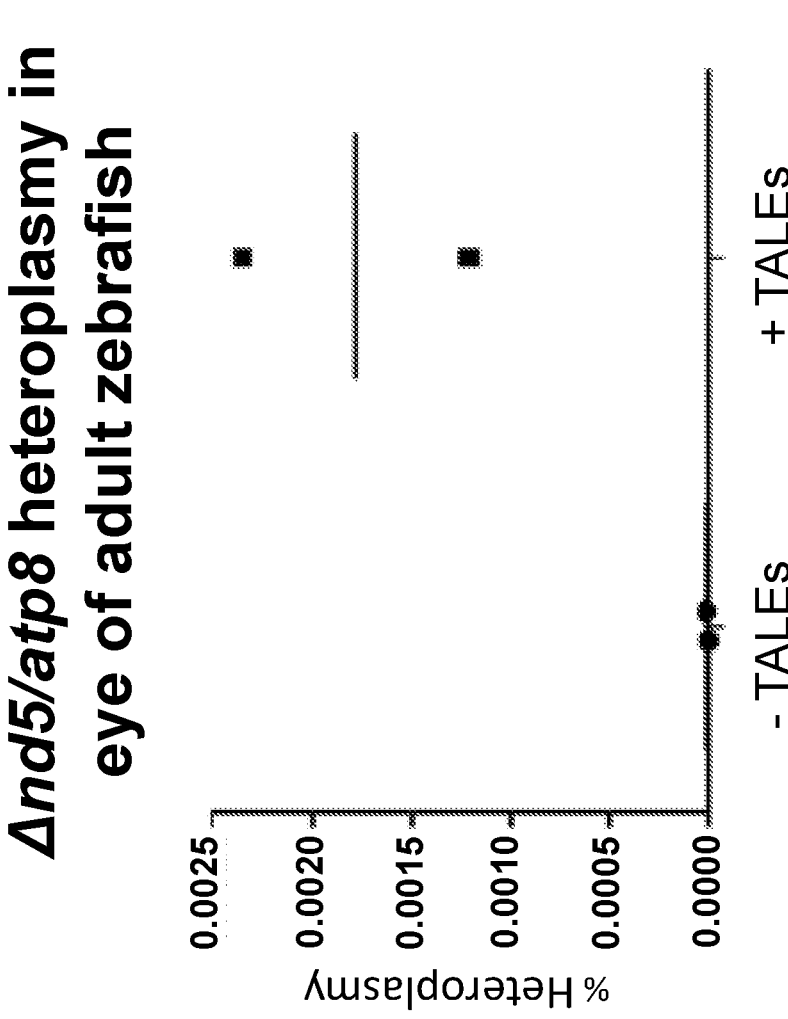

To determine whether nucleases might be effective to selectively target WT-mtDNA and preferentially enrich for the seeded Δnd5/atp8-mtDNA genomes induced by nickases, a nuclease (mitoTALE) was designed against nd4, located between the nd5 and atp8 mito-nickases target sites in WT-mtDNA (FIG. 3A). The simultaneous delivery of the nd5 mito-nickase, atp8 mito-nickase, and the nd4 mitoTALE nuclease resulted in over 90% of injected animals harboring deletions (FIG. 3B). These deletions were similar in sequence to nickase-injected animals (FIGS. 3E, 3F, and 3G). Using this approach, targeted deletions also were generated in human 293T cells (FIGS. 3D, 3H, and 3I). Notably, the variability observed in zebrafish embryos was not seen in 293T mtDNA deletion products (FIGS. 3D, 3H, and 3I). Zebrafish deletions were stable for months in vivo, as demonstrated by analyses of adult fish tissues (FIGS. 3C, 3F, and 3G). Interestingly, deletions were maintained in both eye and brain tissues (FIGS. 3C, 3J, and 3K), organs where the KSS deletion can manifest with phenotypic consequences for humans (DiMauro and Hirano, "Mitochondrial DNA Deletion Syndromes," in GENEREVIEWS® [internet], Adam, Ardinger, Pagon, et al., Eds., Seattle, WA, University of Washington, Seattle, pp. 1993-2019, 2003 (updated 2011); available online at ncbi.nlm.nih.gov/books/NBK1203/). Notably, deletions were not detected in out-crossed embryos of female fish that maintained deletions in their fins, nor were they detected in the ovaries of females that were positive for deletions in brain and eye tissue (FIG. 3C). Deletions also were observed after nuclease-alone treatment for zebrafish (FIG. 3B), but not for 293T cells (FIG. 3D). This could be due to the inefficiency of TALE transfection, as human cells require multi-plasmid transfection, but zebrafish can be directly microinjected. Alternatively or in addition, this could also be the result of differences between species-specific, double-strand break repair, or differences between a developing vertebrate embryo in vivo and human embryonic kidney cells in vitro.

Figure 4B:
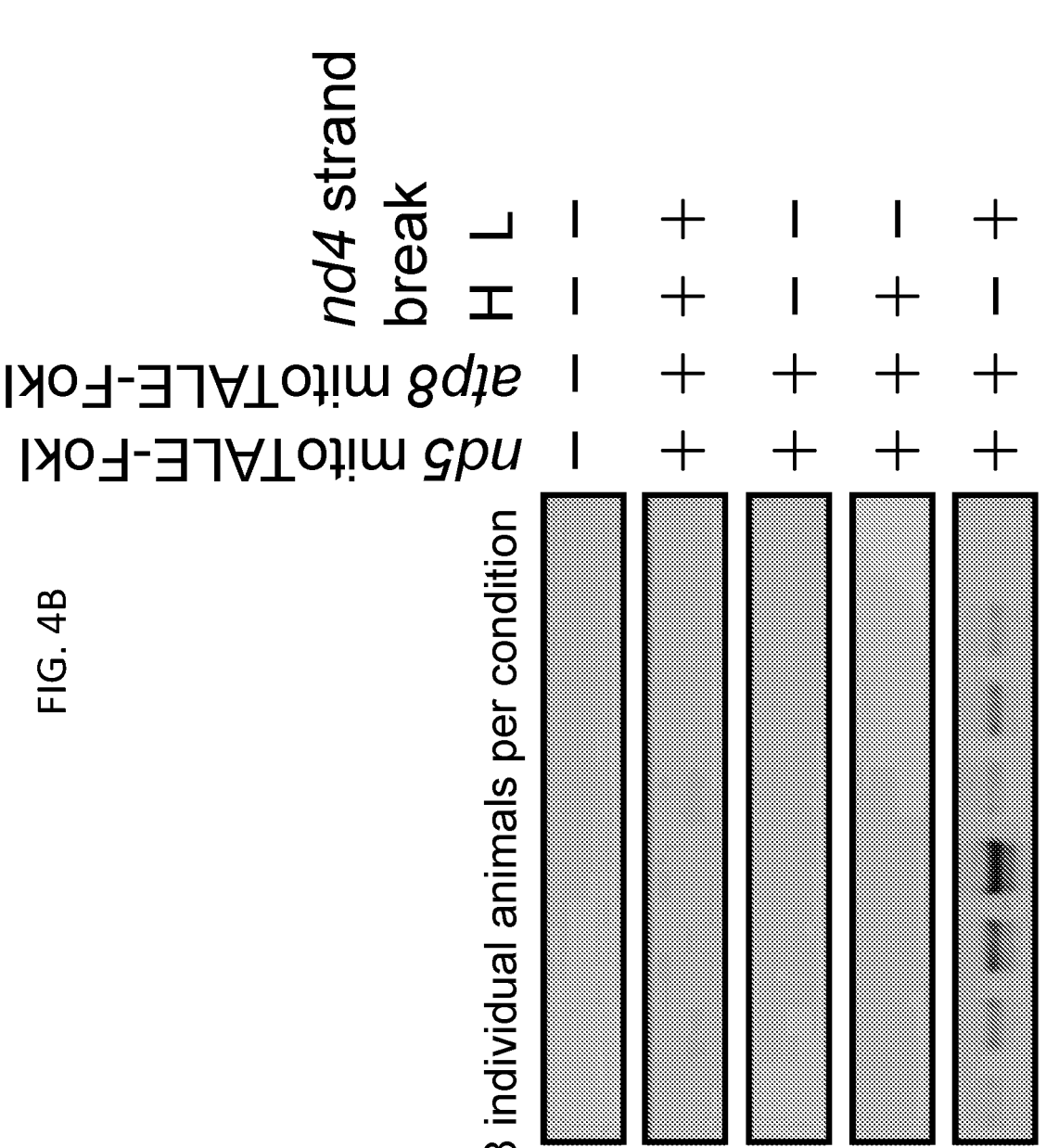
Figure 4C:
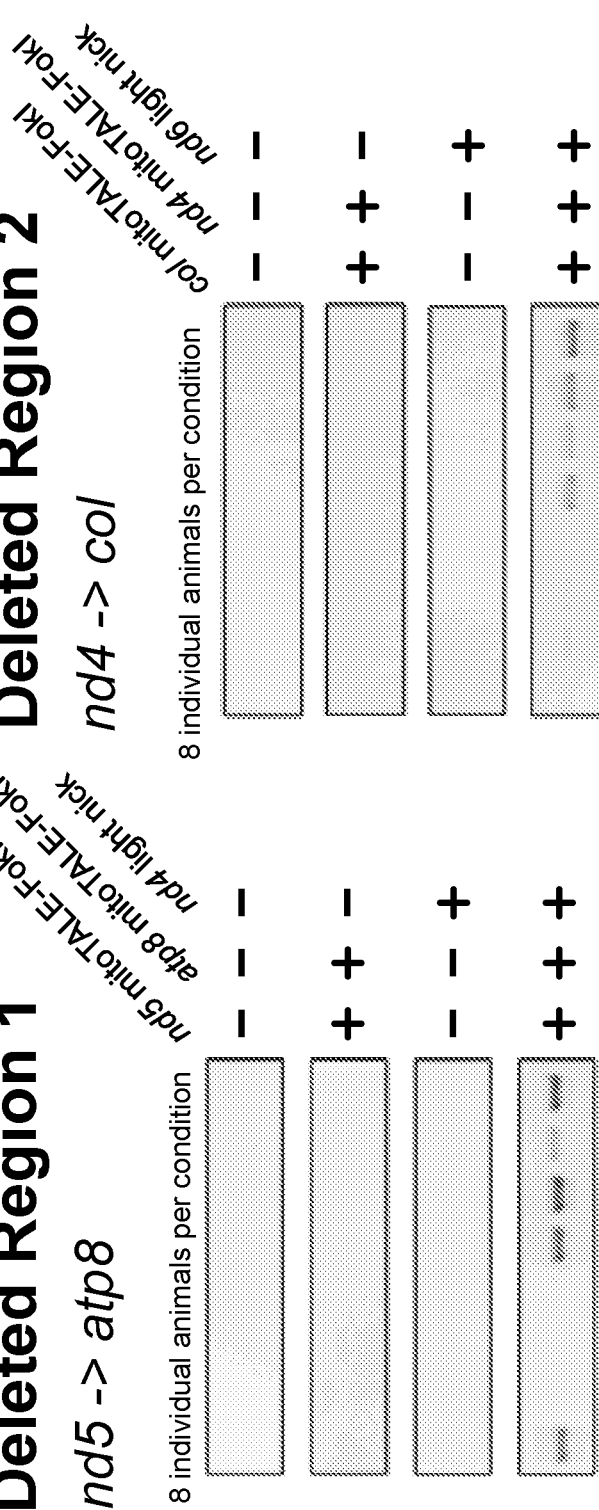
Figure 4D:
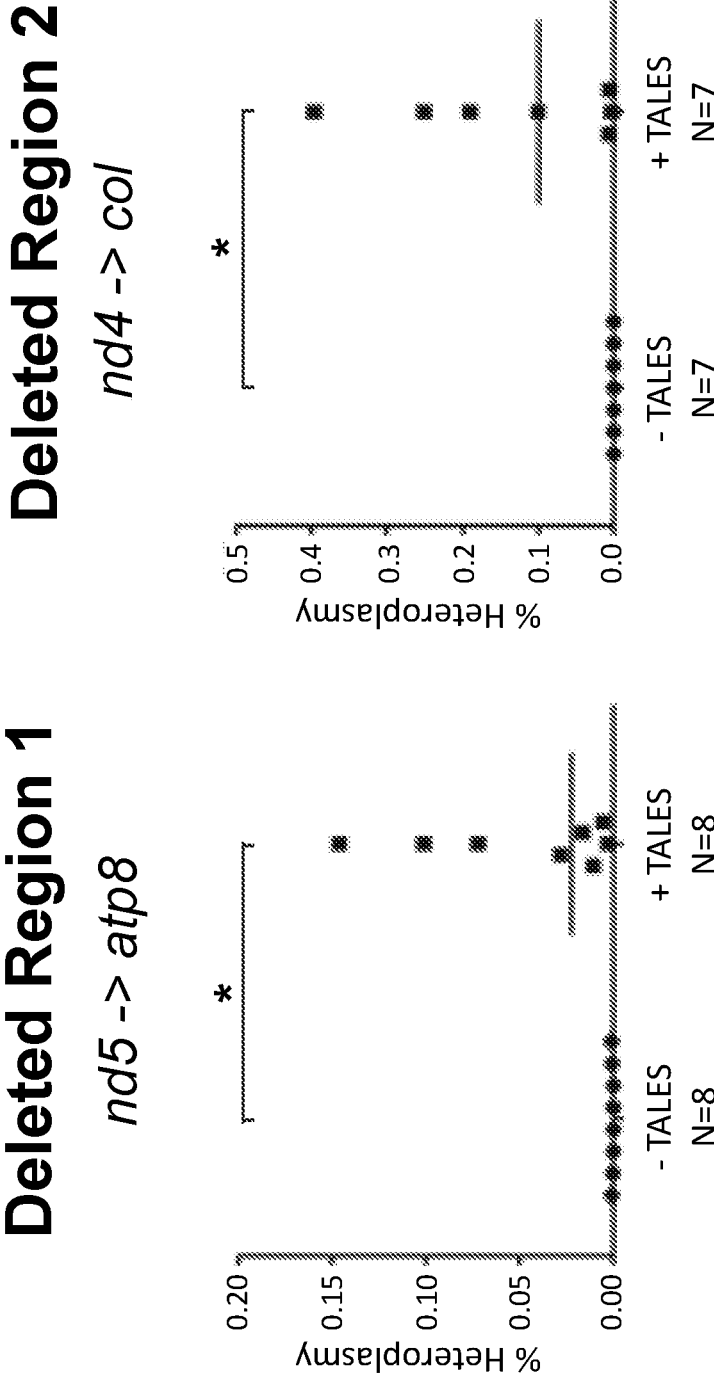
Figure 4F:
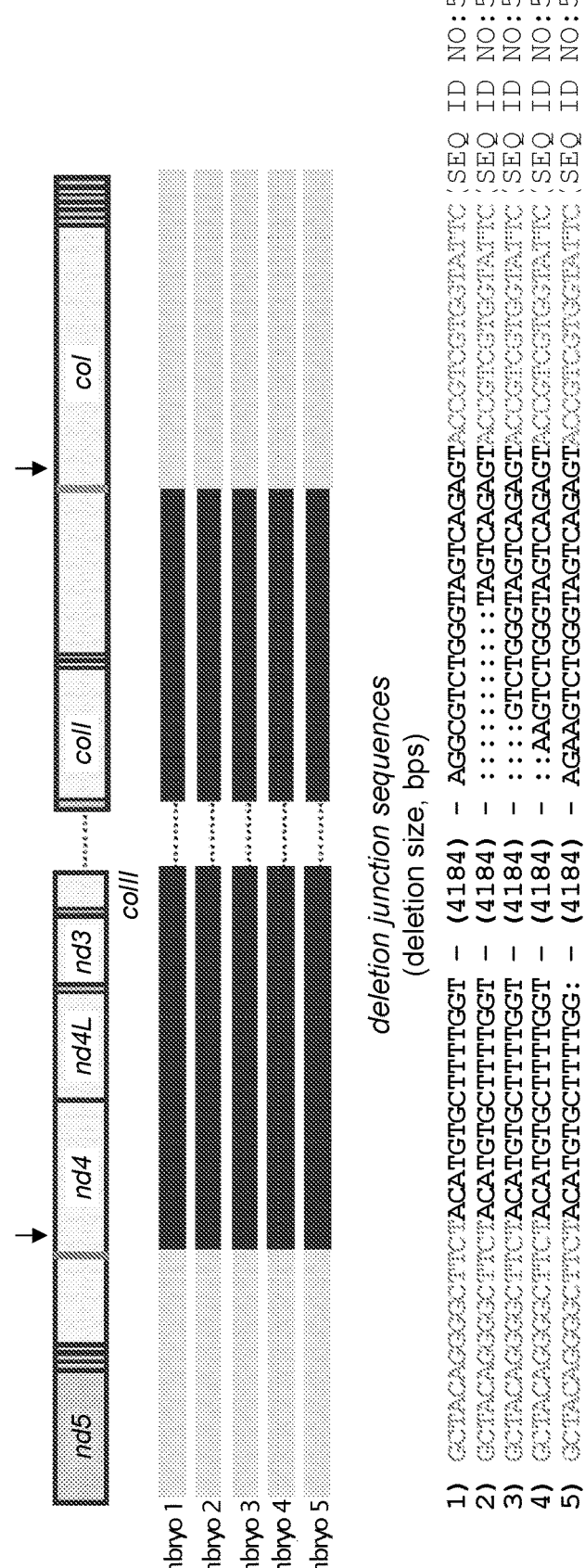

Deletions made using nickases did not usually fall within the predicted nick site, and at times were positioned just outside the TALE binding domains (FIGS. 1E, 2D, and 3E). This observation, along with the strong enhancement of mtDNA programming through the inclusion of mitoTALE nucleases (FIG. 3B), suggested the potential for a novel molecular repair process. To test the role of nickases in mediating mtDNA programming, drop-out experiments were conducted by sequentially removing each component of the nickase. Surprisingly, each flanking mitoTALE-nickase could be simplified into a single mitoTALE arm (FIG. 4A), so long as a nick was provided on the intervening mtDNA light strand (FIG. 4B). The resulting deletions were reproducible, with single-nucleotide specificity noted (FIG. 4C). Such reduced complexity of outcomes enabled the use of droplet digital PCR (ddPCR) to quantify mtDNA heteroplasmy across multiple embryos (FIG. 4D). In a single seed step, a range of 1 in 2000 to 1 in 250 mtDNA molecules were altered (FIG. 4D). To confirm that this effect applies to other regions of the mtDNA genome, a second deletion was generated between coI and nd4 (FIG. 4C), resulting in low complexity deletions with high precision at the nucleotide level (FIGS. 4E and 4F).

Figure 4G:
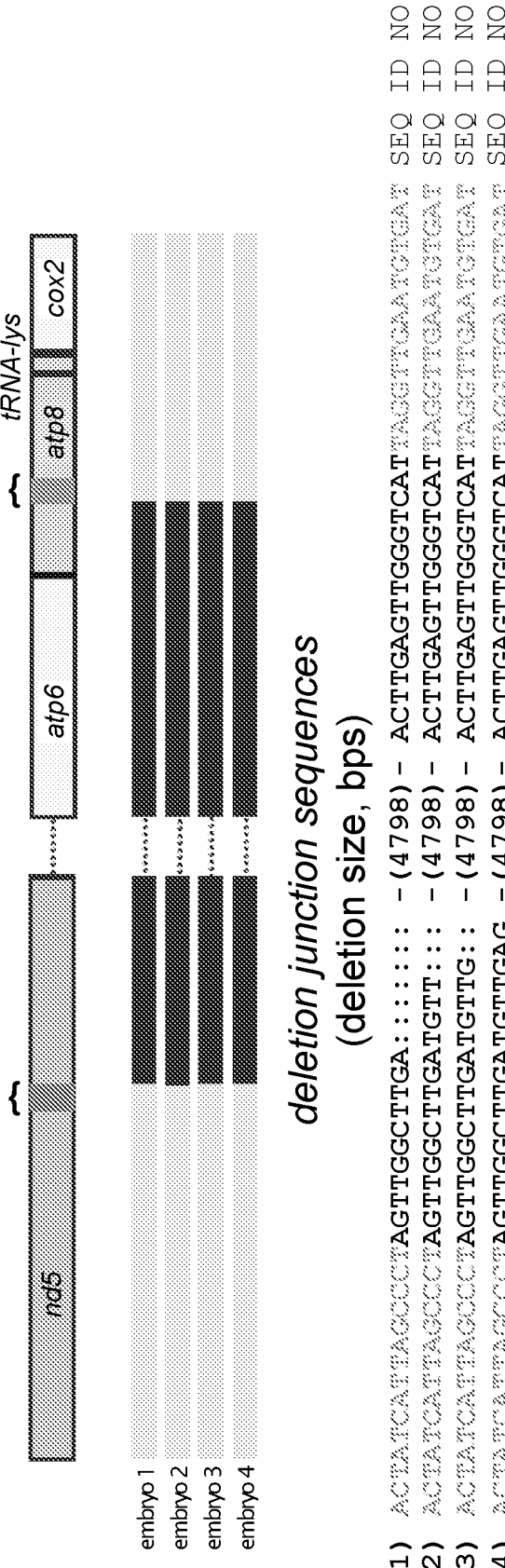
Figure 4H:
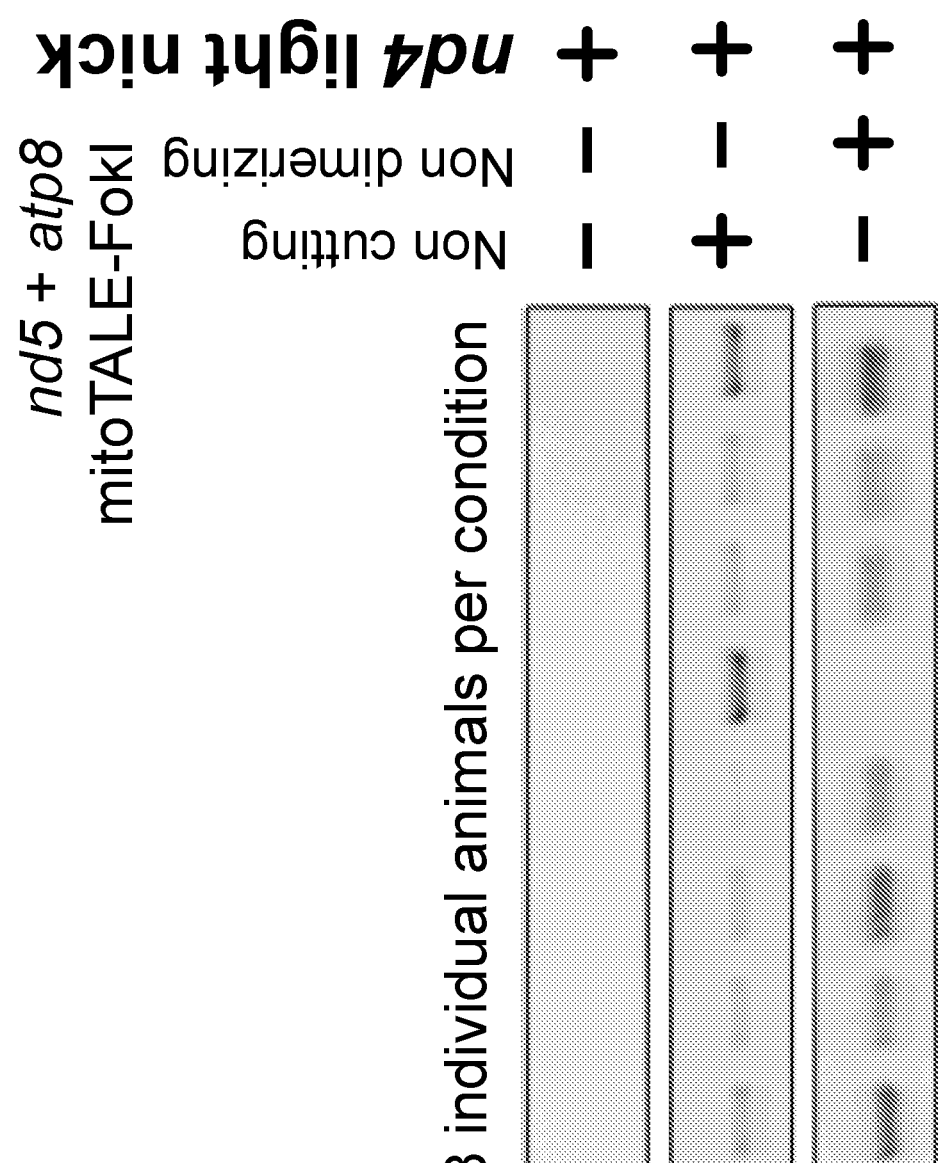
Figure 4I:
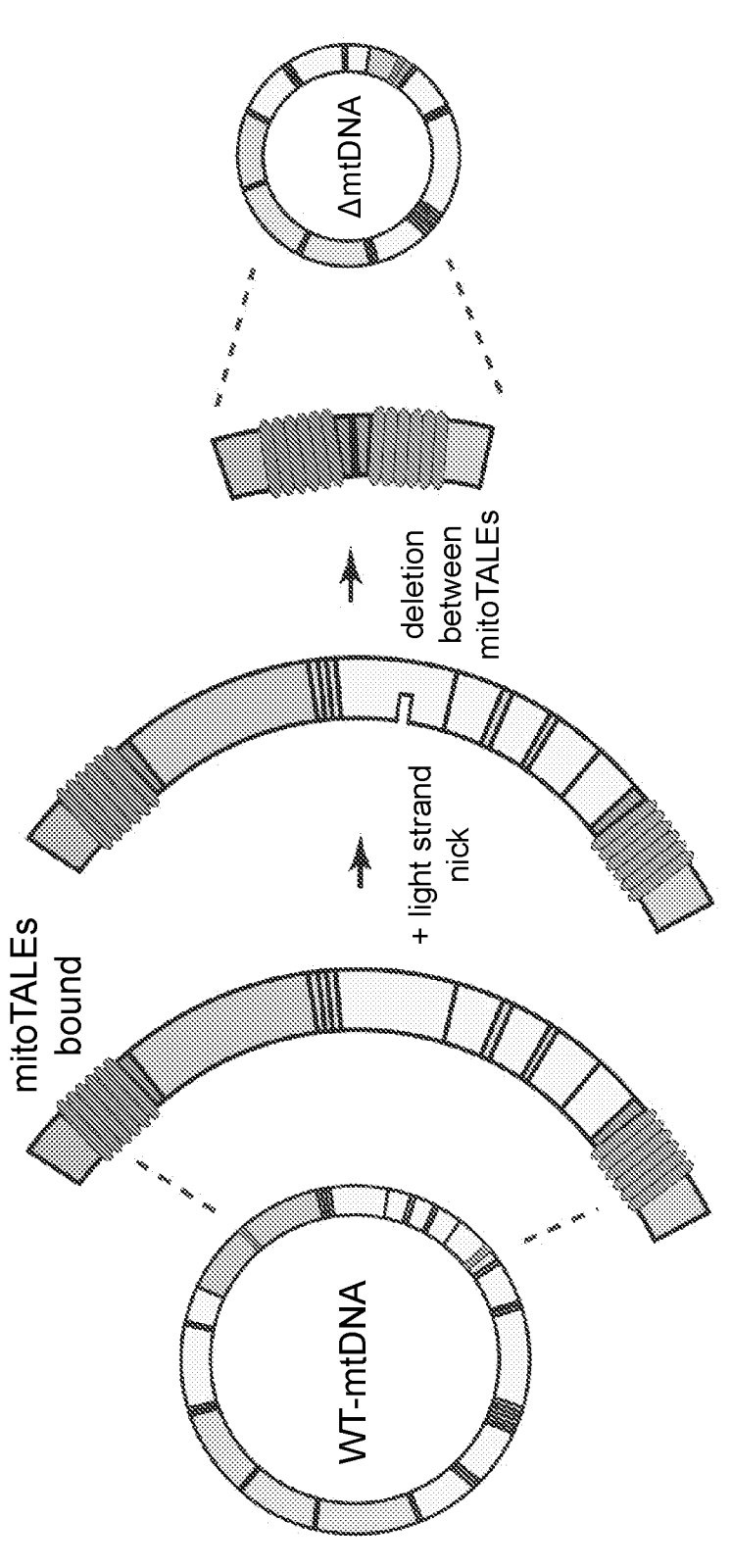

The naturally occurring 4977 bp deletion in human mtDNA has been reported to result from an unusual mechanism involving replication slippage around short sequence repeats that flank the deletion breakpoint (Phillips et al., Mol. Cell 65:527-538.e6, 2017). The results described herein suggest an alternative mechanism, as no apparent sequence repeats flanking de novo mtDNA deletions were noted in the induced mtDNA deletions that would be indicative of replication slippage or microhomology-mediated end joining break repair (Tadi et al., Mol. Biol. Cell, 2015, doi:10.1091/mbc.E15-05-0260). Nicking the mtDNA heavy-strand adjacent to one of the repeat sequences reportedly enriches the 'common deletion' observed in humans. However, the inverse was noted here: by nicking the mtDNA light-strand, designer mtDNA variants were generated (FIG. 4B). Additionally, no loss of activity was found when the cutting or dimerization ability of the terminal TALE-FokI proteins was eliminated (FIG. 4H). This finding, combined with sequence data confirming that deletions were made adjacent to the TALE target sequence (FIGS. 4E, 4F, and 4G), suggested that the targeted mtDNA binding proteins acted as a blockade to mitochondrial mtDNA machinery that is triggered by nicking the light strand. Although the precise nature of the underlying mechanism of induced mtDNA deletions is still to be elaborated, the requirement for terminal targeting proteins surrounding an intervening light strand nick suggests a "block and nick" working model for mtDNA targeted deletions (FIG. 4I).

Figure 5:
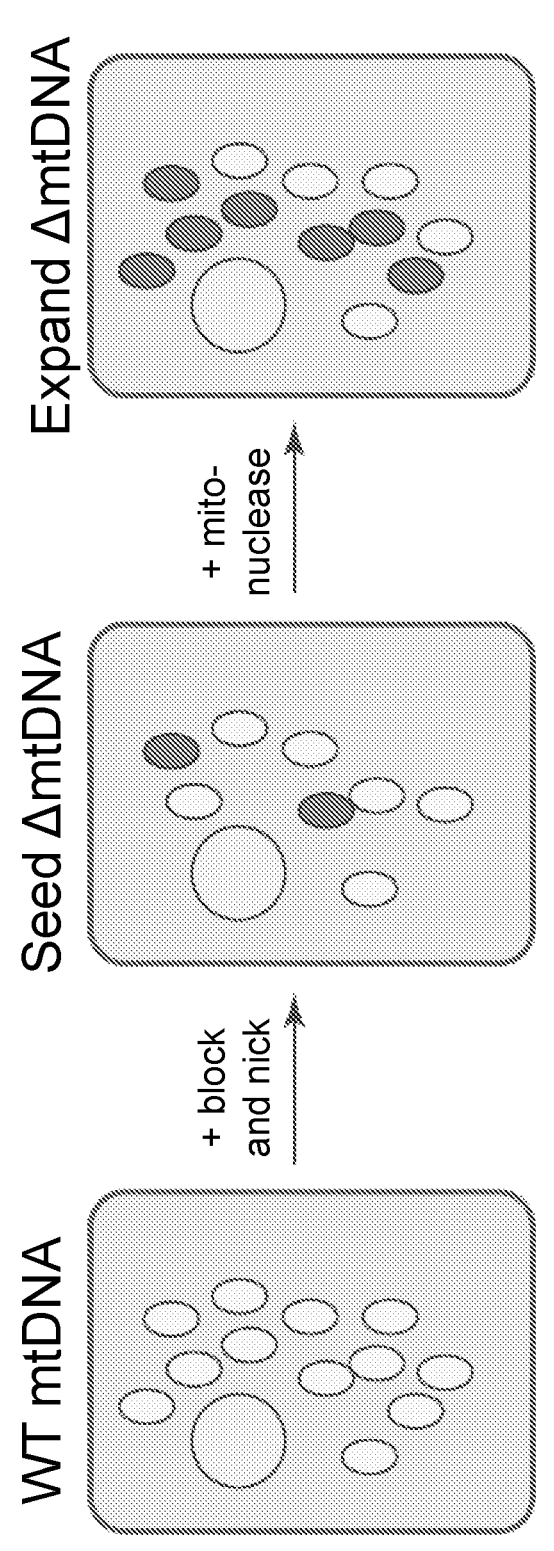
FIG. 5 is a schematic of a cell- and tissue-level mtDNA population engineering toolkit using a "seed and expand" method. Targeted deletions are seeded in the mitochondrial network using targeted block and nick technology. These designer mitochondrial genomes are separately expanded through heteroplasmic shift from targeted mito-nucleases.

The ability to precisely manipulate the mitochondrial genome is critical to understanding human disease and the biology of this complex organelle. Mitochondrial gene editing can be approached as a population genetics problem as thousands of mtDNA genomes are found within each cell. Thus, the "block and nick" mutation process described herein can address the first step of mtDNA genome manipulation by 'seeding' mtDNA sequences that harbor desired variants (FIG. 5). Although only low initial heteroplasmy levels may result from this initial seed step, elucidation of the mechanism used to generate these low-level, high-precision deletions may increase the yield of mtDNA-edited products. The subsequent ability to use specific nucleases to drive heteroplasmy levels based on unique nucleotide sequence also provides a viable, currently practical approach to expand mtDNA deletions to biologically significant heteroplasmy levels (FIG. 5). Such an approach may enable the tunable production of cells with differential heteroplasmy levels to recapitulate phenotypes found in human disease, a critical phenomenon known as the threshold effect (Sciacco et al., Hum. Mol. Genet. 3:13-19, 1994; Wallace and Chalkia, Cold Spring Harb. Perspect. Biol. 5:a021220-a021220, 2013; and Stewart and Chinnery, Nat. Rev. Genet. 16:530-542, 2015). Similarly, the development of complex in vivo animal models that mirror human disease (from zebrafish to mammals) may well be possible through the temporal or spatial (organ-specific) regulation of mitoTALE nucleases or other targeted nucleases after a one-time delivery of "block and nick" reagents to seed targeted mtDNA deletions in the embryo, as conducted here in the zebrafish test system. The system described herein is believed to be the first user-guided system to address direct sequence modification of mtDNA de novo. These findings will likely accelerate mitochondria research and lead to insights and improved therapies for mtDNA disease.

TABLE 1

| | | Left (5'-3') (SEQ ID NO:) | Right (5'-3') (SEQ ID NO:) |
|---|---|---|---|
| | | TALE mtDNA binding targets | |
| zebrafish | nd4 mito-nickase (1) | AAGTTCTGGTTTTAA (64) | TTACACCTAATTCCT (65) |
| | nd4 mito-nickase (2) | ACGAGTTAGAAGCAT (66) | GACTAAAATGAACCT (67) |
| | nd5 mito-nickase | GCTAGATGTGGTTGG (68) | AGGGCTAATGATAGT (69) |
| | atp8 mito-nickase | TAGGTTGAATGTGAT (70) | TCCTTACTATTATTC (71) |
| | nd4 mitoTALE nuclease | CGGGTAATAATGATT (72) | TATATTCGAAGCTAC (73) |
| | nd4 TALE-FokI | AGAAGCCCCTGTAGC (74) | |
| | coI TALE-FokI | ACCGTCGTGGTATTC (75) | |
| | atp6 mito-nickase | CGTACCCCTAAAGCT (76) | CGAAACAATTAGCTT (77) |
| human | hsND5 mito-nickase | AATGTTAGTAAGGGT (78) | CTCACCCTAACAGGT (79) |
| | hsATP8 mito-nickase | AGGTGGTAGTTTGTG (80) | ATTCCTCATCACCCA (81) |
| | hsND4 mitoTALE nuclease | AAATTAGTGCGATGA (82) | TCTACACCCTAGTAG (83) |

TABLE 2

| | | Forward (5'-3') (SEQ ID NO:) | Reverse (5'-3') (SEQ ID NO:) |
|---|---|---|---|
| | | Primers and Probes | |
| zebrafish | nd4 deletion bridge PCR primers | CCAGGTGATGAATAAGGCGATT GAGGT (84) | GGTCCGCCCGCCTACCATTTT C (85) |
| | nd5→atp8 deletion bridge PCR primers | GCAATAATGCTTCCTCAGGCAAG CCGT (86) | GACGCGGTACCCGGACGATT AAACCA (87) |
| | nd4→coI deletion bridge PCR primers | CGGATGAGGTTAGTCCGTGGGC GA (88) | ACCCGAGCATACTTCACATCC GCC (89) |
| | mtDNA control primers (zebrafish MT-TL1) | TGATTGTAACAGTCCTCGGGGG CC (90) | AGGATCGGAAAAAGGGGGCC CATAC (91) |
| | nd5 → atp8 deletion ddPCR primers | TGCTAGATGTGGTTGGTTTAGGC (92) | CATTCAACCTAATGACCCAAC TCAAG (93) |
| | nd5→atp8 deletion ddPCR probe (FAM) | TTGCTACTATCATTAGCCCTAGTT GGCTTG (94) | |

TABLE 2-continued

| | | Forward (5'-3') (SEQ ID NO:) | Reverse (5'-3') (SEQ ID NO:) |
|---|---|---|---|
| | nd4→ coI deletion ddPCR primers | GCACTGCCGCTAGAATTATAGAT CC (95) | TCTCACATTCTTCCCACAACA TTTCC (96) |
| | nd4→ coI deletion ddPCR probe (FAM) | TACCGTCGTGGTATTCCTGCTAA ACC (97) | |
| | nd5→ atp8 deletion ddPCR (eye) primers | ATTCAACCTAATGACCCAACTCA AG (98) | GCCCCTGAGCATAAGAATAAT ATGG (99) |
| | nd5→ atp8 deletion ddPCR (eye) primers (FAM) | TCCACATCTGCACTCACGCTT (100) | |
| | nd1 ddPCR primers | CCCCTCTGTAAGATCGAACGG (101) | ACTTCCACTATGACCATTAGC CA (102) |
| | nd1 ddPCR probe (HEX) | TCGGTTTGTTTCTGCCAGCGTTG (103) | |
| human | nd5→ atp8 deletion bridge PCR primers | GCGATGGAGGTAGGATTGGTGC TGTGG (104) | CTCATGAGCTGTCCCCACATT AGGCTT (105) |
| | mtDNA control primers (human MT-TL1) | GAGTTTTATGGCGTCAGCGA (106) | GGACAAGAGAAATAAGGCCT ACTTC (107) |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for editing mitochondrial DNA (mtDNA) within a cell, wherein the method comprises introducing, into the cell:

(a) a DNA nicking enzyme targeted to a mtDNA sequence to be deleted;

(b) a first DNA binding component targeted to a sequence adjacent to the 5' end of the mtDNA sequence to be deleted; and (c) a second DNA binding component targeted to a sequence adjacent to the 3' end of the mtDNA sequence to be deleted, wherein:

(i) binding of said first DNA binding component to said sequence adjacent to the 5' end of the mtDNA sequence to be deleted does not result in mtDNA cleavage adjacent to the 5' end of the mtDNA sequence to be deleted, or (ii) binding of said second DNA binding component to said sequence adjacent to the 3' end of the mtDNA sequence to be deleted does not result in mtDNA cleavage adjacent to the 3' end of the mtDNA sequence to be deleted, or (iii) binding of said first DNA binding component to said sequence adjacent to the 5' end of the mtDNA sequence to be deleted does not result in mtDNA cleavage adjacent to the 5' end of the mtDNA sequence to be deleted and wherein binding of said second DNA binding component to said sequence adjacent to the 3' end of the mtDNA sequence to be deleted does not result in mtDNA cleavage adjacent to the 3' end of the mtDNA sequence to be deleted, wherein the DNA nicking enzyme generates a single strand nick within the mtDNA sequence to be deleted, wherein the mtDNA sequence between the target sequence for the first DNA binding component and the target sequence for the second DNA binding component is deleted, and wherein the deleted mtDNA sequence is between 1200 and 5200 base pairs in length.

2. The method of claim 1, wherein the DNA nicking enzyme is a dimeric nickase comprising a pair of monomers, wherein each monomer comprises:

(a) a first portion comprising a MTS;

(b) a second portion comprising an amino acid sequence targeting the DNA nicking enzyme to the sequence to be deleted from the mtDNA; and (c) a third portion comprising a nuclease domain, wherein one monomer of the pair comprises an unmodified nuclease domain and the other monomer of the pair comprises a modified nuclease domain, wherein, when the monomers are bound to their target sequences within the mtDNA sequence to be deleted, the nuclease domains of the monomers form a dimer that generates a single strand nick within the mtDNA sequence to be deleted.

3. The method of claim 2, wherein the unmodified nuclease domain comprises a FokI endonuclease domain, and wherein the modified nuclease domain comprises a modified FokI endonuclease domain.

4. The method of claim 3, wherein the modified FokI endonuclease domain comprises an aspartic acid to alanine substitution compared to an unmodified FokI endonuclease domain.

5. The method of claim 2, wherein the MTS in each monomer is from an isocitrate dehydrogenase 2 gene.

6. The method of claim 2, wherein the second portion of each monomer comprises a transcriptional activator-like effector (TALE) backbone and a plurality of tandem repeat sequences comprising repeat variable dinucleotides (RVDs) that, in combination, bind to a target sequence within the mtDNA sequence to be deleted.

7. The method of claim 1, wherein:

the first DNA binding component is a polypeptide that comprises (i) a first portion comprising a MTS, and (ii) a second portion comprising an amino acid sequence targeting the first DNA binding component to the sequence adjacent to the 5' end of the mtDNA sequence to be deleted, wherein the first DNA binding component lacks a nuclease domain; and the second DNA binding component is a polypeptide that comprises (i) a first portion comprising a MTS, and (ii) a second portion comprising an amino acid sequence targeting the second DNA binding component to the sequence adjacent to the 3' end of the mtDNA sequence to be deleted, wherein the second DNA binding component lacks a nuclease domain.

8. The method of claim 7, wherein the MTS in the first and second DNA binding components is from an isocitrate dehydrogenase 2 gene, and wherein the second portion of the first DNA binding component comprises a TALE backbone and a plurality of tandem repeat sequences comprising RVDs that, in combination, bind to a target sequence adjacent to the 5' end of the mtDNA sequence to be deleted, and wherein the second portion of the second DNA binding component comprises a TALE backbone and a plurality of tandem repeat sequences comprising RVDs that, in combination, bind to a target sequence adjacent to the 3' end of the mtDNA sequence to be deleted.

9. The method of claim 1, wherein:

the first DNA binding component is a dimer comprising a pair of monomers, wherein each monomer is a polypeptide that comprises (i) a first portion comprising a MTS, (ii) a second portion comprising an amino acid sequence targeting the monomer to a sequence adjacent to the 5' end of the mtDNA sequence to be deleted, and (iii) a third portion comprising a nuclease domain, wherein one monomer of the pair comprises an unmodified nuclease domain and the other monomer of the pair comprises a modified nuclease domain; and the second DNA binding component is a polypeptide that comprises (i) a first portion comprising a MTS, and (ii) a second portion comprising an amino acid sequence targeting the second DNA binding component to the sequence adjacent to the 3' end of the mtDNA sequence to be deleted, wherein the second DNA binding component lacks a nuclease domain.

10. The method of claim 9, wherein the MTS in each monomer of the first and second DNA binding components is from an isocitrate dehydrogenase 2 gene, wherein the second portion of each monomer of the first DNA binding component comprises a TALE backbone and a plurality of tandem repeat sequences comprising RVDs that, in combination, bind to target sequences adjacent to the 5' end of the mtDNA sequence to be deleted, and wherein the second portion of each monomer of the second DNA binding component comprises a TALE backbone and a plurality of tandem repeat sequences comprising RVDs that, in combination, bind to target sequences adjacent to the 3' end of the mtDNA sequence to be deleted, and wherein the unmodified nuclease domain within the third portion of the first DNA binding component is a FokI endonuclease domain, and wherein the modified nuclease domain within the third portion of the first DNA binding component is a modified FokI endonuclease domain.

11. The method of claim 1, wherein:

the first DNA binding component is a polypeptide that comprises (i) a first portion comprising a MTS, and (ii) a second portion comprising an amino acid sequence targeting the first DNA binding component to the sequence adjacent to the 5' end of the mtDNA sequence to be deleted, wherein the first DNA binding component lacks a nuclease domain; and the second DNA binding component is a dimer comprising a pair of monomers, wherein each monomer is a polypeptide that comprises (i) a first portion comprising a MTS, (ii) a second portion comprising an amino acid sequence targeting the monomer to a sequence adjacent to the 3' end of the mtDNA sequence to be deleted, and (iii) a third portion comprising a nuclease domain, wherein one monomer of the pair comprises an unmodified nuclease domain and the other monomer of the pair comprises a modified nuclease domain.

12. The method of claim 11, wherein the MTS in each monomer of the first and second DNA binding components is from an isocitrate dehydrogenase 2 gene, wherein the second portion of each monomer of the first DNA binding component comprises a TALE backbone and a plurality of tandem repeat sequences comprising RVDs that, in combination, bind to target sequences adjacent to the 5' end of the mtDNA sequence to be deleted, and wherein the second portion of each monomer of the second DNA binding component comprises a TALE backbone and a plurality of tandem repeat sequences comprising RVDs that, in combination, bind to target sequences adjacent to the 3' end of the mtDNA sequence to be deleted, and wherein the unmodified nuclease domain within the third portion of the second DNA binding component is a FokI endonuclease domain, and wherein the modified nuclease domain within the third portion of the second DNA binding component is a modified FokI endonuclease domain.

13. The method of claim 1, wherein the cell is a eukaryotic cell.

14. The method of claim 13, wherein the eukaryotic cell is within a eukaryotic organism.

15. The method of claim 14, wherein the introducing comprises injecting the DNA nicking enzyme and the first and second DNA binding components into the eukaryotic organism, or wherein the introducing comprises injecting nucleic acid molecules encoding the DNA nicking enzyme and the first and second DNA binding components into the eukaryotic organism.

16. The method of claim 1, wherein the cell is in vitro.

17. The method of claim 16, wherein the introducing comprises transforming nucleic acid molecules encoding the DNA nicking enzyme and the first and second DNA binding components into the cell.

* * * * *

SEQUENCE LISTING

<160> NUMBER OF SEQ ID NOS: 112

<210> SEQ ID NO 1
<211> LENGTH: 43
<212> TYPE: PRT
<213> ORGANISM: Danio rerio

<400> SEQUENCE: 1

Met Ala Gly Tyr Leu Lys Val Leu Ser Ser Leu Ser Arg Ser Ala Ala
1               5                   10                  15

-continued

```
Thr Leu Ser Lys Ser Pro Ala Val Leu Ala Pro Ala Cys Gln Ser Leu
        20                  25                  30

Gln Gln Arg Asn Tyr Ala Asp Lys Arg Ile Gln
        35                  40

<210> SEQ ID NO 2
<211> LENGTH: 45
<212> TYPE: DNA
<213> ORGANISM: Danio rerio

<400> SEQUENCE: 2
aagttctggt tttaatataa gtaagatgat aggaattagg tgtaa                45

<210> SEQ ID NO 3
<211> LENGTH: 45
<212> TYPE: DNA
<213> ORGANISM: Danio rerio

<400> SEQUENCE: 3
ttacacctaa ttcctatcat cttacttata ttaaaaccag aactt               45

<210> SEQ ID NO 4
<211> LENGTH: 45
<212> TYPE: DNA
<213> ORGANISM: Danio rerio

<400> SEQUENCE: 4
acgagttaga agcatttcac cctgtatccg aggttcattt tagtc               45

<210> SEQ ID NO 5
<211> LENGTH: 45
<212> TYPE: DNA
<213> ORGANISM: Danio rerio

<400> SEQUENCE: 5
gactaaaatg aacctcggat acagggtgaa atgcttctaa ctcgt               45

<210> SEQ ID NO 6
<211> LENGTH: 40
<212> TYPE: DNA
<213> ORGANISM: Artificial Sequence
<220> FEATURE:
<223> OTHER INFORMATION: mutant sequence

<400> SEQUENCE: 6
cacataagtt ctggttttaa aggcaattaa aaaactgttt                     40

<210> SEQ ID NO 7
<211> LENGTH: 40
<212> TYPE: DNA
<213> ORGANISM: Artificial Sequence
<220> FEATURE:
<223> OTHER INFORMATION: mutant sequence

<400> SEQUENCE: 7
cacataagtt ctggttttaa ggcaattaca aagctgttta                     40

<210> SEQ ID NO 8
<211> LENGTH: 40
<212> TYPE: DNA
<213> ORGANISM: Artificial Sequence
<220> FEATURE:
<223> OTHER INFORMATION: mutant sequence
```

<400> SEQUENCE: 8
cctcggtgag tgaggggggct gtggataaac ttattgactc                    40

<210> SEQ ID NO 9
<211> LENGTH: 40
<212> TYPE: DNA
<213> ORGANISM: Artificial Sequence
<220> FEATURE:
<223> OTHER INFORMATION: mutant sequence

<400> SEQUENCE: 9
tcattaagag atgttctcgg ggccgccttg ggctcattcg                    40

<210> SEQ ID NO 10
<211> LENGTH: 40
<212> TYPE: DNA
<213> ORGANISM: Artificial Sequence
<220> FEATURE:
<223> OTHER INFORMATION: mutant sequence

<400> SEQUENCE: 10
tcattaagag atgttctcgg ccgccttggg ctcattcgta                    40

<210> SEQ ID NO 11
<211> LENGTH: 40
<212> TYPE: DNA
<213> ORGANISM: Artificial Sequence
<220> FEATURE:
<223> OTHER INFORMATION: mutant sequence

<400> SEQUENCE: 11
tgtaaagtca ttaagagatg ggccgccttg ggctcattcg                    40

<210> SEQ ID NO 12
<211> LENGTH: 40
<212> TYPE: DNA
<213> ORGANISM: Artificial Sequence
<220> FEATURE:
<223> OTHER INFORMATION: mutant sequence

<400> SEQUENCE: 12
tgtaaagtca ttaagagatg gccgccttgg gctcattcgt                    40

<210> SEQ ID NO 13
<211> LENGTH: 40
<212> TYPE: DNA
<213> ORGANISM: Artificial Sequence
<220> FEATURE:
<223> OTHER INFORMATION: mutant sequence

<400> SEQUENCE: 13
actcttcctc ggtgagtgag ggggctgtgg ataaacttat                    40

<210> SEQ ID NO 14
<211> LENGTH: 40
<212> TYPE: DNA
<213> ORGANISM: Artificial Sequence
<220> FEATURE:
<223> OTHER INFORMATION: mutant sequence

<400> SEQUENCE: 14
ggtgtaaagt cattaagaga ggccgccttg ggctcattcg                    40

<210> SEQ ID NO 15
<211> LENGTH: 40

-continued

```
<212> TYPE: DNA
<213> ORGANISM: Artificial Sequence
<220> FEATURE:
<223> OTHER INFORMATION: mutant sequence

<400> SEQUENCE: 15
acagcatcat tgtaagtggg gttattaagt tgatctcctc                              40

<210> SEQ ID NO 16
<211> LENGTH: 45
<212> TYPE: DNA
<213> ORGANISM: Danio rerio

<400> SEQUENCE: 16
gctagatgtg gttggtttag gccaattgct actatcatta gccct                       45

<210> SEQ ID NO 17
<211> LENGTH: 45
<212> TYPE: DNA
<213> ORGANISM: Danio rerio

<400> SEQUENCE: 17
agggctaatg atagtagcaa ttggcctaaa ccaaccacat ctagc                       45

<210> SEQ ID NO 18
<211> LENGTH: 45
<212> TYPE: DNA
<213> ORGANISM: Danio rerioi

<400> SEQUENCE: 18
taggttgaat gtgattaatg attttggttg gaataatagt aagga                       45

<210> SEQ ID NO 19
<211> LENGTH: 45
<212> TYPE: DNA
<213> ORGANISM: Danio rerio

<400> SEQUENCE: 19
tccttactat tattccaacc aaaatcatta atcacattca accta                       45

<210> SEQ ID NO 20
<211> LENGTH: 40
<212> TYPE: DNA
<213> ORGANISM: Artificial Sequence
<220> FEATURE:
<223> OTHER INFORMATION: mutant sequence

<400> SEQUENCE: 20
gccctagttg gcttgatgtt agttgggtca ttaggttgaa                             40

<210> SEQ ID NO 21
<211> LENGTH: 40
<212> TYPE: DNA
<213> ORGANISM: Artificial Sequence
<220> FEATURE:
<223> OTHER INFORMATION: mutant sequence

<400> SEQUENCE: 21
gccctagttg gcttgatgtt attttggttg gaataatagt                             40

<210> SEQ ID NO 22
<211> LENGTH: 41
<212> TYPE: DNA
<213> ORGANISM: Artificial Sequence
<220> FEATURE:
```

-continued

<223> OTHER INFORMATION: mutant sequence

<400> SEQUENCE: 22
attagcccta gttggcttga ggtggtcagg taagcaccaa g                            41

<210> SEQ ID NO 23
<211> LENGTH: 40
<212> TYPE: DNA
<213> ORGANISM: Artificial Sequence
<220> FEATURE:
<223> OTHER INFORMATION: mutant sequence

<400> SEQUENCE: 23
tggtttaggc caattgctac attttggttg gaataatagt                              40

<210> SEQ ID NO 24
<211> LENGTH: 40
<212> TYPE: DNA
<213> ORGANISM: Artificial Sequence
<220> FEATURE:
<223> OTHER INFORMATION: mutant sequence

<400> SEQUENCE: 24
tggtttaggc caattgctac gggtggtcgg taagcaccaa                              40

<210> SEQ ID NO 25
<211> LENGTH: 40
<212> TYPE: DNA
<213> ORGANISM: Artificial Sequence
<220> FEATURE:
<223> OTHER INFORMATION: mutant sequence

<400> SEQUENCE: 25
ttggtttagg ccaattgcta cccgcagatt tcagagcatt                              40

<210> SEQ ID NO 26
<211> LENGTH: 40
<212> TYPE: DNA
<213> ORGANISM: Artificial Sequence
<220> FEATURE:
<223> OTHER INFORMATION: mutant sequence

<400> SEQUENCE: 26
atgtggttgg tttaggccaa gggtggtcgg taagcaccaa                              40

<210> SEQ ID NO 27
<211> LENGTH: 40
<212> TYPE: DNA
<213> ORGANISM: Artificial Sequence
<220> FEATURE:
<223> OTHER INFORMATION: mutant sequence

<400> SEQUENCE: 27
atgtggttgg tttaggccaa ggtggtcggt aagcaccaag                              40

<210> SEQ ID NO 28
<211> LENGTH: 40
<212> TYPE: DNA
<213> ORGANISM: Artificial Sequence
<220> FEATURE:
<223> OTHER INFORMATION: mutant sequence

<400> SEQUENCE: 28
taagggctat tttcccgatg ttgggtcatt aggttgaatg                              40

-continued

```
<210> SEQ ID NO 29
<211> LENGTH: 45
<212> TYPE: DNA
<213> ORGANISM: Danio rerio

<400> SEQUENCE: 29
cgggtaataa tgattagtgt tgggataagt gtagcttcga atata                45

<210> SEQ ID NO 30
<211> LENGTH: 45
<212> TYPE: DNA
<213> ORGANISM: Danio rerio

<400> SEQUENCE: 30
tatattcgaa gctacactta tcccaacact aatcattatt acccg                45

<210> SEQ ID NO 31
<211> LENGTH: 40
<212> TYPE: DNA
<213> ORGANISM: Artificial Sequence
<220> FEATURE:
<223> OTHER INFORMATION: mutant sequence

<400> SEQUENCE: 31
tcttttgaga aaaatcctga attttggttg gaataatagt                      40

<210> SEQ ID NO 32
<211> LENGTH: 40
<212> TYPE: DNA
<213> ORGANISM: Artificial Sequence
<220> FEATURE:
<223> OTHER INFORMATION: mutant sequence

<400> SEQUENCE: 32
tggtttaggc caattgctac aggattataa atcagggttt                      40

<210> SEQ ID NO 33
<211> LENGTH: 40
<212> TYPE: DNA
<213> ORGANISM: Artificial Sequence
<220> FEATURE:
<223> OTHER INFORMATION: mutant sequence

<400> SEQUENCE: 33
gaaaaatcct gcaaggaagg gggtggtcgg taagcaccaa                      40

<210> SEQ ID NO 34
<211> LENGTH: 40
<212> TYPE: DNA
<213> ORGANISM: Artificial Sequence
<220> FEATURE:
<223> OTHER INFORMATION: mutant sequence

<400> SEQUENCE: 34
tcattagccc tagttggctt ggtcggtaag caccaagttt                      40

<210> SEQ ID NO 35
<211> LENGTH: 40
<212> TYPE: DNA
<213> ORGANISM: Artificial Sequence
<220> FEATURE:
<223> OTHER INFORMATION: mutant sequence

<400> SEQUENCE: 35
tcattagccc tagttggctt gggtggtcgg taagcaccaa                      40
```

-continued

```
<210> SEQ ID NO 36
<211> LENGTH: 40
<212> TYPE: DNA
<213> ORGANISM: Artificial Sequence
<220> FEATURE:
<223> OTHER INFORMATION: mutant sequence

<400> SEQUENCE: 36
ttggtttagg ccaattgcta acttgagttg ggtcattagg                      40

<210> SEQ ID NO 37
<211> LENGTH: 40
<212> TYPE: DNA
<213> ORGANISM: Artificial Sequence
<220> FEATURE:
<223> OTHER INFORMATION: mutant sequence

<400> SEQUENCE: 37
gattagccct agttggcttg ggccgctaaa gtttagtggg                      40

<210> SEQ ID NO 38
<211> LENGTH: 40
<212> TYPE: DNA
<213> ORGANISM: Artificial Sequence
<220> FEATURE:
<223> OTHER INFORMATION: mutant sequence

<400> SEQUENCE: 38
tggtttaggc caattgctac gggtggtcgg taagcaccaa                      40

<210> SEQ ID NO 39
<211> LENGTH: 40
<212> TYPE: DNA
<213> ORGANISM: Artificial Sequence
<220> FEATURE:
<223> OTHER INFORMATION: mutant sequence

<400> SEQUENCE: 39
gtgttagcct ctgtccgccc cgcagatttc agagcattgt                      40

<210> SEQ ID NO 40
<211> LENGTH: 40
<212> TYPE: DNA
<213> ORGANISM: Artificial Sequence
<220> FEATURE:
<223> OTHER INFORMATION: mutant sequence

<400> SEQUENCE: 40
agccctagtt ggcttgatgt tgattttggt tggaataata                      40

<210> SEQ ID NO 41
<211> LENGTH: 45
<212> TYPE: DNA
<213> ORGANISM: Homo sapiens

<400> SEQUENCE: 41
aaattagtgc gatgagtagg ggaagggagc ctactagggt gtaga                45

<210> SEQ ID NO 42
<211> LENGTH: 45
<212> TYPE: DNA
<213> ORGANISM: Homo sapiens

<400> SEQUENCE: 42
tctacaccct agtaggctcc cttcccctac tcatcgcact aattt                45
```

```
<210> SEQ ID NO 43
<211> LENGTH: 45
<212> TYPE: DNA
<213> ORGANISM: Homo sapiens

<400> SEQUENCE: 43
aatgttagta agggtgggga agcgaggttg acctgttagg gtgag                        45

<210> SEQ ID NO 44
<211> LENGTH: 45
<212> TYPE: DNA
<213> ORGANISM: Homo sapiens

<400> SEQUENCE: 44
ctcaccctaa caggtcaacc tcgcttcccc acccttacta acatt                        45

<210> SEQ ID NO 45
<211> LENGTH: 45
<212> TYPE: DNA
<213> ORGANISM: Homo sapiens

<400> SEQUENCE: 45
aggtggtagt ttgtgtttaa tatttttagt tgggtgatga ggaat                        45

<210> SEQ ID NO 46
<211> LENGTH: 45
<212> TYPE: DNA
<213> ORGANISM: Homo sapiens

<400> SEQUENCE: 46
attcctcatc acccaactaa aaatattaaa cacaaactac cacct                        45

<210> SEQ ID NO 47
<211> LENGTH: 40
<212> TYPE: DNA
<213> ORGANISM: Artificial Sequence
<220> FEATURE:
<223> OTHER INFORMATION: mutant sequence

<400> SEQUENCE: 47
ggtggggaag cgaggttgac cgggccctat ttcaaagatt                              40

<210> SEQ ID NO 48
<211> LENGTH: 40
<212> TYPE: DNA
<213> ORGANISM: Artificial Sequence
<220> FEATURE:
<223> OTHER INFORMATION: mutant sequence

<400> SEQUENCE: 48
tagtagtagt tactggttga ataatttttt attttatgg                               40

<210> SEQ ID NO 49
<211> LENGTH: 45
<212> TYPE: DNA
<213> ORGANISM: Danio rerio

<400> SEQUENCE: 49
agtagcactg ccgctagaat tatagatcct gctacagggg cttct                        45

<210> SEQ ID NO 50
<211> LENGTH: 45
<212> TYPE: DNA
```

<213> ORGANISM: Danio rerio

<400> SEQUENCE: 50
agaagcccct gtagcaggat ctataattct agcggcagtg ctact                          45

<210> SEQ ID NO 51
<211> LENGTH: 45
<212> TYPE: DNA
<213> ORGANISM: Danio rerio

<400> SEQUENCE: 51
accgtcgtgg tattcctgct aaacctagga aatgttgtgg gaaga                          45

<210> SEQ ID NO 52
<211> LENGTH: 45
<212> TYPE: DNA
<213> ORGANISM: Danio rerio

<400> SEQUENCE: 52
tcttcccaca acatttccta ggtttagcag gaataccacg acggt                          45

<210> SEQ ID NO 53
<211> LENGTH: 45
<212> TYPE: DNA
<213> ORGANISM: Danio rerio

<400> SEQUENCE: 53 cgtacccta aagctaatgg tcgaataaat aagctaattg tttcg                           45

<210> SEQ ID NO 54
<211> LENGTH: 45
<212> TYPE: DNA
<213> ORGANISM: Danio rerio

<400> SEQUENCE: 54
cgaaacaatt agcttattta ttcgaccatt agctttaggg gtacg                          45

<210> SEQ ID NO 55
<211> LENGTH: 66
<212> TYPE: DNA
<213> ORGANISM: Artificial Sequence
<220> FEATURE:
<223> OTHER INFORMATION: mutant sequence

<400> SEQUENCE: 55
gctacagggg cttctacatg tgctttggt aggcgtctgg gtagtcagag taccgtcgtg          60
gtattc                                                                     66

<210> SEQ ID NO 56
<211> LENGTH: 55
<212> TYPE: DNA
<213> ORGANISM: Artificial Sequence
<220> FEATURE:
<223> OTHER INFORMATION: mutant sequence

<400> SEQUENCE: 56
gctacagggg cttctacatg tgctttggt tagtcagagt accgtcgtgg tattc               55

<210> SEQ ID NO 57
<211> LENGTH: 62
<212> TYPE: DNA
<213> ORGANISM: Artificial Sequence
<220> FEATURE:
<223> OTHER INFORMATION: mutant sequence -continued

```
<400> SEQUENCE: 57
gctacagggg cttctacatg tgctttttggt gtctgggtag tcagagtacc gtcgtggtat      60
tc                                                                      62

<210> SEQ ID NO 58
<211> LENGTH: 64
<212> TYPE: DNA
<213> ORGANISM: Artificial Sequence
<220> FEATURE:
<223> OTHER INFORMATION: mutant sequence

<400> SEQUENCE: 58
gctacagggg cttctacatg tgctttttggt aagtctgggt agtcagagta ccgtcgtggt      60
attc                                                                    64

<210> SEQ ID NO 59
<211> LENGTH: 65
<212> TYPE: DNA
<213> ORGANISM: Artificial Sequence
<220> FEATURE:
<223> OTHER INFORMATION: mutant sequence

<400> SEQUENCE: 59
gctacagggg cttctacatg tgcttttgga ggcgtctggg tagtcagagt accgtcgtgg      60
tattc                                                                   65

<210> SEQ ID NO 60
<211> LENGTH: 57
<212> TYPE: DNA
<213> ORGANISM: Artificial Sequence
<220> FEATURE:
<223> OTHER INFORMATION: mutant sequence

<400> SEQUENCE: 60
actatcatta gccctagttg gcttgaactt gagttgggtc attaggttga atgtgat         57

<210> SEQ ID NO 61
<211> LENGTH: 61
<212> TYPE: DNA
<213> ORGANISM: Artificial Sequence
<220> FEATURE:
<223> OTHER INFORMATION: mutant sequence

<400> SEQUENCE: 61
actatcatta gccctagttg gcttgatgtt acttgagttg ggtcattagg ttgaatgtga      60
t                                                                       61

<210> SEQ ID NO 62
<211> LENGTH: 62
<212> TYPE: DNA
<213> ORGANISM: Artificial Sequence
<220> FEATURE:
<223> OTHER INFORMATION: mutant sequence

<400> SEQUENCE: 62
actatcatta gccctagttg gcttgatgtt gacttgagtt gggtcattag gttgaatgtg      60
at                                                                      62

<210> SEQ ID NO 63
<211> LENGTH: 64
<212> TYPE: DNA
```

-continued

```
<213> ORGANISM: Artificial Sequence
<220> FEATURE:
<223> OTHER INFORMATION: mutant sequence

<400> SEQUENCE: 63
actatcatta gccctagttg gcttgatgtt gagacttgag ttgggtcatt aggttgaatg      60
tgat                                                                   64

<210> SEQ ID NO 64
<211> LENGTH: 15
<212> TYPE: DNA
<213> ORGANISM: Danio rerio

<400> SEQUENCE: 64
aagttctggt tttaa                                                       15

<210> SEQ ID NO 65
<211> LENGTH: 15
<212> TYPE: DNA
<213> ORGANISM: Danio rerio

<400> SEQUENCE: 65
ttacacctaa ttcct                                                       15

<210> SEQ ID NO 66
<211> LENGTH: 15
<212> TYPE: DNA
<213> ORGANISM: Danio rerio

<400> SEQUENCE: 66
acgagttaga agcat                                                       15

<210> SEQ ID NO 67
<211> LENGTH: 15
<212> TYPE: DNA
<213> ORGANISM: Danio rerio

<400> SEQUENCE: 67
gactaaaatg aacct                                                       15

<210> SEQ ID NO 68
<211> LENGTH: 15
<212> TYPE: DNA
<213> ORGANISM: Danio rerio

<400> SEQUENCE: 68
gctagatgtg gttgg                                                       15

<210> SEQ ID NO 69
<211> LENGTH: 15
<212> TYPE: DNA
<213> ORGANISM: Danio rerio

<400> SEQUENCE: 69
agggctaatg atagt                                                       15

<210> SEQ ID NO 70
<211> LENGTH: 15
<212> TYPE: DNA
<213> ORGANISM: Danio rerio

<400> SEQUENCE: 70
taggttgaat gtgat                                                       15
```

```
<210> SEQ ID NO 71
<211> LENGTH: 15
<212> TYPE: DNA
<213> ORGANISM: Danio rerio

<400> SEQUENCE: 71
tccttactat tattc                                              15

<210> SEQ ID NO 72
<211> LENGTH: 15
<212> TYPE: DNA
<213> ORGANISM: Danio rerio

<400> SEQUENCE: 72
cgggtaataa tgatt                                              15

<210> SEQ ID NO 73
<211> LENGTH: 15
<212> TYPE: DNA
<213> ORGANISM: Danio rerio

<400> SEQUENCE: 73
tatattcgaa gctac                                              15

<210> SEQ ID NO 74
<211> LENGTH: 15
<212> TYPE: DNA
<213> ORGANISM: Danio rerio

<400> SEQUENCE: 74
agaagcccct gtagc                                              15

<210> SEQ ID NO 75
<211> LENGTH: 15
<212> TYPE: DNA
<213> ORGANISM: Danio rerio

<400> SEQUENCE: 75
accgtcgtgg tattc                                              15

<210> SEQ ID NO 76
<211> LENGTH: 15
<212> TYPE: DNA
<213> ORGANISM: Danio rerio

<400> SEQUENCE: 76 cgtacccta aagct                                               15

<210> SEQ ID NO 77
<211> LENGTH: 15
<212> TYPE: DNA
<213> ORGANISM: Danio rerio

<400> SEQUENCE: 77
cgaaacaatt agctt                                              15

<210> SEQ ID NO 78
<211> LENGTH: 15
<212> TYPE: DNA
<213> ORGANISM: Homo sapiens

<400> SEQUENCE: 78
```
aatgttagta agggt                                                        15

<210> SEQ ID NO 79
<211> LENGTH: 15
<212> TYPE: DNA
<213> ORGANISM: Homo sapiens

<400> SEQUENCE: 79
ctcaccctaa caggt                                                        15

<210> SEQ ID NO 80
<211> LENGTH: 15
<212> TYPE: DNA
<213> ORGANISM: Homo sapiens

<400> SEQUENCE: 80
aggtggtagt ttgtg                                                        15

<210> SEQ ID NO 81
<211> LENGTH: 15
<212> TYPE: DNA
<213> ORGANISM: Homo sapiens

<400> SEQUENCE: 81
attcctcatc accca                                                        15

<210> SEQ ID NO 82
<211> LENGTH: 15
<212> TYPE: DNA
<213> ORGANISM: Homo sapiens

<400> SEQUENCE: 82
aaattagtgc gatga                                                        15

<210> SEQ ID NO 83
<211> LENGTH: 15
<212> TYPE: DNA
<213> ORGANISM: Homo sapiens

<400> SEQUENCE: 83
tctacaccct agtag                                                        15

<210> SEQ ID NO 84
<211> LENGTH: 27
<212> TYPE: DNA
<213> ORGANISM: Danio rerio

<400> SEQUENCE: 84
ccaggtgatg aataaggcga ttgaggt                                           27

<210> SEQ ID NO 85
<211> LENGTH: 22
<212> TYPE: DNA
<213> ORGANISM: Danio rerio

<400> SEQUENCE: 85
ggtccgcccg cctaccattt tc                                                22

<210> SEQ ID NO 86
<211> LENGTH: 27
<212> TYPE: DNA
<213> ORGANISM: Danio rerio

<400> SEQUENCE: 86

-continued

```
gcaataatgc ttcctcaggc aagccgt                                      27

<210> SEQ ID NO 87
<211> LENGTH: 26
<212> TYPE: DNA
<213> ORGANISM: Danio rerio

<400> SEQUENCE: 87
gacgcggtac ccggacgatt aaacca                                       26

<210> SEQ ID NO 88
<211> LENGTH: 24
<212> TYPE: DNA
<213> ORGANISM: Danio rerio

<400> SEQUENCE: 88
cggatgaggt tagtccgtgg gcga                                         24

<210> SEQ ID NO 89
<211> LENGTH: 24
<212> TYPE: DNA
<213> ORGANISM: Danio rerio

<400> SEQUENCE: 89
acccgagcat acttcacatc cgcc                                         24

<210> SEQ ID NO 90
<211> LENGTH: 24
<212> TYPE: DNA
<213> ORGANISM: Danio rerio

<400> SEQUENCE: 90
tgattgtaac agtcctcggg ggcc                                         24

<210> SEQ ID NO 91
<211> LENGTH: 25
<212> TYPE: DNA
<213> ORGANISM: Danio rerio

<400> SEQUENCE: 91
aggatcggaa aaaggggggcc catac                                       25

<210> SEQ ID NO 92
<211> LENGTH: 23
<212> TYPE: DNA
<213> ORGANISM: Danio rerio

<400> SEQUENCE: 92
tgctagatgt ggttggttta ggc                                          23

<210> SEQ ID NO 93
<211> LENGTH: 26
<212> TYPE: DNA
<213> ORGANISM: Danio rerio

<400> SEQUENCE: 93
cattcaacct aatgacccaa ctcaag                                       26

<210> SEQ ID NO 94
<211> LENGTH: 30
<212> TYPE: DNA
<213> ORGANISM: Danio rerio
```

-continued

<400> SEQUENCE: 94
ttgctactat cattagccct agttggcttg                               30

<210> SEQ ID NO 95
<211> LENGTH: 25
<212> TYPE: DNA
<213> ORGANISM: Danio rerio

<400> SEQUENCE: 95
gcactgccgc tagaattata gatcc                                    25

<210> SEQ ID NO 96
<211> LENGTH: 26
<212> TYPE: DNA
<213> ORGANISM: Danio rerio

<400> SEQUENCE: 96
tctcacattc ttcccacaac atttcc                                   26

<210> SEQ ID NO 97
<211> LENGTH: 26
<212> TYPE: DNA
<213> ORGANISM: Danio rerio

<400> SEQUENCE: 97
taccgtcgtg gtattcctgc taaacc                                   26

<210> SEQ ID NO 98
<211> LENGTH: 25
<212> TYPE: DNA
<213> ORGANISM: Danio rerio

<400> SEQUENCE: 98
attcaaccta atgacccaac tcaag                                    25

<210> SEQ ID NO 99
<211> LENGTH: 25
<212> TYPE: DNA
<213> ORGANISM: Danio rerio

<400> SEQUENCE: 99
gcccctgagc ataagaataa tatgg                                    25

<210> SEQ ID NO 100
<211> LENGTH: 21
<212> TYPE: DNA
<213> ORGANISM: Danio rerio

<400> SEQUENCE: 100
tccacatctg cactcacgct t                                        21

<210> SEQ ID NO 101
<211> LENGTH: 21
<212> TYPE: DNA
<213> ORGANISM: Danio rerio

<400> SEQUENCE: 101
cccctctgta agatcgaacg g                                        21

<210> SEQ ID NO 102
<211> LENGTH: 23
<212> TYPE: DNA
<213> ORGANISM: Danio rerio

<400> SEQUENCE: 102
acttccacta tgaccattag cca                                                     23

<210> SEQ ID NO 103
<211> LENGTH: 23
<212> TYPE: DNA
<213> ORGANISM: Danio rerio

<400> SEQUENCE: 103
tcggtttgtt tctgccagcg ttg                                                     23

<210> SEQ ID NO 104
<211> LENGTH: 27
<212> TYPE: DNA
<213> ORGANISM: Homo sapiens

<400> SEQUENCE: 104
gcgatggagg taggattggt gctgtgg                                                 27

<210> SEQ ID NO 105
<211> LENGTH: 27
<212> TYPE: DNA
<213> ORGANISM: Homo sapiens

<400> SEQUENCE: 105
ctcatgagct gtccccacat taggctt                                                 27

<210> SEQ ID NO 106
<211> LENGTH: 20
<212> TYPE: DNA
<213> ORGANISM: Homo sapiens

<400> SEQUENCE: 106
gagttttatg gcgtcagcga                                                         20

<210> SEQ ID NO 107
<211> LENGTH: 25
<212> TYPE: DNA
<213> ORGANISM: Homo sapiens

<400> SEQUENCE: 107
ggacaagaga aataaggcct acttc                                                   25

<210> SEQ ID NO 108
<211> LENGTH: 195
<212> TYPE: PRT
<213> ORGANISM: Planomicrobium okeanokoites

<400> SEQUENCE: 108

Leu Val Lys Ser Glu Leu Glu Glu Lys Lys Ser Glu Leu Arg His Lys
1               5                   10                  15

Leu Lys Tyr Val Pro His Glu Tyr Ile Glu Leu Ile Glu Ile Ala Arg
            20                  25                  30

Asn Ser Thr Gln Asp Arg Ile Leu Glu Met Lys Val Met Glu Phe Phe
        35                  40                  45

Met Lys Val Tyr Gly Tyr Arg Gly Lys His Leu Gly Gly Ser Arg Lys
    50                  55                  60

Pro Asp Gly Ala Ile Tyr Thr Val Gly Ser Pro Ile Asp Tyr Gly Val
65                  70                  75                  80

Ile Val Asp Thr Lys Ala Tyr Ser Gly Gly Tyr Asn Leu Pro Ile Gly

-continued

```
                        85              90              95

Gln Ala Asp Glu Met Gln Arg Tyr Val Glu Glu Asn Gln Thr Arg Asn
            100             105             110

Lys His Ile Asn Pro Asn Glu Trp Trp Lys Val Tyr Pro Ser Ser Val
        115             120             125

Thr Glu Phe Lys Phe Leu Phe Val Ser Gly His Phe Lys Gly Asn Tyr
    130             135             140

Lys Ala Gln Leu Thr Arg Leu Asn His Ile Thr Asn Cys Asn Gly Ala
145             150             155             160

Val Leu Ser Val Glu Glu Leu Leu Ile Gly Gly Glu Met Ile Lys Ala
            165             170             175

Gly Thr Leu Thr Leu Glu Glu Val Arg Arg Lys Phe Asn Asn Gly Glu
        180             185             190

Ile Asn Phe
        195

<210> SEQ ID NO 109
<211> LENGTH: 588
<212> TYPE: DNA
<213> ORGANISM: Planomicrobium okeanokoites

<400> SEQUENCE: 109
ctagtgaaat ctgaattgga agagaagaaa tctgaactta gacataaatt gaaatatgtg      60
ccacatgaat atattgaatt gattgaaatc gcaagaaatt caactcagga tagaatcctt     120
gaaatgaagg tgatggagtt ctttatgaag gtttatggtt atcgtggtaa acatttgggt     180
ggatcaagga aaccagacgg agcaatttat actgtcggat ctcctattga ttacggtgtg     240
atcgttgata ctaaggcata ttcaggaggt tataatcttc caattggtca agcagatgaa     300
atgcaaagat atgtcgaaga gaatcaaaca agaaacaagc atatcaaccc taatgaatgg     360
tggaaagtct atccatcttc agtaacagaa tttaagttct gtttgtgag tggtcatttc     420 aaaggaaact acaaagctca gcttacaaga ttgaatcata tcactaattg taatggagct     480
gttcttagtg tagaagagct tttgattggt ggagaaatga ttaaagctgg tacattgaca     540
cttgaggaag tgagaaggaa atttaataac ggtgagataa actttttaa               588

<210> SEQ ID NO 110
<211> LENGTH: 182
<212> TYPE: PRT
<213> ORGANISM: Artificial Sequence
<220> FEATURE:
<223> OTHER INFORMATION: synthetic polypeptide

<400> SEQUENCE: 110

Met Ala Gly Tyr Leu Lys Val Leu Ser Ser Leu Ser Arg Ser Ala Ala
1               5               10              15

Thr Leu Ser Lys Ser Pro Ala Val Leu Ala Pro Ala Cys Gln Ser Leu
            20              25              30

Gln Gln Arg Asn Tyr Ala Asp Lys Arg Ile Gln Ser Arg Asp Val Thr
        35              40              45

Arg Val Asp Leu Arg Thr Leu Gly Tyr Ser Gln Gln Gln Gln Glu Lys
    50              55              60

Ile Lys Pro Lys Val Arg Ser Thr Val Ala Gln His His Glu Ala Leu
65              70              75              80

Val Gly His Gly Phe Thr His Ala His Ile Val Ala Leu Ser Gln His
            85              90              95
```

-continued

```
Pro Ala Ala Leu Gly Thr Val Ala Val Thr Tyr Gln His Ile Ile Thr
            100                 105                 110

Ala Leu Pro Glu Ala Thr His Glu Asp Ile Val Gly Val Gly Lys Gln
            115                 120                 125

Trp Ser Gly Ala Arg Ala Leu Glu Ala Leu Leu Thr Asp Ala Gly Glu
            130                 135                 140

Leu Arg Gly Pro Pro Leu Gln Leu Asp Thr Gly Gln Leu Val Lys Ile
145                 150                 155                 160

Ala Lys Arg Gly Gly Val Thr Ala Met Glu Ala Val His Ala Ser Arg
                165                 170                 175

Asn Ala Leu Thr Gly Ala
            180

<210> SEQ ID NO 111
<211> LENGTH: 242
<212> TYPE: PRT
<213> ORGANISM: Artificial Sequence
<220> FEATURE:
<223> OTHER INFORMATION: synthetic polypeptide

<400> SEQUENCE: 111

His Leu Val Ala Leu Ala Cys Leu Gly Gly Arg Pro Ala Met Asp Ala
1               5                   10                  15

Val Lys Lys Gly Leu Pro His Ala Pro Glu Leu Ile Arg Arg Val Asn
                20                  25                  30

Arg Arg Ile Gly Glu Arg Thr Ser His Arg Val Ala Ser Arg Ser Gln
            35                  40                  45

Leu Val Lys Ser Glu Leu Glu Glu Lys Lys Ser Glu Leu Arg His Lys
            50                  55                  60

Leu Lys Tyr Pro His Glu Tyr Ile Glu Leu Ile Glu Ile Ala Arg Asn
65                  70                  75                  80

Ser Thr Gln Asp Arg Ile Leu Glu Met Lys Val Met Glu Phe Phe Met
                85                  90                  95

Lys Val Tyr Gly Tyr Arg Gly Lys His Leu Gly Gly Ser Arg Lys Pro
            100                 105                 110

Asp Gly Ala Ile Tyr Thr Val Gly Ser Pro Ile Asp Tyr Gly Val Ile
            115                 120                 125

Val Asp Thr Lys Ala Tyr Ser Gly Gly Tyr Asn Leu Pro Ile Gly Gln
            130                 135                 140

Ala Asp Glu Met Gln Arg Tyr Val Glu Glu Asn Gln Thr Arg Asn Lys
145                 150                 155                 160

His Ile Asn Pro Asn Glu Trp Trp Lys Val Tyr Pro Ser Ser Val Thr
                165                 170                 175

Glu Phe Lys Phe Leu Phe Val Ser Gly His Phe Lys Gly Asn Tyr Lys
            180                 185                 190

Ala Gln Leu Thr Arg Leu Asn His Ile Thr Asn Cys Asn Gly Ala Val
            195                 200                 205

Leu Ser Val Glu Glu Leu Leu Ile Gly Gly Glu Met Ile Lys Ala Gly
            210                 215                 220

Thr Leu Thr Leu Glu Glu Val Arg Arg Lys Phe Asn Asn Gly Glu Ile
225                 230                 235                 240

Asn Phe

<210> SEQ ID NO 112
<211> LENGTH: 9
<212> TYPE: PRT
```

-continued

```
<213> ORGANISM: Artificial Sequence
<220> FEATURE:
<223> OTHER INFORMATION: consensus sequence

<400> SEQUENCE: 112

Leu Ala Gly Leu Ile Asp Ala Asp Gly
1               5
```